(12) United States Patent
Sjöstrand et al.

(10) Patent No.: US 11,937,962 B2
(45) Date of Patent: Mar. 26, 2024

(54) SYSTEMS AND METHODS FOR AUTOMATED AND INTERACTIVE ANALYSIS OF BONE SCAN IMAGES FOR DETECTION OF METASTASES

(71) Applicants: Progenics Pharmaceuticals, Inc., N. Billerica, MA (US); EXINI Diagnostics AB, Lund (SE)

(72) Inventors: Karl Vilhelm Sjöstrand, Atlantic Highlands, NJ (US); Jens Filip Andreas Richter, Lund (SE); Lars Edenbrandt, Lund (SE)

(73) Assignees: Progenics Pharmaceuticals, Inc., N. Billerica, MA (US); EXINI Diagnostics AB, Lund (SE)

( * ) Notice: Subject to any disclaimer, the term of this patent is extended or adjusted under 35 U.S.C. 154(b) by 0 days.

(21) Appl. No.: 17/989,863

(22) Filed: Nov. 18, 2022

(65) Prior Publication Data

US 2023/0148980 A1    May 18, 2023

Related U.S. Application Data

(63) Continuation of application No. 16/856,120, filed on Apr. 23, 2020, now Pat. No. 11,534,125.

(Continued)

(51) Int. Cl.
*G06K 9/00* (2022.01)
*A61B 6/00* (2006.01)
(Continued)

(52) U.S. Cl.
CPC ............. *A61B 6/469* (2013.01); *A61B 6/037* (2013.01); *A61B 6/465* (2013.01); *A61B 6/505* (2013.01);
(Continued)

(58) Field of Classification Search
CPC ......... A61B 6/469; A61B 6/037; A61B 6/465; A61B 6/505; A61B 6/5217; A61B 6/5258;
(Continued)

(56) References Cited

U.S. PATENT DOCUMENTS 5,762,608 A * 6/1998 Warne ................. A61B 6/4258
378/197
7,450,747 B2   11/2008 Jabri et al.
(Continued)

FOREIGN PATENT DOCUMENTS

CN        1200520 A     12/1998
CN      101528267 A      9/2009
(Continued)

OTHER PUBLICATIONS

Huang et al ("A Set of Image Processing Algorithms for Computer-Aided Diagnosis in Nuclear Medicine Whole Body Bone Scan Images". IEEE, Nuclear science, vol. 54, No. 3, Jun. 2007). (Year: 2007).*

(Continued)

*Primary Examiner* — Shervin K Nakhjavan
(74) *Attorney, Agent, or Firm* — William R. Haulbrook; Ronen Adato; Samuel R. Polio

(57) ABSTRACT

Presented herein are systems and methods that provide for improved computer aided display and analysis of nuclear medicine images. In particular, in certain embodiments, the systems and methods described herein provide improvements to several image processing steps used for automated analysis of bone scan images for assessing cancer status of a patient. For example, improved approaches for image segmentation, hotspot detection, automated classification of hotspots as representing metastases, and computation of risk indices such as bone scan index (BSI) values are provided.

30 Claims, 35 Drawing Sheets

Related U.S. Application Data

(60) Provisional application No. 62/837,955, filed on Apr. 24, 2019.

(51) Int. Cl.

| | | |
|---|---|---|
| *A61B 6/03* | (2006.01) | |
| *A61K 51/04* | (2006.01) | |
| *G06T 7/00* | (2017.01) | |
| *G06T 7/11* | (2017.01) | |
| *G06T 7/73* | (2017.01) | |
| *G16H 15/00* | (2018.01) | |
| *G16H 30/20* | (2018.01) | |
| *G16H 30/40* | (2018.01) | |
| *G16H 50/20* | (2018.01) | |
| *G16H 50/30* | (2018.01) | |
| *G16H 50/70* | (2018.01) | |
| *G16H 70/60* | (2018.01) | |

(52) U.S. Cl.
CPC .......... *A61B 6/5217* (2013.01); *A61B 6/5258* (2013.01); *A61B 6/563* (2013.01); *A61K 51/0489* (2013.01); *G06T 7/0012* (2013.01); *G06T 7/11* (2017.01); *G06T 7/73* (2017.01); *G16H 15/00* (2018.01); *G16H 30/20* (2018.01); *G16H 30/40* (2018.01); *G16H 50/20* (2018.01); *G16H 50/30* (2018.01); *G16H 50/70* (2018.01); *G16H 70/60* (2018.01); *G06T 2200/24* (2013.01); *G06T 2207/30008* (2013.01); *G06T 2207/30096* (2013.01)

(58) Field of Classification Search
CPC .. A61B 6/563; A61K 51/0489; G06T 7/0012; G06T 7/11; G06T 7/73; G06T 2200/24; G06T 2207/30008; G06T 2207/30096; G06T 2207/10128; G06T 2207/20012; G06T 2207/20128; G06T 7/0014; G16H 15/00; G16H 30/20; G16H 30/40; G16H 50/20; G16H 50/30; G16H 50/70; G16H 70/60
See application file for complete search history.

(56) References Cited

U.S. PATENT DOCUMENTS

| | | | |
|---|---|---|---|
| 7,751,605 B2 | 7/2010 | Gündel et al. | |
| 7,935,055 B2 | 5/2011 | Burckhardt | |
| 7,970,194 B2 | 6/2011 | Kimura | |
| 8,199,985 B2 | 6/2012 | Jakobsson et al. | |
| 8,211,401 B2 | 7/2012 | Babich et al. | |
| 8,467,856 B2 | 6/2013 | Renisch et al. | |
| 8,538,166 B2 | 9/2013 | Gordon et al. | |
| 8,705,887 B2 | 4/2014 | Ma et al. | |
| 8,778,305 B2 | 7/2014 | Pomper et al. | |
| 8,855,387 B2 * | 10/2014 | Hamadeh | A61B 6/48 382/128 |
| 8,962,799 B2 | 2/2015 | Babich et al. | |
| 8,995,736 B2 | 3/2015 | Kaufman et al. | |
| 9,002,081 B2 | 4/2015 | Brown | |
| 9,466,133 B2 | 10/2016 | Sowards-Emmerd et al. | |
| 9,710,915 B2 | 7/2017 | Firouzian et al. | |
| 9,721,340 B2 | 8/2017 | Gillies et al. | |
| 10,058,393 B2 * | 8/2018 | Bonutti | G06T 7/11 |
| 10,223,610 B1 | 3/2019 | Akselrod-Ballin et al. | |
| 10,311,971 B2 | 6/2019 | Opfer et al. | |
| 10,330,763 B2 | 6/2019 | James et al. | |
| 10,339,653 B2 | 7/2019 | Gillies et al. | |
| 10,340,044 B2 | 7/2019 | Yao et al. | |
| 10,340,046 B2 | 7/2019 | Baker | |
| RE47,609 E | 9/2019 | Hamadeh et al. | |
| 10,492,723 B2 | 12/2019 | Madabhushi et al. | |
| 10,600,184 B2 | 3/2020 | Golden et al. | |
| 10,665,346 B2 | 5/2020 | Baker | |
| 10,748,652 B2 | 8/2020 | Yao et al. | |
| 10,762,993 B2 | 9/2020 | Baker | |
| 10,818,386 B2 | 10/2020 | Yao et al. | |
| 10,943,681 B2 | 3/2021 | Yao et al. | |
| 10,973,486 B2 | 4/2021 | Sjostrand et al. | |
| 11,011,257 B2 | 5/2021 | Lints et al. | |
| 11,321,844 B2 | 5/2022 | Johnsson et al. | |
| 11,386,988 B2 | 7/2022 | Johnsson et al. | |
| 11,424,035 B2 | 8/2022 | Baker | |
| 11,534,125 B2 | 12/2022 | Sjöstrand et al. | |
| 11,564,621 B2 | 1/2023 | Anand et al. | |
| 11,657,508 B2 | 5/2023 | Richter et al. | |
| 11,721,428 B2 | 8/2023 | Brynolfsson et al. | |
| 2003/0215120 A1 | 11/2003 | Uppaluri et al. | |
| 2005/0281381 A1 | 12/2005 | Guendel | |
| 2006/0062425 A1 | 3/2006 | Shen et al. | |
| 2006/0064396 A1 | 3/2006 | Wei et al. | |
| 2006/0078183 A1 | 4/2006 | deCharms | |
| 2007/0081712 A1 | 4/2007 | Huang et al. | |
| 2007/0081713 A1 | 4/2007 | Jerebko | |
| 2007/0100225 A1 | 5/2007 | Maschke | |
| 2007/0115204 A1 | 5/2007 | Budz et al. | |
| 2008/0027315 A1 | 1/2008 | McGinnis | |
| 2009/0309874 A1 | 12/2009 | Salganicoff et al. | |
| 2009/0311182 A1 * | 12/2009 | Wang | A61K 49/0054 424/9.1 |
| 2010/0215581 A1 | 8/2010 | Hoffmann | |
| 2010/0266170 A1 | 10/2010 | Khamene et al. | |
| 2010/0322488 A1 | 12/2010 | Virtue et al. | |
| 2011/0063288 A1 | 3/2011 | Valadez | |
| 2011/0255763 A1 | 10/2011 | Bogoni et al. | |
| 2012/0123253 A1 | 5/2012 | Renisch et al. | |
| 2013/0038707 A1 | 2/2013 | Cunningham et al. | |
| 2013/0094704 A1 * | 4/2013 | Hamadeh | G06N 3/02 382/103 |
| 2013/0129168 A1 | 5/2013 | Ross | |
| 2013/0211231 A1 | 8/2013 | Sundarapandian et al. | |
| 2013/0281841 A1 | 10/2013 | Everett et al. | |
| 2014/0193336 A1 * | 7/2014 | Rousso | A61B 6/503 600/431 |
| 2015/0110716 A1 | 4/2015 | Armor | |
| 2015/0119704 A1 * | 4/2015 | Roth | G01T 1/1603 600/425 |
| 2015/0331995 A1 | 11/2015 | Zhao et al. | |
| 2016/0203263 A1 | 7/2016 | Maier et al. | |
| 2016/0335395 A1 | 11/2016 | Wu et al. | |
| 2017/0083682 A1 | 3/2017 | McNutt et al. | |
| 2017/0112577 A1 * | 4/2017 | Bonutti | G06T 7/11 |
| 2018/0144828 A1 | 5/2018 | Baker | |
| 2018/0259608 A1 | 9/2018 | Golden et al. | |
| 2018/0360402 A1 | 12/2018 | Carmi | |
| 2019/0038239 A1 | 2/2019 | Flohr et al. | |
| 2019/0105009 A1 | 4/2019 | Siemionow et al. | |
| 2019/0209116 A1 | 7/2019 | Sjostrand et al. | |
| 2019/0388049 A1 | 12/2019 | Gupta et al. | |
| 2020/0027559 A1 | 1/2020 | Baker | |
| 2020/0051238 A1 | 2/2020 | El Harouni et al. | |
| 2020/0074634 A1 | 3/2020 | Kecskemethy et al. | |
| 2020/0085382 A1 | 3/2020 | Taerum et al. | |
| 2020/0126666 A1 | 4/2020 | Baker | |
| 2020/0170604 A1 * | 6/2020 | Yildirim | G06T 7/0014 |
| 2020/0193594 A1 | 6/2020 | Georgescu et al. | |
| 2020/0193603 A1 | 6/2020 | Golden et al. | |
| 2020/0245960 A1 | 8/2020 | Richter et al. | |
| 2020/0311919 A1 | 10/2020 | Grimmer et al. | |
| 2020/0315455 A1 | 10/2020 | Lee et al. | |
| 2020/0337658 A1 | 10/2020 | Sjostrand et al. | |
| 2020/0342600 A1 | 10/2020 | Sjostrand et al. | |
| 2020/0352518 A1 | 11/2020 | Lyman et al. | |
| 2020/0357117 A1 | 11/2020 | Lyman et al. | |
| 2020/0357118 A1 | 11/2020 | Yao et al. | |
| 2020/0357521 A1 | 11/2020 | Baker | |
| 2020/0410672 A1 * | 12/2020 | Katscher | G06T 7/0012 |
| 2021/0032206 A1 | 2/2021 | Neumaier et al. | |
| 2021/0082547 A1 | 3/2021 | Yao et al. | |
| 2021/0093249 A1 | 4/2021 | Anand et al. | |
| 2021/0183485 A1 | 6/2021 | Yao et al. | |

(56) References Cited

U.S. PATENT DOCUMENTS

| | | | |
|---|---|---|---|
| 2021/0233633 | A1 | 7/2021 | Lints et al. |
| 2021/0334974 | A1 | 10/2021 | Johnsson et al. |
| 2021/0335480 | A1 | 10/2021 | Johnsson et al. |
| 2022/0005586 | A1 | 1/2022 | Brynolfsson et al. |
| 2022/0375612 | A1 | 11/2022 | Baker |
| 2022/0398724 | A1 | 12/2022 | Anand et al. |
| 2023/0115732 | A1 | 4/2023 | Brynolfsson et al. |
| 2023/0316530 | A1 | 10/2023 | Richter et al. |

FOREIGN PATENT DOCUMENTS

| | | |
|---|---|---|
| CN | 102361594 A | 2/2012 |
| CN | 102947840 A | 2/2013 |
| CN | 103607954 A | 2/2014 |
| CN | 106558045 A | 4/2017 |
| CN | 107644421 A | 1/2018 |
| EP | 1426903 A2 | 6/2004 |
| EP | 1508872 A1 | 2/2005 |
| EP | 3043318 A1 | 7/2016 |
| GB | 2457577 A | 8/2009 |
| JP | 2010-029481 A | 2/2010 |
| JP | 2011-067594 A | 4/2011 |
| JP | 2014-006130 A | 1/2014 |
| JP | 2015-513083 A | 4/2015 |
| JP | 6013042 B2 | 10/2016 |
| JP | 2017067489 A | 4/2017 |
| JP | 6170284 B2 | 7/2017 |
| SE | 524500 C2 | 8/2004 |
| TW | 201201847 A | 1/2012 |
| WO | WO-99/05503 A2 | 2/1999 |
| WO | WO-2007/062135 A2 | 5/2007 |
| WO | WO-2009/084995 A1 | 7/2009 |
| WO | WO-2011/077303 A1 | 6/2011 |
| WO | WO-2011/091378 A1 | 7/2011 |
| WO | WO-2011/095580 A1 | 8/2011 |
| WO | WO-2013/126147 A2 | 8/2013 |
| WO | WO-2015/058151 A2 | 4/2015 |
| WO | WO-2018/014475 A1 | 1/2018 |
| WO | WO-2018/015953 A1 | 1/2018 |
| WO | WO-2018/081354 A1 | 5/2018 |
| WO | WO-2019/005722 A1 | 1/2019 |
| WO | WO-2019/103912 A2 | 5/2019 |
| WO | WO-2019/136349 A2 | 7/2019 |
| WO | WO-2020/144134 A1 | 7/2020 |
| WO | WO-2020/146032 A1 | 7/2020 |
| WO | WO-2020/190821 A1 | 9/2020 |
| WO | WO-2020/219619 A1 | 10/2020 |
| WO | WO-2020/219620 A1 | 10/2020 |
| WO | WO-2021/061315 A1 | 4/2021 |
| WO | WO-2022/008374 A1 | 1/2022 |
| WO | WO-2023/057411 A1 | 4/2023 |

OTHER PUBLICATIONS

Yin et al ("A Computer-Aided Diagnosis for Locating Abnormalities in Bone Scintigraphy by a Fuzzy System With a Three-Step Minimization Approach", IEEE Transactions on Medical Imaging, vol. 23, No. 5, May 2004). (Year: 2004).*

Gorthi, S. et al., Segmentation of Head and Neck Lymph Node Regions for Radiotherapy Planning Using Active Contour-Based Atlas Registration, IEEE Journal of Selected Topics in Signal Processing, 3(1):135-147 (2009).

Grahovac, M. et al., Machine learning predictive performance evaluation of conventional and fuzzy radiomics in clinical cancer imaging cohorts, Eur. J. Med. Mol. Imaging, 50(6):1607-1620 (2023).

International Search Report for PCT/EP2022/077505, filed Oct. 4, 2022, 9 pages, (dated Mar. 23, 2023).

Invitation to Pay Additional Fees for PCT/EP2022/077505, filed Oct. 4, 2022, 15 pages, (dated Feb. 2, 2023).

Kertesz, H. et al., Implementation of a Spatially-Variant and Tissue-Dependent Positron Range Correction for PET/CT Imaging, Front. Physiol., 13:818463 (2022).

Kertesz, H. et al., Positron range in combination with point-spread-function correction: an evaluation of different implementations for [124I]-PET imaging, ENJMMI Phys., 9(1):56 (2022).

Khurshid, Z. et al., Role of textural heterogeneity parameters in patient selection for 177Lu-PSMA therapy via response prediction, Oncotarget., 9(70):33312-33321 (2018).

Krajnc, D. et al., Automated data preparation for in vivo tumor characterization with machine learning, Front. Oncol., 12:1017911 (2022).

Papp, L. et al., Glioma Survival Prediction with Combined Analysis of In Vivo 11C-MET PET Features, Ex Vivo Features, and Patient Features by Supervised Machine Learning, J. Nucl. Med., 59(6):892-899 (2018).

Papp, L. et al., Optimized Feature Extraction for Radiomics Analysis of 18F-FDG PET Imaging, J. Nucl. Med., 60(6):864-872 (2019).

Papp, L. et al., Supervised machine learning enables non-invasive lesion characterization in primary prostate cancer with [68Ga]Ga-PSMA-11 PET/MRI, Eur. J. Nucl. Mol. Imaging, 48(6):1795-1805 (2021).

Teng, C. et al., Head and neck lymph node region delineation using a hybrid image registration method, 3rd IEEE International Symposium on Biomedical Imaging: Nano to Macro, 4 pages, (2006).

Valladares, A. et al., A multi-modality physical phantom for mimicking tumor heterogeneity patterns in PET/CT and PET/MRI, Med. Phys., 49(9):5819-5829 (2022).

Written Opinion for PCT/EP2022/077505, filed Oct. 4, 2022, 11 pages, (dated Mar. 23, 2023).

Ali, A. et al., The Automated Bone Scan Index as a Predictor of Response to Prostate Radiotherapy in Men with Newly Diagnosed Metastatic Prostate Cancer: An Exploratory Analysis of STAMPEDE's "M1|RT Comparison", European Urology Oncology 3:412-419, (2020).

American College of Radiology (ACR) and the Society for Pediatric Radiology (SPR), ACR-SPR Practice Parameter For The Performance Of Skeletal Scintigraphy (Bone Scan), Resolution 28, (2013-Revused2017), available from: <http://www.acr.org>, 9 pages (2017).

Anand, A. et al., A Pre-Analytical Validation Study of Automated Bone Scan Index: Effect on Accuracy and Reproducibility Due to the Procedural Variabilities in Bone Scan Image Acquisition. J Nucl Med. pp. 1865-1871, (2016).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, 1 page, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138, 5 pages, (2017).

Armstrong, A. J. et al., Phase 3 Assessment of the Automated Bone Scan Index as a Prognostic Imaging Biomarker of Overall Survival in Men with Metastatic Castration-Resistant Prostate Cancer: A Secondary Analysis of a Randomized Clinical Trial. JAMA Oncology 4:944-951, (2018).

(56) References Cited

OTHER PUBLICATIONS

Armstrong, A. J. et al., Phase 3 prognostic analysis of the automated bone scan index (aBSI) in men with bone-metastatic castration-resistant prostate cancer (CRPC), Meeting Library ASC University, 11 pages (2017).
Bai, P. et. al., Body region localization in whole-body low-dose CT images of PET/CT scans using virtual landmarks, Medical Physics Wiley USA, 46(3): 1286-1299 (2019).
Belal, S. et al., Association of PET Index quantifying skeletal uptake in NaF PET/CT images with overall survival in prostate cancer patients, ASCO GU 2017, Poster 178, 1 page, presented Feb. 16, 2017.
Belal, S. et al., PET Index quantifying skeletal uptake in NaF PET/CT images with overall survival in prostate cancer patients, ASCO GU 2017, Abstract, 1 page, (Feb. 13, 2017).
Belal, S. L. et al, 3D skeletal uptake of $^{18}$F sodium fluoride in PET/CT images is associate with overall survival in patients with prostate cancer, EJNMMI Research, 7(15):1-8 (2017).
Belal, S.L. et al., Automated evaluation of normal uptake in different skeletal parts in 18F-sodium fluoride (NaF) PET/CT using a new convolutional neural network method, EJNMMI, EANM '17, 44(Suppl 2):S119-S956, Abstract EP-0116 (2017).
Bombardieri, E. et al., Bone scintigraphy: procedure guidelines for tumour imaging, Eur J. Nucl. Med. Mol. Imaging, 30:BP99-BP106, (2003).
Brynolfsson, J., et. al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. pp. S1 and S403-404, Retrieved Sep. 18, 2020.
Brynolfsson, J., et. al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. pp. S1 and S273, Retrieved Sep. 18, 2020.
Bushberg, J. T. et al., Essential Physics of Medical Imaging, Essential Physics of Medical Imaging, 19.3: p. 581 (table 15-3), p. 713 paragraph 6, section 19.3 and p. 720, (2011).
Capobianco, N. et. al., Whole-body uptake classification and prostate cancer staging in $^{68}$Ga-PSMA-11 PET/CT using dual-tracer learning, European Journal of Nuclear Medicine and Molecular Imaging, (2021), <https://doi.org/10.1007/s00259-021-05473-2> 10 pages. Retrieved on Apr. 18, 2021.
Ceci, F. et al., E-PSMA: the EANM standardized reporting guidelines v1.0 for PSMA-PET, European Journal of Nuclear Medicine and Molecular Imaging, 48:1626-1638, (2021).
Cha, K. H., et al. Urinary bladder segmentation in CT urography using deep-learning convolutional neural network and level sets, Medical physics, 43(4):1882-1896, (2016).
Christ, P.F. et al., Automatic Liver and Tumor Segmentation of CT and MRI Volumes Using Cascaded Fully Convolutional Neural Networks, Arxiv.org, Cornell University Library, 20 pages, (2017).
Ciernik, I. F., et al. 3D-segmentation of the 18F-choline PET signal for target volume definition in radiation therapy of the prostate, Technology in cancer research & treatment 6(1): 23-30, (2007).
Communication pursuant to Article 94(3) EPC for European Application No. 17794628.2-1126, 6 pages, (dated Apr. 22, 2021).
Dennis, E. et al., Bone Scan Index: A Quantitative Treatment Response Biomarker for Castration-Resistant Metastatic Prostate Cancer, Journal of Clinical Oncology, 30(5):519-524 (2012).
Dertat, A., Applied Deep Learning—Part 4: Convolutional Neural Networks, Towards Data Science,<http://towardsdatascience.com/applied-deep-learning-part-4-convolutional-neural-networks-584bc134c1e2> 26 pages, (2017).
Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).

Fendler, W.P. et. al., $^{68}$Ga-PSMA PET/CT: Joint EANM and SNMMI procedure guideline for prostate cancer imaging: version 1.0, Eur J Nucl Med Mol Imaging, DOI 10.1007/s00259-017-3670-z, 11 pages, (2017).
GE Healthcare, SPECT/CT Cameras, 2 pages, retrieved Oct. 25, 2017: <http://www3.gehealthcare.com.sg/en-gb/products/categories/nuclear_medicine/spect-ct_cameras>.
Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).
Gjertsson, K., et. al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.
Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.
Goffin, K. E. et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages (2017).
Guimond, A. et al., Average Brain Models: A Convergence Study, Computer Vision and Image Understanding, 77:192-210 (2000).
Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).
Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.
Horikoshi, H. et al., Computer-aided diagnosis system for bone scintigrams from Japanese patients: importance of training database, Annals of Nuclear Medicine, 26(8):622-626 (2012).
Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).
Im, HJ, et. al., et. al., Current Methods to Define Metabolic Tumor Volume in Positron Emission Tomography: Which One is Better?, Nucl. Med. Mol. Imaging, 52(1):5-15, (2018).
International Search Report for PCT/US2020/029435, filed Apr. 23, 2020, 4 pages, (dated Jul. 16, 2020).
Johnsson, K. et al., Analytical performance of aPROMISE: automated anatomic contextualization, detection, and quantification of [18F]DCFPyL (PSMA) imaging for standardized reporting, European Journal of Nuclear Medicin and Molecular Imaging, 11 pages, Aug. 31, 2021, doi: 10.1007/s00259-021-05497-8. Epub ahead of print. PMID: 34463809.
Johnsson, K., et. al., miPSMA Index: Comprehensive and Automated Quantification of 18F-DCFPyL (PyL-PSMA) PET/CT for Prostate Cancer Staging, J Nucl Med., 61: (Supplement 1): 1435, 5 pages, (2020).
Kaboteh R. et al., Progression of bone metastases in patients with prostate cancer—automated detection of new lesions and calculation of bone scan index, EJNMMI Research, 3:64, 6 pages, (2013).
Kaboteh, R. et al., Convolutional neural network based quantification of choline uptake in PET/CT studies is associated with overall survival in patents with prostate cancer, EJNMMI, EANM '17, 44(Suppl 2):S119-S956, Abstract EP-0642 (2017).
Kiess, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultra-

(56) References Cited

OTHER PUBLICATIONS sound CT MR 31(6):496-505 (2010) retrieved Oct. 25, 2017: <https://www.ncbi.nlm.nih.gov/pmc/articles/PMC3026294/>.

Knutsson, H., and Andersson, M., Morphons: Segmentation using Elastic Canvas and Paint on Priors, IEEE International Conference on Image Processing (ICIP 2005), Genova, Italy, 4 pages (2005).

Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).

Lin, T.Y. et. al., Feature Pyramid Networks for object detection, FAIR, 10 pages, (2016), <https://arxiv.org/abs/1612.03144v1>.

Litjens, G. et al., A survey on deep learning in medical image analysis, Medical Image Analysis, 42:60-88, (2017).

Liu, L. et al., Computer-Aided Detection of Prostate Cancer with MRI: Technology and Applications, Acad Radiol. Author manuscript, 50 pages 2016.

Ma, L. et al., Automatic segmentation of the prostate on CT images using deep learning and multi-atlas fusion, Proc. of SPIE vol. 10133:101332O-1-101332O-9 (2017).

Ma, L. et al., Combining Population and Patient-Specific Characteristics for Prostate Segmentation on 3D CT Images, Proc of SPIE 9784:978427-1-8 (2016).

Ma, L. et al., Random Walk Based Segmentation for the Prostate on 3D Transrectal Ultrasound Images, Proc SPIE Int Soc Opt Eng. Author manuscript, 13 pages (2016).

Matsubara, N. et al, A Phase II, Randomized, Open-Label, Multi-arm Study of TAS-115 for Castration-Resistant Prostate Cancer Patients With Bone Metastases, Clinical Genitourinary Cancer, 000(xxx):1-10, (2021).

Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.

Meyer, A., et. al., Deep learning algorithm improves identification of men with low-risk prostate cancer using PSMA targeted 99mTc-MIP-1404 SPECT/CT, Journal of Clinical Oncology, 37:(15), (2019).

Nakajima, K. et al., Enhanced diagnostic accuracy for quantitative bone scan using an artificial neural network system: a Japanese multi-center database project, EJNMMI Research, 3:83, 9 pages, (2013).

National Cancer Institute, NCI Drug Dictionary: gallium Ga 68-labeled PSMA-11, 1 page, retrieved Oct. 25, 2017: <https://www.cancer.gov/publications/dictionaries/cancer-drug?cdrid=766400>.

National Cancer Institute, NCI Drug Dictionary: technetium Tc 99m methylene diphosphonate, 1 page, retrieved Oct. 25, 2017: <https://www.cancer.gov/publications/dictionaries/cancer-drug?cdrid=537722>.

Nickols, N. et al., aPROMISE: A Novel Automated-PROMISE platform to Standardize Evaluation of Tumor Burden in 18F-DCFPyL (PSMA) images of Veterans with Prostate Cancer, Journal of Nuclear Medicine, 26 pages, May 28, 2021, doi: 10.2967/jnumed.120.261863.

Nickols, N.G., et. al., A deep learning algorithm to predict coexisting metastatic disease using intraprostatic [F18]DCFPYL PSMA image alone in veterans with prostate cancer, Journal of Clinical Oncology 38. (Supplement 6), 2020.

Ohlsson, M., et. al., Automated decision support for bone scintigraphy, Computer-based medical systems, pp. 1-6, (2009).

Paschalis, A. et al., Prostate-specific Membrane Antigen Heterogeneity and DNA Repair Defects in Prostate Cancer, European Urology, 76(4):469-478, (2019).

Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).

Polymeri, E. et al., Analytical validation of an automated method for segmentation of the prostate gland in CT images, EJNMMI, EANM '17, 44(Suppl 2):S119-S956, Abstract EP-0641 (2017).

Polymeri, E., et. al., Deep learning-based quantification of PET/CT prostate gland uptake: association with overall survival, Clinical Physiology Functional Imaging, DOI: 10.1111/cpf.12611, 40(2):106-113, (2019).

Pouliot, F., et. al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.

radiologyinfo.org for Patients, Computed Tomography (CT). 2 pages, retrieved Oct. 25, 2017: <https://www.radiologyinfo.org/en/submenu.cfm?pg=ctscan>.

Ren, S., et. al., Faster R-CNN: Towards Real-Time Object Detection with Region Proposal Networks, 14 pages, (2015), <http://image-net.org/challenges/LSVRC/2015/results>.

Ronneberger, O., et. al., U-Net: Convolutional Networks for Biomedical Image Segmentation, Springer International Publishing, pp. 234-241, (2015), <http://lmb.informatik.uni-freiburg.de/>. Published online on Nov. 18, 2015.

Rowe, S. P. et al., PET Imaging of prostate-specific membrane antigen in prostate cancer: current state of the art and future challenges, Prostate Cancer and Prostatic Diseases, pp. 1-8 (2016).

Rowe, S. P. et al., PSMA-Based [$^{18}$F]DCFPyL PET/CT Is Superior to Conventional Imaging for Lesion Detection in Patients with Metastatic Prostate Cancer, Mol Imaging Biol, 18:411-419, (2016).

Sabbatini, P. et al., Prognostic Significance of Extent of Disease in Bone in Patients With Androgen-Independent Prostate Cancer, Journal of Clinical Oncology, 17(3):948-957 (1999).

Sadik, M. et al., 3D prostate gland uptake of 18F-choline—association with overall survival in patients with hormone-naïve prostate cancer, The Journal of Nuclear Medicine, 58(Suppl. 1):Abstract 544, 2 pages, (2017).

Sadik, M. et al., A new computer-based decision-support system for the interpretation of bone scans, Nuclear Medicine Communications, 27(5):417-423 (2006).

Sadik, M. et al., Automated 3D segmentation of the prostate gland in CT images—a first step towards objective measurements of prostate uptake in PET and SPECT images, Journal of Nuclear Medicine, 58(1):1074, (2017).

Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).

Sadik, M. et al., Computer-assisted interpretation of planar whole-body bone scans, Journal Nuclear Medicine, 49(12):1958-65, 2008.

Sadik, M. et al., Convolutional neural networks for segmentation of 49 selected bones in CT images show high reproducibility, EJNMMI, EANM '17, 44(Suppl 2):S119-S956, Abstract OP-657 (2017).

Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.

Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).

Sajn, L. et al., Computerized segmentation of whole-body bone scintigrams and its use in automated diagnostics, Computer Methods and Programs in Biomedicine, 80:47-55 (2005).

Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).

Santos-Cuevas, C. et al. 99mTc-labeled PSMA inhibitor: Biokinetics and radiation dosimetry in healthy subjects and imaging of prostate cancer tumors in patients, Nuclear Medicine and Biology 52:1-6, (2017).

Shi, F. et al., Deep learning empowered volume delineation of whole-body organs-at-risk for accelerated radiotherapy, Nat. Commun., 13(1):6566 (2022).

(56) References Cited

OTHER PUBLICATIONS

Sjöstrand K. et al., Statistical regularization of deformation fields for atlas-based segmentation of bone scintigraphy images, MICCAI 5761:664-671 (2009).

Sjöstrand, K., et al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).

Sjostrand, K., et. al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, 1 page, (2019).

Sluimer, I. et al., Toward Automated Segmentation of the Pathological Lung in CT, IEEE Transactions on Medical Imaging, 24(8):1025-1038 (2005).

Tian, Z. et al., A fully automatic multi-atlas based segmentation method for prostate MR images, Proc SPIE Int Soc Opt Eng. Author manuscript, 12 pages (2015).

Tian, Z. et al., A supervoxel-based segmentation method for prostate MR images, Med. Phys., 44(2):558-569 (2017).

Tian, Z. et al., Deep convolutional neural network for prostate MR segmentation, Proc. of SPIE 10135:101351L-1-101351L-6 12 pages, (2017).

Tian, Z., et al., Superpixel-based Segmentation for 3D Prostate MR Images, IEEE Trans Med Imaging, Author manuscript, pp. 558-569, (2016).

Trägårdh, E., et. al., RECOMIA—a cloud-based platform for artificial intelligence research in nuclear medicine and radiology, EJNMMI Physics, <https://doi.org/10.1186/s40658-020-00316-9>, 7:51, 12 pages, (2020).

Ulmert, D. et al., A Novel Automated Platform for Quantifying the Extent of Skeletal Tumour Involvement in Prostate Cancer Patients Using the Bone Scan Index, European Urology, 62(1):78-84 (2012).

Wallis, J.W. et. al., Three-dimensional display in nuclear medicine, IEEE Trans Med Imaging, 8(4):297-303, (1989).

Wrangsjo, A. et al., Non-rigid Registration Using Morphons, Proceedings of the 14th Scandinavian Conference on Image Analysis (SCIA '05), pp. 501-510 (2005).

Written Opinion for PCT/US2020/029435, filed Apr. 23, 2020, 15 pages, (dated Jul. 16, 2020).

Yin, T.-K., and Chiu, N.T., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

Inoue, T., What cancers can be understood and not known by "PET"?—Effects of PET scanning by site, Medical Note Interview, 4 pages, (2015), retrieved from the internet at: https://medicalnote.jp/contents/150715-000003-CYJIZE.

Kawakami, K. et al., Introduction of bone scintigraphy diagnosis support software "BONENAVI" (Topics), Journal of Nuclear Medicine (Japanese), 63:41-51 (2011).

Kawakami, K., Evaluation of bone metastasis by bone scintigraphy diagnostic support software BONENAVI, Communication of the Imaging Group of the JSRT, 36(1):74-77 (2013).

Nogi, S. et al., Metastatic bone tumor quantified by computer-assisted diagnosis system of bone scintigraphy, Nuclear Medicine in Clinic, 45(3):35-37 (2012).

Washino, H., Injectable for bone scintigraphy: Technetium hydroxymethylenediphosphonate (99mTc) injection solution (Revised Edition), 9 pages, (2007), retrieved from the internet at:https://rada.or.jp/database/home4/normal/ht-docs/member/synopsis/030292.html#:%7E:text=%E6%A6%82%E8%A6%81).

Gafita, A. et al., Novel Framework for Treatment Response Evaluation Using PSMA PET/CT in Patients with Metastatic Castration-Resistant Prostate Cancer (RECIP 1.0): An International Multicenter Study, J. Nucl. Med., 63(11):1651-1658 (2022).

Guan, H. et al., Automatic Hot Spot Detection and Segmentation in Whole Body FDG-PET Images, IEEE International Conference on Image Processing, 4 pages, (2006).

Partin, A.W. et al., Combination of prostate-specific antigen, clinical stage, and Gleason score to predict pathological stage of localized prostate cancer. A multi-institutional update, JAMA, 277(18):1445-1451 (1997).

Partin, A.W. et al., The use of prostate specific antigen, clinical stage and Gleason score to predict pathological stage in men with localized prostate cancer, J. Urol., 150(1):110-114 (1993).

Poulakis, V. et al., Preoperative neural network using combined magnetic resonance imaging variables, prostate specific antigen, and Gleason score to predict prostate cancer recurrence after radical prostatectomy, Eur. Urol., 46(5):571-578 (2004).

Seifert, R. et al., Second Version of the Prostate Cancer Molecular Imaging Standardized Evaluation Framework Including Response Evaluation for Clinical Trials (Promise V2), Eur. Urol., 83(5):405-412 (2023).

US Food and Drug Administration, Clinical Trial Endpoints for the Approval of Cancer Drugs and Biologics, 21 pages, (2018).

\* cited by examiner

FIG. 2

+ Add patient    ↻ Refresh patient list    ⇩ Export CSV

Filter list _____

| | PATIENT NAME | PATIENT ID | | | | STUDY DATE |
|---|---|---|---|---|---|---|
| ☐ | Patient006 | 006 | | | | |
| ☐ | Patient013 | 013 | △ | | | |
| ☐ | Patient005 | 005 | | 🗐 | | |
| ☐ | Patient001 | 001 | | | ⏱ | |
| ☐ | Patient004 | 004 | | | | |
| ☐ | Patient003 | 003 | | | | |

[START PATIENT ⊕]　[DELETE PATIENT]

Name: Patient001
ID: 001
Date of birth:

STUDIES    STATUS    REPORT
△
◯
◯     🗐

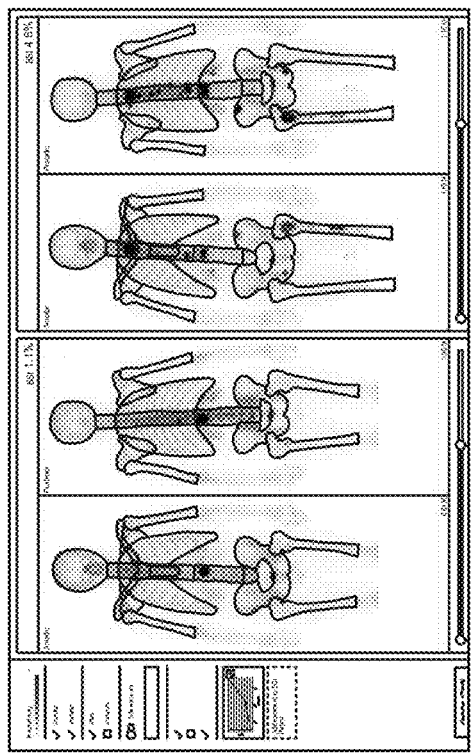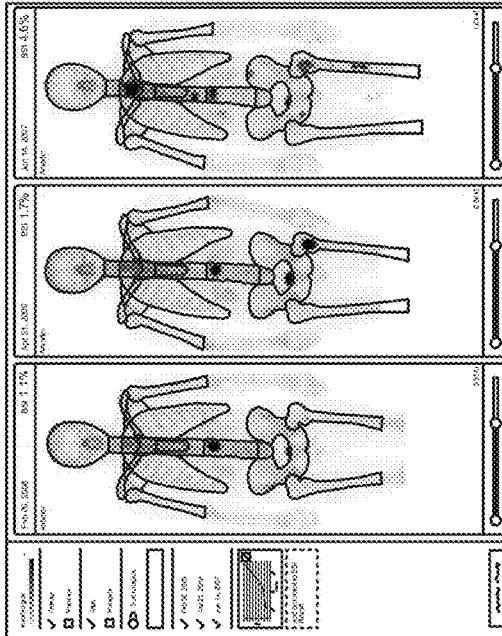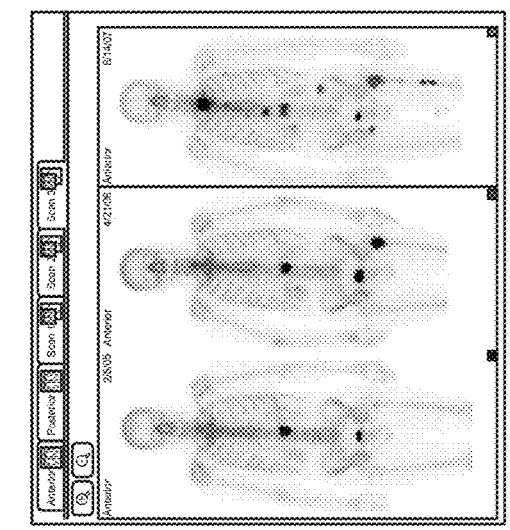
FIG. 14A  FIG. 14B  FIG. 14C  FIG. 14D

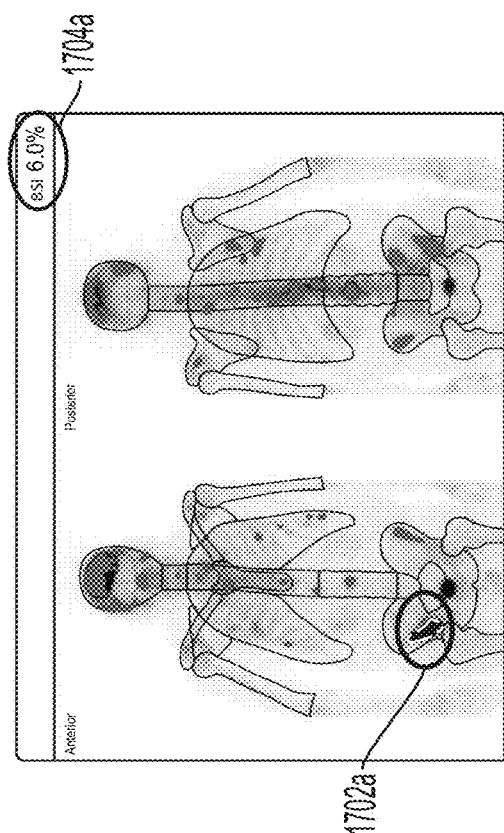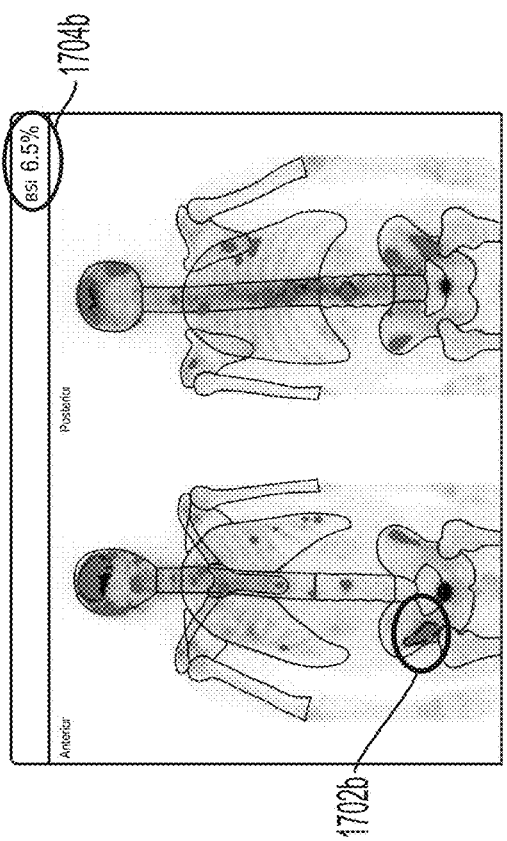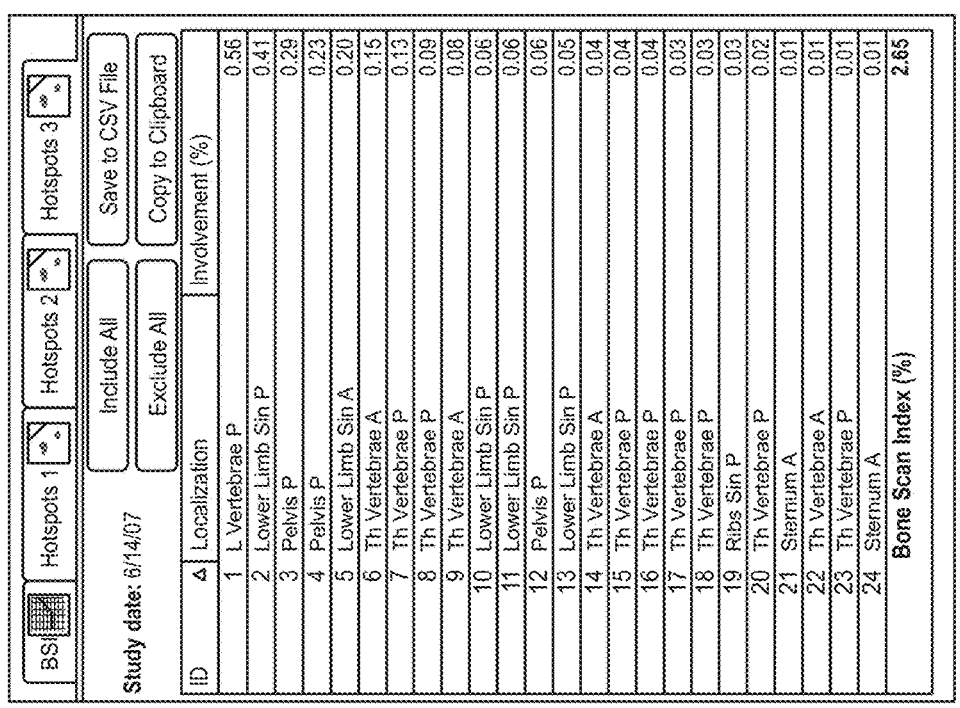
FIG. 17B
FIG. 17C
FIG. 17A

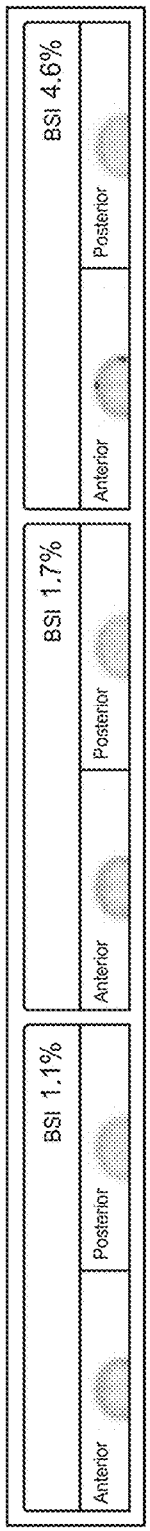
FIG. 19A
FIG. 19B
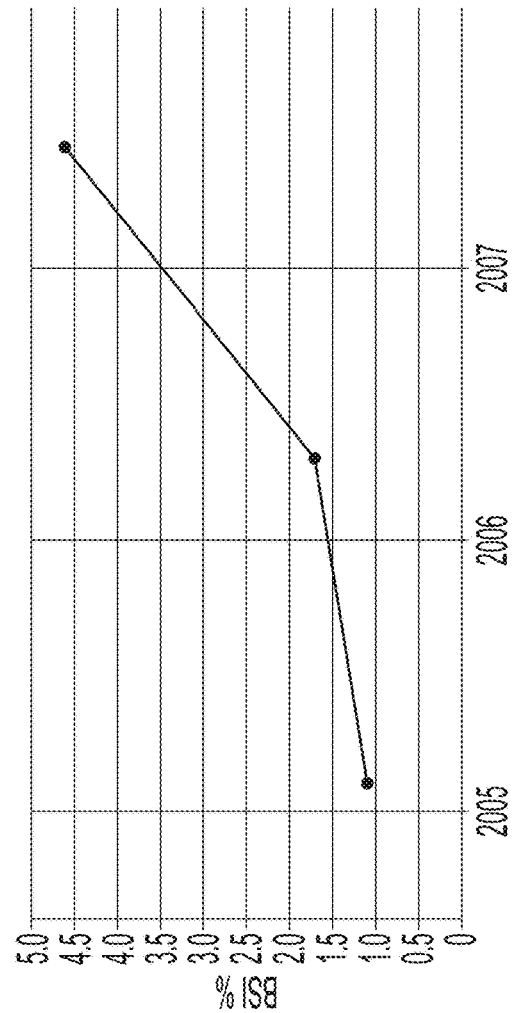
FIG. 20B
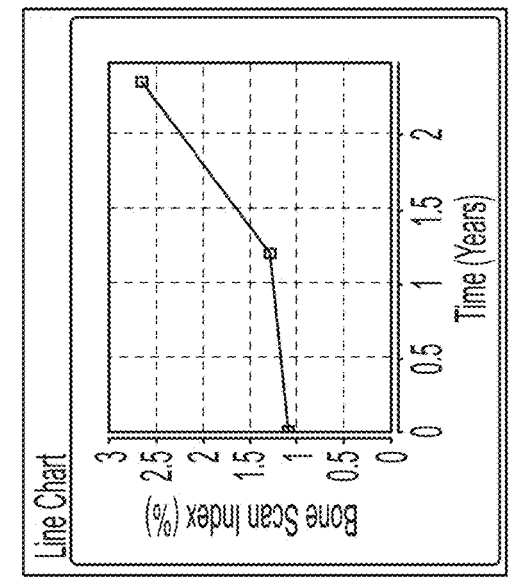
FIG. 20A

Involvement (%)
| Localization | 2/8/05 | 4/21/06 | 6/14/07 |
|---|---|---|---|
| Skull | - | 0.02 | - |
| Cervical Vertebrae | - | 0.04 | - |
| Thoracic Vertebrae | 0.04 | 0.03 | 0.68 |
| Lumbar Vertebrae | 0.83 | 0.57 | 0.56 |
| Upper Limb | - | - | - |
| Lower Limb | - | 0.34 | 0.78 |
| Thorax | - | - | 0.05 |
| Pelvis | 0.22 | 0.22 | 0.58 |
Included Hotspots
| Localization | 2/8/05 | 4/21/06 | 6/14/07 |
|---|---|---|---|
| Skull | 0 | 0 | 0 |
| Cervical Vertebrae | 0 | 1 | 0 |
| Thoracic Vertebrae | 1 | 4 | 12 |
| Lumbar Vertebrae | 8 | 4 | 1 |
| Upper Limb | 0 | 0 | 0 |
| Lower Limb | 1 | 0 | 5 |
| Thorax | 0 | 3 | 3 |
| Pelvis | 0 | 0 | 3 |
FIG. 21
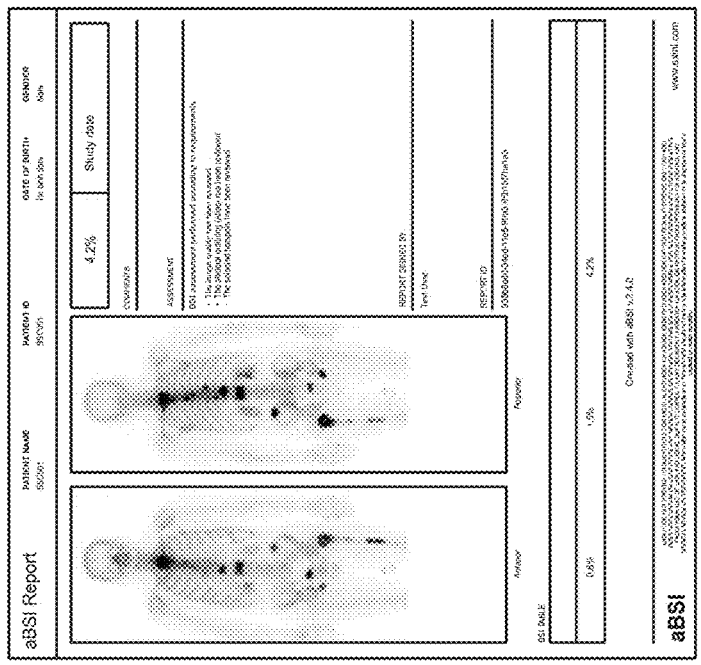
FIG. 22B
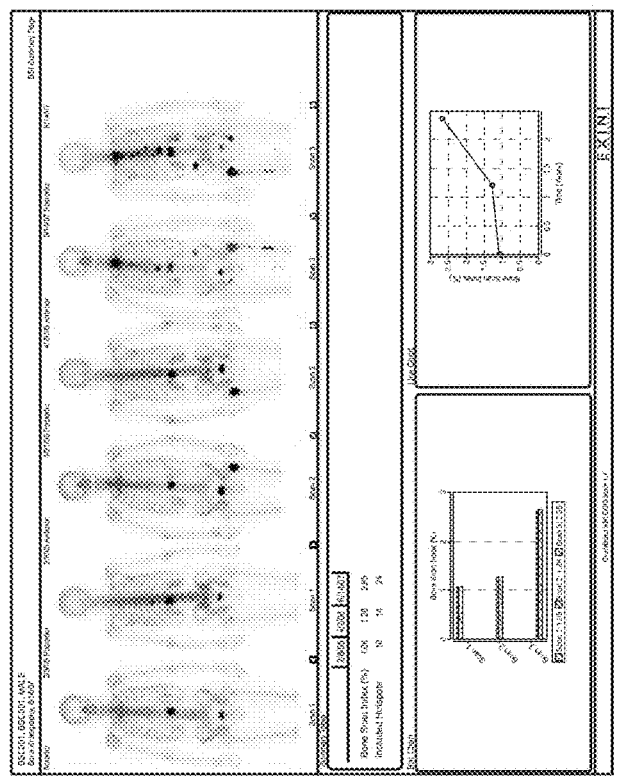
FIG. 22A

US 11,937,962 B2

SYSTEMS AND METHODS FOR AUTOMATED AND INTERACTIVE ANALYSIS OF BONE SCAN IMAGES FOR DETECTION OF METASTASES

CROSS-REFERENCE TO RELATED APPLICATION

This application is a continuation of U.S. application Ser. No. 16/856,120, filed Apr. 23, 2020 and patented as U.S. Pat. No. 11,534,125, which claims priority to and benefit of U.S. Provisional Application 62/837,955, filed Apr. 24, 2019, the content of which is hereby incorporated by reference in its entirety.

TECHNICAL FIELD

This invention relates generally to systems and methods for creation, analysis, and/or presentation of medical image data. More particularly, in certain embodiments, the invention relates to systems and methods for improved computer-aided display and analysis of nuclear medicine images

BACKGROUND

Nuclear medicine imaging involves the use of radiolabeled compounds, referred to as radiopharmaceuticals. Radiopharmaceuticals are administered to patients and accumulate in various regions in the body in manner that depends on, and is therefore indicative of, biophysical and/or biochemical properties of tissue therein, such as those influenced by presence and/or state of disease, such as cancer. For example, certain radiopharmaceuticals, following administration to a patient, accumulate in regions of abnormal osteogenesis associated with malignant bone lesions, which are indicative of metastases. Other radiopharmaceuticals may bind to specific receptors, enzymes, and proteins in the body that are altered during evolution of disease. After administration to a patient, these molecules circulate in the blood until they find their intended target. The bound radiopharmaceutical remains at the site of disease, while the rest of the agent clears from the body.

Nuclear medicine imaging techniques capture images by detecting radiation emitted from the radioactive portion of the radiopharmaceutical. The accumulated radiopharmaceutical serves as a beacon so that an image may be obtained depicting the disease location and concentration using commonly available nuclear medicine modalities. Examples of nuclear medicine imaging modalities include bone scan imaging (also referred to as scintigraphy), single-photon emission computerized tomography (SPECT), and positron emission tomography (PET). Bone scan, SPECT, and PET imaging systems are found in most hospitals throughout the world. Choice of a particular imaging modality depends on and/or dictates the particular radiopharmaceutical used. For example, technetium 99m ($^{99m}$Tc) labeled compounds are compatible with bone scan imaging and SPECT imaging, while PET imaging often uses fluorinated compounds labeled with 18F. The compound $^{99m}$Tc methylenediphosphonate ($^{99m}$Tc MDP) is a popular radiopharmaceutical used for bone scan imaging in order to detect metastatic cancer. Radiolabeled prostate-specific membrane antigen (PSMA) targeting compounds such as $^{99m}$Tc labeled 1404 and PyL™ (also referred to as [18F]DCFPyL) can be used with SPECT and PET imaging, respectively, and offer the potential for highly specific prostate cancer detection.

Accordingly, nuclear medicine imaging is a valuable technique for providing physicians with information that can be used to determine the presence and the extent of disease in a patient. The physician can use this information to provide a recommended course of treatment to the patient and to track the progression of disease.

For example, an oncologist may use nuclear medicine images from a study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the nuclear medicine images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results. If an imaging study shows that the patient has a particular disease or condition (e.g., cancer), the physician discusses various treatment options, including surgery, as well as risks of doing nothing or adopting a watchful waiting or active surveillance approach, rather than having surgery.

Accordingly, the process of reviewing and analyzing multiple patient images, over time, plays a critical role in the diagnosis and treatment of cancer. There is, thus, a significant need for improved tools that facilitate and improve accuracy of image review and analysis for cancer diagnosis and treatment. Improving the toolkit utilized by physicians, radiologists, and other healthcare professionals in this manner provides for significant improvements in standard of care and patient experience.

SUMMARY OF THE INVENTION

Presented herein are systems and methods that provide for improved computer aided display and analysis of nuclear medicine images. In particular, in certain embodiments, the systems and methods described herein provide improvements to several image processing steps used for automated analysis of bone scan images for assessing cancer status of a patient.

For example, improved approaches for image segmentation, hotspot detection, automated classification of hotspots as representing metastases, and computation of risk indices such as bone scan index (BSI) values are provided. By virtue of these improved image processing techniques, the systems and methods described herein can be used for accurate and reliable image-based lesion detection and quantification for assessment of various metastatic bone cancers (e.g., any cancer having metastasized to the bone). These include metastases associated with prostate cancer, breast cancer, lung cancer, and various other metastatic cancers.

Bone scan images are widely used for diagnosing and evaluating metastatic cancer. Patients are injected with radiopharmaceutical that emits nuclear radiation, which can be detected to image the spatial distribution of the radiopharmaceutical within the patient. Radiopharmaceuticals can be chosen to selectively accumulate in types of tissue associated with cancerous lesions, such as regions of abnormal osteogenesis.

While this approach allows lesions to be visualized as bright spots in bone scan images, accurately identifying image regions representing true metastatic lesions is by no means straightforward. Radiopharmaceutical may accumulate in non-cancerous anatomical regions as well, such as in a patient's bladder, and physicians and technicians must carefully distinguish hotspots representing lesions from these regions, as well as from noise and artifacts. This work is time-consuming, error prone, and subject to significant inter-operator variability.

Computer automated lesion detection and analysis offers a route to addressing these challenges and can dramatically increase accuracy and repeatability of lesion detection and cancer diagnostics. Tools for automated lesion detection and analysis, however, rely on a complex combination of imaging processing and artificial intelligence steps. For example, image segmentation to identify skeletal regions may be used to focus analysis to bone regions. Filtering and thresholding steps can be used to automatically detect hotspots, and machine learning approaches, such as artificial neural networks (ANNs), may be used to quantitatively assess the likelihood that a detected hotspot represents a metastasis, based on features such as size, shape, and intensity of hotspots. Finally, in certain embodiments, a set of detected hotspots representing metastases is used to compute an overall risk index for the patient, representing an overall likelihood of the patient having and/or developing metastases or having a particular cancer state. One such risk index is bone scan index (BSI), which provides an estimated mass fraction of the patient's skeleton occupied by metastases.

The accuracy of any one step can have a significant impact on downstream steps and the overall lesion detection and analysis process. The systems and methods described herein provide several specific improvements to various steps in the automated lesion detection and analysis workflow, thereby increasing accuracy of results over a wider range of patient types and cancer stages.

First, in certain embodiments, the improved image analysis techniques described herein include an improved skeletal segmentation approach in which entire (e.g., more than three-quarters length) humerus and/or femur region(s) are identified in bone scan images. Previous approaches only identified a limited fraction of femur and humerus bones. Here, segmenting a larger portion of these bones allows lesions located further out in the extremities of the arms and legs to be identified, whereas previously such lesions would have escaped detection. Moreover, while reduced radiopharmaceutical uptake in arms and legs makes lesion identification therein challenging, the approaches described herein utilize a region dependent thresholding technique that enhances detection sensitivity in femur and humerus bone regions to overcome this issue.

Second, the present disclosure also provides a global thresholding technique that improves hotspot detection accuracy, particularly at high disease burdens (e.g., when a patient has many lesions). This approach detects a preliminary set of potential hotspots, and then adjusts thresholds used for hotspot detection based on a scaling factor computed from this preliminary set. The improvement in hotspot detection provides advantages for downstream calculations, improving linearity of computed BSI values for patients with high levels of metastases.

Third, in certain embodiments, the systems and methods described herein improve the accuracy with which automated decisions about whether a hotspot represents a metastasis are made. In particular, in certain embodiments, the approaches described herein leverage clinical experience indicating that hotspots selection as potential metastases depends not only on the image features of the hotspot itself, but also information from the entire image. Accordingly, the approaches described herein may also use global features, for example a total number of hotspots, as input in automated decision making steps (e.g., as input to ANNs) for lesion identification.

Fourth, in certain embodiments, the approaches described herein also offer improvements to approaches for calculating risk index values based on skeletal involvement, by employing correction factors that account for potential errors in the accuracy with which hotspots can be automatically localized to a particular skeletal region. This is particularly important for hotspots located in or near the sacrum region, which is a complex three dimensional structure that may be difficult to identify in two-dimensional bone scan images. This approach improves accuracy of BSI calculations, and limits sensitivity to errors in hotspot localization.

Accordingly, the systems and methods described herein include several improved image analysis techniques for lesion identification and quantification. These approaches improve accuracy and robustness with which bone scan images can be analyzed. As described herein, they can be used as part of a cloud-based system that facilitates review and reporting of patient data, and allow for improved disease detection, treatment, and monitoring.

In one aspect, the invention is directed to a method for lesion marking and quantitative analysis (e.g., user assisted/reviewed automated or semi-automated lesion marking and quantitative analysis) of nuclear medicine images (e.g., a bone scan image set) of a human subject, the method comprising: (a) accessing (e.g., and/or receiving), by a processor of a computing device, a bone scan image set (e.g., a set of one, two, or more images) for the human subject, said bone scan image set obtained following administration of an agent (e.g. a radiopharmaceutical) to the human subject (e.g., the bone scan image set comprising an anterior bone scan image and a posterior bone scan image)(e.g., wherein each image of the bone scan image set comprises a plurality of pixels, each pixel having a value corresponding to an intensity); (b) automatically segmenting, by the processor, each image in the bone scan image set to identify one or more skeletal regions of interest, each corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images, wherein the one or more skeletal regions of interest comprise at least one of (i) and (ii): (i) a femur region corresponding to a portion of a femur of the human subject, said femur portion encompassing at least three quarters [(e.g., greater than about three quarters (e.g., approximately all)] of the femur along its length; and (ii) a humerus region corresponding to a portion of a humerus of the human subject, said humerus portion encompassing at least three quarters [(e.g., greater than about three quarters (e.g., approximately all)] of the humerus along its length; (c) automatically detecting, by the processor, an initial set of one or more hotspots, each hotspot corresponding to an area of elevated intensity in the annotated set of images, said automatically detecting comprising identifying the one or more hotspots using intensities of pixels in the annotated set of images and using one or more region-dependent threshold values (e.g., wherein each region-dependent threshold value is associated with an identified skeletal region of interest, such that intensities of pixels located within a particular identified skeletal region are compared with the associated region-dependent threshold value), and wherein the one or more region dependent threshold values include one or more values associated with the femur region and/or the humerus region (e.g., a reduced intensity threshold for the femur region and/or a reduced intensity threshold for the humerus region) that provide enhanced hotspot detection sensitivity in the femur region and/or the humerus region to compensate for reduced uptake of the agent therein; (d) for each hotspot in the initial set of hotspots, extracting, by the processor, a set of (e.g., a set of one or more) hotspot features associated with the hotspot; (e) for each hotspot in the initial set of hotspots, calculating, by the processor, a metastasis likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input and output the metastasis likelihood value for that hotspot]; and (f) causing, by the processor, rendering of a graphical representation of at least a portion of the initial set of hotspots [e.g., a visual indication (e.g., points, boundaries) of hotspots overlaid on one or more members of the bone scan image set and/or annotated set of images; e.g., a table listing identified hotspots along with additional information (e.g., location; e.g., metastasis likelihood value) for each hotspot] for display within a graphical user interface (GUI) (e.g., a cloud-based GUI).

In certain embodiments, step (b) comprises: comparing each member of the bone scan image set with a corresponding atlas image of an atlas image set, each atlas image comprising one or more identifications of the one or more skeletal regions of interest (e.g., graphical identifications superimposed on the atlas image), said skeletal regions of interest including the femur region and/or the humerus region; and for each image of the bone scan image set, registering the corresponding atlas image with the image of the bone scan image set, such that the identifications of the one or more skeletal regions of interest of the atlas image are applied to (e.g., are superimposed on) the image of the bone scan image set.

In certain embodiments, each atlas image comprises an identification of (i) the femur region comprising at least a portion of a knee region of the human subject and/or (ii) the humerus region comprising at least a portion of an elbow region of the human subject, and wherein, for each image of the bone scan image set, the registering of the corresponding atlas image to the bone scan image comprises using the identified knee region and/or the identified elbow region in the image as (a) landmark(s) [e.g., registering the corresponding atlas image to the bone scan image by identifying a knee region in the bone scan image and matching it to the identified knee region in the corresponding atlas image, then adjusting the atlas image (e.g., calculating a coordinate transform)].

In certain embodiments, a location of at least one detected hotspot of the initial hotspot set corresponds to a physical location in or on a femur more than three quarters of a distance along the femur from an end of the femur oriented toward a hip of the human subject to an end of the femur oriented toward a knee of the human subject.

In certain embodiments, a location of at least one detected hotspot of the initial hotspot set corresponds to a physical location in or on a humerus more than three quarters of a distance along the humerus from an end of the humerus oriented toward a shoulder of the human subject to an end of the humerus oriented toward an elbow of the human subject.

In certain embodiments, step (c) comprises (e.g., iteratively): identifying, by the processor, healthy tissue regions in the images of the bone scan image set determined not to include any hotspots (e.g., localized regions of relatively high intensity); calculating, by the processor, a normalization factor such that a product of the normalization factor and an average intensity of the identified healthy tissue regions is a pre-defined intensity level; and normalizing the images of the bone scan image set by the normalization factor.

In certain embodiments, the method further comprises: (g) calculating, by the processor, one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the method comprises: (h) selecting, by the processor, a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value)]; and (i) causing, by the processor, rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the method further comprises: (j) calculating, by the processor, one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the method comprises: (k) receiving, by the processor, via the GUI, a user selection of a second subset of the initial set of hotspots; and (l) calculating, by the processor, one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a method for lesion marking and quantitative analysis (e.g., user assisted/ reviewed automated or semi-automated lesion marking and quantitative analysis) of nuclear medicine images (e.g., a bone scan image set) of a human subject, the method comprising: (a) accessing (e.g., and/or receiving), by a processor of a computing device, a bone scan image set (e.g., a set of one, two, or more images) for the human subject, said bone scan image set obtained following administration of an agent (e.g., a radiopharmaceutical) to the human subject (e.g., the bone scan image set comprising an anterior bone scan image and a posterior bone scan image) (e.g., wherein each image of the bone scan image set comprises a plurality of pixels, each pixel having a value corresponding to an intensity); (b) automatically segmenting, by the processor, each image in the bone scan image set to identify one or more skeletal regions of interest, each skeletal region of interest corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images; (c) automatically detecting, by the processor, an initial set of one or more hotspots, each hotspot corresponding to an area of elevated intensity in the annotated set of images, said automatically detecting comprising: using (i) intensities of pixels in the annotated set of images and (ii) a plurality of preliminary threshold values (e.g., wherein the plurality of preliminary threshold values are region-dependent threshold values that depend on the identified skeletal region of interest in which particular pixel(s) is/are located) to detect a set of potential hotspots; computing a global threshold scaling factor using the set of potential hotspots; adjusting the plurality of preliminary threshold values using the global threshold scaling factor, thereby obtaining a plurality of adjusted threshold values; and using (i) intensities of pixels in the annotated set of images and (ii) the plurality of adjusted threshold values to identify the initial set of hotspots; (d) for each hotspot in the initial set of hotspots, extracting, by the processor, a set of (e.g., a set of one or more) hotspot features associated with the hotspot; (e) for each hotspot in the initial set of hotspots, calculating, by the processor, a metastasis likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input, and output the metastasis likelihood value for that hotspot]; and (f) causing, by the processor, rendering of a graphical representation of at least a portion of the initial set of hotspots [e.g., a visual indication (e.g., points, boundaries) of hotspots overlaid on one or more images of the bone scan image set and/or annotated set of images; e.g., a table listing identified hotspots along with additional information (e.g., location; e.g., metastasis likelihood value) for each hotspot] for display within a graphical user interface (GUI) (e.g., a cloud-based GUI).

In certain embodiments, the global threshold scaling factor is a function of a measure of disease burden for the human subject [e.g., an area fraction of the skeleton of the subject occupied by metastases (e.g., hotspots); e.g., a risk index value], and wherein the adjusting the plurality of preliminary threshold values performed at step (c) comprises decreasing the adjusted threshold values (e.g., with respect to the preliminary threshold values) as disease burden increases (e.g., as measured by the global threshold scaling factor) so as to compensate for an underestimation of hotspot area that occurs with increasing disease burden (e.g., such that a total number and/or size of hotspots increases with the decreased adjusted threshold values).

In certain embodiments, the global threshold scaling factor is a function (e.g., a non-linear function) of a fraction (e.g., an area fraction) of the identified skeletal regions occupied by the set of potential hotspot set (e.g., wherein the global threshold scaling factor is a function of a total area of all hotspots in the preliminary set, divided by a total area of all identified skeletal regions).

In certain embodiments, the global threshold scaling factor is based on (e.g., computed as a function of) a risk index value calculated using the set of potential hotspots.

In certain embodiments, step (c) comprises (e.g., iteratively): identifying, by the processor, healthy tissue regions in the images of the bone scan image set determined not to include any hotspots (e.g., localized regions of relatively high intensity); calculating, by the processor, a normalization factor such that a product of the normalization factor and an average intensity of the identified healthy tissue regions is a pre-defined intensity level; and normalizing, by the processor, the images of the bone scan image set by the normalization factor.

In certain embodiments, the method further comprises: (g) calculating, by the processor, one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the method comprises: (h) selecting, by the processor, a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value]; and (i) causing, by the processor, rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the method further comprises: (j) calculating, by the processor, one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the method comprises: (k) receiving, by the processor, via the GUI, a user selection of a second subset of the initial set of hotspots; and (l) calculating, by the processor, one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a method for lesion marking and quantitative analysis (e.g., user assisted/reviewed automated or semi-automated lesion marking and quantitative analysis) of nuclear medicine images (e.g., a bone scan image set) of a human subject, the method comprising: (a) accessing (e.g., and/or receiving), by a processor of a computing device, a bone scan image set (e.g., a set of one, two, or more images) for the human subject, said bone scan image set obtained following administration of an agent (e.g., a radiopharmaceutical) to the human subject (e.g., the bone scan image set comprising an anterior bone scan image and a posterior bone scan image)(e.g., wherein each image of the bone scan image set comprises a plurality of pixels, each pixel having a value corresponding to an intensity); (b) automatically segmenting, by the processor, each image in the bone scan image set to identify one or more skeletal regions of interest, each skeletal region of interest corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images; (c) automatically detecting, by the processor, an initial set of one or more hotspots, each hotspot corresponding to an area of elevated intensity in the annotated set of images [e.g., wherein detecting the one or more hotspots of the initial hotspot set comprises comparing pixel intensities with one or more threshold values (e.g., wherein the one or more threshold values vary depending on the identified skeletal region of interest in which a particular pixel is located)]; (d) for each hotspot in the initial set of hotspots, extracting, by the processor, a set of (e.g., a set of one or more) hotspot features associated with the hotspot; (e) for each hotspot in the initial set of hotspots, calculating, by the processor, a metastasis likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input and output the metastasis likelihood value for that hotspot]; (f) selecting, by the processor, a first subset (e.g., up to all) of the initial set of hotspots, wherein selection of a particular hotspot for inclusion in in the first subset is based at least in part on: (i) the metastasis likelihood value calculated for the particular hotspot [e.g., based on comparison of the likelihood value calculated for the particular hotspot with a likelihood threshold value (e.g., including the particular hotspot in the first subset if it has a likelihood value greater than the likelihood threshold value)]; and (ii) one or more global hotspot features, each global hotspot feature determined using a plurality of hotspots in the initial set of hotspots (e.g., a total number of hotspots in the initial hotspot set, an average intensity of hotspots in the initial hotspot set, a peak intensity of hotspots in the initial hotspot set, etc.); and (g) causing, by the processor, rendering of a graphical representation of at least a portion of the first subset of hotspots [e.g., a visual indication (e.g., points, boundaries) of hotspots overlaid on one or more images of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the one or more global hotspot features comprises a total number of hotspots in the initial hotspot set.

In certain embodiments, step (f) comprises adjusting criteria for selection of hotspots for inclusion in the first subset based on the total number of hotspots in the initial hotspot set [e.g., by relaxing criteria as the total number of hotspots in the initial hotspot set increases (e.g., by reducing a metastasis likelihood threshold to which each hotspots metastasis likelihood value is compared; e.g., by scaling metastasis likelihood values based on the total number of hotspots in the initial hotspot set)].

In certain embodiments, step (f) comprises using a machine learning module to select the first subset (e.g., an ANN module)[e.g., wherein the machine learning module receives, for each hotspot, at least the metastasis likelihood value calculated for the hotspot and the one or more global hotspot features and outputs (i) an adjusted metastasis likelihood value that takes into account the global hotspot features (e.g., a value on a scale that can be compared to a threshold for selection of the hotspot in the first subset) and/or (ii) a binary (e.g., 0 or 1; e.g., Boolean True or False) value representing whether the hotspot should or should not be included in the first subset].

In certain embodiments, step (c) comprises (e.g., iteratively): identifying, by the processor, healthy tissue regions in the images of the bone scan image set determined not to include any hotspots (e.g., localized regions of relatively high intensity); calculating, by the processor, a normalization factor such that a product of the normalization factor and an average intensity of the identified healthy tissue regions is a pre-defined intensity level; and normalizing, by the processor, the images of the bone scan image set by the normalization factor.

In certain embodiments, the method further comprises: (g) calculating, by the processor, one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the method comprises: (h) selecting, by the processor, a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value)]; and (i) causing, by the processor, rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the method further comprises: (j) calculating, by the processor, one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the method comprises: (k) receiving, by the processor, via the GUI, a user selection of a second subset of the initial set of hotspots; and (l) calculating, by the processor, one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a method for lesion marking and quantitative analysis (e.g., user assisted/reviewed automated or semi-automated lesion marking and quantitative analysis) of nuclear medicine images (e.g., a bone scan image set) of a human subject, the method comprising: (a) accessing (e.g., and/or receiving), by a processor of a computing device, a bone scan image set (e.g., a set of one, two, or more images) for the human subject (e.g., the bone scan image set comprising an anterior bone scan image and a posterior bone scan image)(e.g., wherein each image of the bone scan image set comprises a plurality of pixels, each pixel having a value corresponding to an intensity); (b) automatically segmenting, by the processor, each image in the bone scan image set to identify one or more skeletal regions of interest, each skeletal region of interest corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images; (c) automatically detecting, by the processor, an initial set of one or more hotspots, each hotspot corresponding to an area of elevated intensity in the annotated set of images [e.g., wherein detecting the one or more hotspots of the initial hotspot set comprises comparing pixel intensities with one or more threshold values (e.g., wherein the one or more threshold values vary depending on the identified skeletal region of interest in which a particular pixel is located)]; (d) for each hotspot in the initial set of hotspots, extracting, by the processor, a set of (e.g., a set of one or more) hotspot features associated with the hotspot; (e) for each hotspot in the initial set of hotspots, calculating, by the processor, a likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input and output the likelihood value for that hotspot]; (f) selecting, by the processor, a first subset (e.g., up to all) of the hotspots of the initial set of hotspots based at least in part on the likelihood values calculated for each hotspot of the initial set of hotspots [e.g., by determining whether or not to include a particular hotspot of the initial set of hotspots in the set of pre-selected hotspots based on the likelihood value calculated for that particular hotspot (e.g., by comparing it with a likelihood threshold value)]; and (g) calculating, by the processor, one or more risk index values (e.g., a bone scan index value) using at least a portion (e.g., up to all) of the first subset of hotspots, said calculating comprising: computing, for each particular hotspot of the portion of first subset, a skeletal involvement factor based on a ratio of (i) a size (e.g., area) of the particular hotspot to (ii) a size (e.g., area) of a particular skeletal region to which the particular hotspot is assigned (e.g., by the processor) based on its location in the annotated set of images, thereby determining one or more skeletal involvement factors; adjusting the skeletal involvement factors using one or more region-dependent correction factors [e.g., each region-dependent correction factor associated with one or more skeletal regions; e.g., wherein the region-dependent correction factors have values selected to reduce a degree to which assigning a particular hotspot to a specific skeletal region (e.g., of a plurality of neighboring or nearby skeletal regions, such as sacrum, pelvic, and lumbar regions) causes fluctuations in computed skeletal involvement factors], thereby obtaining one or more adjusted skeletal involvement factors; and summing the adjusted skeletal involvement factors to determine the one or more risk index values.

In certain embodiments, for each particular hotspot, the computed skeletal involvement factor estimates a proportion of total skeletal mass occupied by a physical volume associated with the particular hotspot.

In certain embodiments, the computing the skeletal involvement factor comprises: calculating, by the processor, a ratio of an area of the particular hotspot to an area of the corresponding skeletal region of interest, thereby computing an area fraction for the particular hotspot; and scaling (e.g., multiplying) the area fraction by a density coefficient associated with the skeletal region of interest to which the particular hotspot is assigned [e.g., that accounts for weight and/or density of bond in the corresponding skeletal region of interest (e.g., wherein the density coefficient is a weight fraction of the corresponding skeletal region of interest with respect to a total skeleton (e.g., of an average human)], thereby computing the skeletal involvement factor for the particular hotspot.

In certain embodiments, at least a portion of the hotspots of the first subset are assigned to a skeletal region of interest that is a member selected from the group consisting of a pelvis region (e.g., corresponding to a pelvis of the human subject), a lumbar region (e.g., corresponding to a lumbar column of the human subject), and a sacrum region (e.g., corresponding to a sacrum of the human subject).

In certain embodiments, the one or more region-dependent correction factors comprise a sacrum region correction factor associated with a sacrum region and used to adjust skeletal involvement factors of hotspots identified (e.g., by the processor) as being located therein, and wherein the sacrum region correction factor has a value less than one (e.g., less than 0.5).

In certain embodiments, the one or more region dependent correction factors comprise one or more correction factor pairs, each correction factor pair associated with a specific skeletal region of interest and comprising a first member and a second member (of the pair), wherein: the first member of the pair is an anterior image correction factor and is used to adjust skeletal involvement factors computed for hotspots having been detected in an annotated anterior bone scan image of the annotated image set, and the second member of the pair is a posterior image correction factor and is used to adjust skeletal involvement factors computed for hotspots having been detected in an annotated posterior bone scan image of the annotated image set.

In certain embodiments, step (c) comprises (e.g., iteratively): identifying, by the processor, healthy tissue regions in the images of the bone scan image set determined not to include any hotspots (e.g., localized regions of relatively high intensity); calculating, by the processor, a normalization factor such that a product of the normalization factor and an average intensity of the identified healthy tissue regions is a pre-defined intensity level; and normalizing, by the processor, the images of the bone scan image set by the normalization factor.

In certain embodiments, the method further comprises: (g) calculating, by the processor, one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the method comprises: (h) selecting, by the processor, a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value)]; and (i) causing, by the processor, rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the method further comprises: (j) calculating, by the processor, one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the method comprises: (k) receiving, by the processor, via the GUI, a user selection of a second subset of the initial set of hotspots; and (l) calculating, by the processor, one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a system for lesion marking and quantitative analysis (e.g., user assisted/reviewed automated or semi-automated lesion marking and quantitative analysis) of nuclear medicine images (e.g., a bone scan image set) of a human subject, the system comprising: a processor; and a memory having instructions thereon, wherein the instructions, when executed by the processor, cause the processor to: (a) access (e.g., and/or receive) a bone scan image set (e.g., a set of one, two, or more images) for the human subject, said bone scan image set obtained following administration of an agent (e.g. a radiopharmaceutical) to the human subject (e.g., the bone scan image set comprising an anterior bone scan image and a posterior bone scan image)(e.g., wherein each image of the bone scan image set comprises a plurality of pixels, each pixel having a value corresponding to an intensity); (b) automatically segment each image in the bone scan image set to identify one or more skeletal regions of interest, each corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images, wherein the one or more skeletal regions of interest comprise at least one of (i) and (ii): (i) a femur region corresponding to a portion of a femur of the human subject, said femur portion encompassing at least three quarters [(e.g., greater than about three quarters (e.g., approximately all)] of the femur along its length; and (ii) a humerus region corresponding to a portion of a humerus of the human subject, said humerus portion encompassing at least three quarters [(e.g., greater than about three quarters (e.g., approximately all)] of the humerus along its length; (c) automatically detect an initial set of one or more hotspots, each hotspot corresponding to an area of elevated intensity in the annotated set of images, said automatically detecting comprising identifying the one or more hotspots using intensities of pixels in the annotated set of images and using one or more region-dependent threshold values (e.g., wherein each region-dependent threshold value is associated with an identified skeletal region of interest, such that intensities of pixels located within a particular identified skeletal region are compared with the associated region-dependent threshold value), and wherein the one or more region dependent threshold values include one or more values associated with the femur region and/or the humerus region (e.g., a reduced intensity threshold for the femur region and/or a reduced intensity threshold for the humerus region) that provide enhanced hotspot detection sensitivity in the femur region and/or the humerus region to compensate for reduced uptake of the agent therein; (d) for each hotspot in the initial set of hotspots, extract a set of (e.g., a set of one or more) hotspot features associated with the hotspot; (e) for each hotspot in the initial set of hotspots, calculate a metastasis likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input and output the metastasis likelihood value for that hotspot]; and (f) cause rendering of a graphical representation of at least a portion of the initial set of hotspots [e.g., a visual indication (e.g., points, boundaries) of hotspots overlaid on one or more members of the bone scan image set and/or annotated set of images; e.g., a table listing identified hotspots along with additional information (e.g., location; e.g., metastasis likelihood value) for each hotspot] for display within a graphical user interface (GUI) (e.g., a cloud-based GUI).

In certain embodiments, at step (b) the instructions cause the processor to: compare each member of the bone scan image set with a corresponding atlas image of an atlas image set, each atlas image comprising one or more identifications of the one or more skeletal regions of interest (e.g., graphical identifications superimposed on the atlas image), said skeletal regions of interest including the femur region and/or the humerus region; and for each image of the bone scan image set, register the corresponding atlas image with the image of the bone scan image set, such that the identifications of the one or more skeletal regions of interest of the atlas image are applied to (e.g., are superimposed on) the image of the bone scan image set.

In certain embodiments, each atlas image comprises an identification of (i) the femur region comprising at least a portion of a knee region of the human subject and/or (ii) the humerus region comprising at least a portion of an elbow region of the human subject, and wherein, for each image of the bone scan image set, the instructions cause the processor to register the corresponding atlas image to the bone scan image using the identified knee region and/or the identified elbow region in the image as (a) landmark(s) [e.g., registering the corresponding atlas image to the bone scan image by identifying a knee region in the bone scan image and matching it to the identified knee region in the corresponding atlas image, then adjusting the atlas image (e.g., calculating a coordinate transform)].

In certain embodiments, a location of at least one detected hotspot of the initial hotspot set corresponds to a physical location in or on a femur more than three quarters of a distance along the femur from an end of the femur oriented toward a hip of the human subject to an end of the femur oriented toward a knee of the human subject.

In certain embodiments, a location of at least one detected hotspot of the initial hotspot set corresponds to a physical location in or on a humerus more than three quarters of a distance along the humerus from an end of the humerus oriented toward a shoulder of the human subject to an end of the humerus oriented toward an elbow of the human subject.

In certain embodiments, at step (c) the instructions cause the processor to (e.g., iteratively): identify healthy tissue regions in the images of the bone scan image set determined not to include any hotspots (e.g., localized regions of relatively high intensity); calculate a normalization factor such that a product of the normalization factor and an average intensity of the identified healthy tissue regions is a predefined intensity level; and normalize the images of the bone scan image set by the normalization factor.

In certain embodiments, the instructions further cause the processor to: (g) calculate one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the instructions cause the processor to: (h) select a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value)]; and (i) cause rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the instructions cause the processor to: (j) calculate one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the instructions cause the processor to: (k) receive, via the GUI, a user selection of a second subset of the initial set of hotspots; and (l) calculate one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the system is a cloud based system. In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a system for lesion marking and quantitative analysis (e.g., user assisted/reviewed automated or semi-automated lesion marking and quantitative analysis) of nuclear medicine images (e.g., a bone scan image set) of a human subject, the system comprising: a processor; and a memory having instructions thereon, wherein the instructions, when executed by the processor, cause the processor to: (a) access (e.g., and/or receive), by a processor of a computing device, a bone scan image set (e.g., a set of one, two, or more images) for the human subject, said bone scan image set obtained following administration of an agent (e.g., a radiopharmaceutical) to the human subject (e.g., the bone scan image set comprising an anterior bone scan image and a posterior bone scan image)(e.g., wherein each image of the bone scan image set comprises a plurality of pixels, each pixel having a value corresponding to an intensity); (b) automatically segment each image in the bone scan image set to identify one or more skeletal regions of interest, each skeletal region of interest corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images; (c) automatically detect an initial set of one or more hotspots, each hotspot corresponding to an area of elevated intensity in the annotated set of images, said automatically detecting comprising: using (i) intensities of pixels in the annotated set of images and (ii) a plurality of preliminary threshold values (e.g., wherein the plurality of preliminary threshold values are region-dependent threshold values that depend on the identified skeletal region of interest in which particular pixel(s) is/are located) to detect a set of potential hotspots; computing a global threshold scaling factor using the set of potential hotspots; adjusting the plurality of preliminary threshold values using the global threshold scaling factor, thereby obtaining a plurality of adjusted threshold values; and using (i) intensities of pixels in the annotated set of images and (ii) the plurality of adjusted threshold values to identify the initial set of hotspots; (d) for each hotspot in the initial set of hotspots, extract a set of (e.g., a set of one or more) hotspot features associated with the hotspot; (e) for each hotspot in the initial set of hotspots, calculate a metastasis likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input, and output the metastasis likelihood value for that hotspot]; and (f) cause rendering of a graphical representation of at least a portion of the initial set of hotspots [e.g., a visual indication (e.g., points, boundaries) of hotspots overlaid on one or more images of the bone scan image set and/or annotated set of images; e.g., a table listing identified hotspots along with additional information (e.g., location; e.g., metastasis likelihood value) for each hotspot] for display within a graphical user interface (GUI) (e.g., a cloud-based GUI).

In certain embodiments, the instructions cause the processor to: compute the global threshold scaling factor a function of a measure of disease burden for the human subject [e.g., an area fraction of the skeleton of the subject occupied by metastases (e.g., hotspots); e.g., a risk index value]; and, at step (c) adjust the plurality of preliminary threshold values by decreasing the adjusted threshold values (e.g., with respect to the preliminary threshold values) as disease burden increases (e.g., as measured by the global threshold scaling factor) so as to compensate for an underestimation of hotspot area that occurs with increasing disease burden (e.g., such that a total number and/or size of hotspots increases with the decreased adjusted threshold values).

In certain embodiments, the instructions cause the processor to compute global threshold scaling factor as a function (e.g., a non-linear function) of a fraction (e.g., an area fraction) of the identified skeletal regions occupied by the set of potential hotspot set (e.g., wherein the global threshold scaling factor is a function of a total area of all hotspots in the preliminary set, divided by a total area of all identified skeletal regions).

In certain embodiments, the instructions cause the processor to compute the global threshold scaling factor based on (e.g., as a function of) a risk index value calculated using the set of potential hotspots.

In certain embodiments, at step (c) the instructions cause the processor to (e.g., iteratively): identify healthy tissue regions in the images of the bone scan image set determined not to include any hotspots (e.g., localized regions of relatively high intensity); calculate a normalization factor such that a product of the normalization factor and an average intensity of the identified healthy tissue regions is a predefined intensity level; and normalize the images of the bone scan image set by the normalization factor.

In certain embodiments, the instructions further cause the processor to: (g) calculate one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the instructions cause the processor to: (h) select a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value)]; and (i) cause rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the instructions cause the processor to: (j) calculate one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the instructions cause the processor to: (k) receive, via the GUI, a user selection of a second subset of the initial set of hotspots; and (l) calculate one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the system is a cloud based system. In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a system for lesion marking and quantitative analysis (e.g., user assisted/reviewed automated or semi-automated lesion marking and quantitative analysis) of nuclear medicine images (e.g., a bone scan image set) of a human subject, the system comprising: a processor; and a memory having instructions thereon, wherein the instructions, when executed by the processor, cause the processor to: (a) access (e.g., and/or receive) a bone scan image set (e.g., a set of one, two, or more images) for the human subject, said bone scan image set obtained following administration of an agent (e.g., a radiopharmaceutical) to the human subject (e.g., the bone scan image set comprising an anterior bone scan image and a posterior bone scan image)(e.g., wherein each image of the bone scan image set comprises a plurality of pixels, each pixel having a value corresponding to an intensity); (b) automatically segment each image in the bone scan image set to identify one or more skeletal regions of interest, each skeletal region of interest corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images; (c) automatically detect an initial set of one or more hotspots, each hotspot corresponding to an area of elevated intensity in the annotated set of images [e.g., wherein detecting the one or more hotspots of the initial hotspot set comprises comparing pixel intensities with one or more threshold values (e.g., wherein the one or more threshold values vary depending on the identified skeletal region of interest in which a particular pixel is located)]; (d) for each hotspot in the initial set of hotspots, extract a set of (e.g., a set of one or more) hotspot features associated with the hotspot; (e) for each hotspot in the initial set of hotspots, calculate a metastasis likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input and output the metastasis likelihood value for that hotspot]; (f) automatically select a first subset (e.g., up to all) of the initial set of hotspots, wherein selection of a particular hotspot for inclusion in in the first subset is based at least in part on: (i) the metastasis likelihood value calculated for the particular hotspot [e.g., based on comparison of the likelihood value calculated for the particular hotspot with a likelihood threshold value (e.g., including the particular hotspot in the first subset if it has a likelihood value greater than the likelihood threshold value)]; and (ii) one or more global hotspot features, each global hotspot feature determined using a plurality of hotspots in the initial set of hotspots (e.g., a total number of hotspots in the initial hotspot set, an average intensity of hotspots in the initial hotspot set, a peak intensity of hotspots in the initial hotspot set, etc.); and (g) cause rendering of a graphical representation of at least a portion of the first subset of hotspots [e.g., a visual indication (e.g., points, boundaries) of hotspots overlaid on one or more images of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the one or more global hotspot features comprises a total number of hotspots in the initial hotspot set.

In certain embodiments, at step (f) the instructions cause the processor to adjust criteria for selection of hotspots for inclusion in the first subset based on the total number of hotspots in the initial hotspot set [e.g., by relaxing criteria as the total number of hotspots in the initial hotspot set increases (e.g., by reducing a metastasis likelihood threshold to which each hotspots metastasis likelihood value is compared; e.g., by scaling metastasis likelihood values based on the total number of hotspots in the initial hotspot set)].

In certain embodiments, at step (f) the instructions cause the processor to use a machine learning module to select the first subset (e.g., an ANN module) [e.g., wherein the machine learning module receives, for each hotspot, at least the metastasis likelihood value calculated for the hotspot and the one or more global hotspot features and outputs (i) an adjusted metastasis likelihood value that takes into account the global hotspot features (e.g., a value on a scale that can be compared to a threshold for selection of the hotspot in the first subset) and/or (ii) a binary (e.g., 0 or 1; e.g., Boolean True or False) value representing whether the hotspot should or should not be included in the first subset].

In certain embodiments, at step (c) the instructions cause the processor to (e.g., iteratively): identify healthy tissue regions in the images of the bone scan image set determined not to include any hotspots (e.g., localized regions of relatively high intensity); calculate a normalization factor such that a product of the normalization factor and an average intensity of the identified healthy tissue regions is a predefined intensity level; and normalize the images of the bone scan image set by the normalization factor.

In certain embodiments, the instructions further cause the processor to: (g) calculate one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the instructions cause the processor to: (h) select a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value]; and (i) cause rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the instructions cause the processor to: (j) calculate one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the instructions cause the processor to: (k) receive, via the GUI, a user selection of a second subset of the initial set of hotspots; and (l) calculate one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the system is a cloud based system. In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a system for lesion marking and quantitative analysis (e.g., user assisted/reviewed automated or semi-automated lesion marking and quantitative analysis) of nuclear medicine images (e.g., a bone scan image set) of a human subject, the system comprising: a processor; and a memory having instructions thereon, wherein the instructions, when executed by the processor, cause the processor to: (a) access (e.g., and/or receive) a bone scan image set (e.g., a set of one, two, or more images) for the human subject (e.g., the bone scan image set comprising an anterior bone scan image and a posterior bone scan image)(e.g., wherein each image of the bone scan image set comprises a plurality of pixels, each pixel having a value corresponding to an intensity); (b) automatically segment each image in the bone scan image set to identify one or more skeletal regions of interest, each skeletal region of interest corresponding to a particular anatomical region of a skeleton of the human subject (e.g., a particular bone and/or set of one or more bones, such as a cervical spine, a clavicle, a costae, a lumber spine, a pelvis, a sacrum, a scapula, a skull, a thoracic spine, a sternum, a femur, a humerus), thereby obtaining an annotated set of images; (c) automatically detect an initial set of one or more hotspots, each hotspot corresponding to an area of elevated intensity in the annotated set of images [e.g., wherein detecting the one or more hotspots of the initial hotspot set comprises comparing pixel intensities with one or more threshold values (e.g., wherein the one or more threshold values vary depending on the identified skeletal region of interest in which a particular pixel is located)]; (d) for each hotspot in the initial set of hotspots, extract a set of (e.g., a set of one or more) hotspot features associated with the hotspot; (e) for each hotspot in the initial set of hotspots, calculate a likelihood value corresponding to a likelihood of the hotspot representing a metastasis, based on the set of hotspot features associated with the hotspot [e.g., using one or more machine learning modules (e.g., pre-trained machine learning modules; e.g., artificial neural networks (ANNs)) that receive, for a particular hotspot, at least a portion of the hotspot features as input and output the likelihood value for that hotspot]; (f) select a first subset (e.g., up to all) of the hotspots of the initial set of hotspots based at least in part on the likelihood values calculated for each hotspot of the initial set of hotspots [e.g., by determining whether or not to include a particular hotspot of the initial set of hotspots in the set of pre-selected hotspots based on the likelihood value calculated for that particular hotspot (e.g., by comparing it with a likelihood threshold value)]; and (g) calculate one or more risk index values (e.g., a bone scan index value) using at least a portion (e.g., up to all) of the first subset of hotspots, said calculating comprising: computing, for each particular hotspot of the portion of first subset, a skeletal involvement factor based on a ratio of (i) a size (e.g., area) of the particular hotspot to (ii) a size (e.g., area) of a particular skeletal region to which the particular hotspot is assigned (e.g., by the processor) based on its location in the annotated set of images, thereby determining one or more skeletal involvement factors; adjusting the skeletal involvement factors using one or more region-dependent correction factors [e.g., each region-dependent correction factor associated with one or more skeletal regions; e.g., wherein the region-dependent correction factors have values selected to reduce a degree to which assigning a particular hotspot to a specific skeletal region (e.g., of a plurality of neighboring or nearby skeletal regions, such as sacrum, pelvic, and lumbar regions) causes fluctuations in computed skeletal involvement factors], thereby obtaining one or more adjusted skeletal involvement factors; and summing the adjusted skeletal involvement factors to determine the one or more risk index values.

In certain embodiments, for each particular hotspot, the computed skeletal involvement factor estimates a proportion of total skeletal mass occupied by a physical volume associated with the particular hotspot.

In certain embodiments, the instructions cause the processor to compute the skeletal involvement factor by: calculating a ratio of an area of the particular hotspot to an area of the corresponding skeletal region of interest, thereby computing an area fraction for the particular hotspot; and scaling (e.g., multiplying) the area fraction by a density coefficient associated with the skeletal region of interest to which the particular hotspot is assigned [e.g., that accounts for weight and/or density of bond in the corresponding skeletal region of interest (e.g., wherein the density coefficient is a weight fraction of the corresponding skeletal region of interest with respect to a total skeleton (e.g., of an average human)], thereby computing the skeletal involvement factor for the particular hotspot.

In certain embodiments, at least a portion of the hotspots of the first subset are assigned to a skeletal region of interest that is a member selected from the group consisting of a pelvis region (e.g., corresponding to a pelvis of the human subject), a lumbar region (e.g., corresponding to a lumbar column of the human subject), and a sacrum region (e.g., corresponding to a sacrum of the human subject).

In certain embodiments, the one or more region-dependent correction factors comprise a sacrum region correction factor associated with a sacrum region and used to adjust skeletal involvement factors of hotspots identified (e.g., by the processor) as being located therein, and wherein the sacrum region correction factor has a value less than one (e.g., less than 0.5).

In certain embodiments, the one or more region dependent correction factors comprise one or more correction factor pairs, each correction factor pair associated with a specific skeletal region of interest and comprising a first member and a second member (of the pair), wherein: the first member of the pair is an anterior image correction factor and is used to adjust skeletal involvement factors computed for hotspots having been detected in an annotated anterior bone scan image of the annotated image set, and the second member of the pair is a posterior image correction factor and is used to adjust skeletal involvement factors computed for hotspots having been detected in an annotated posterior bone scan image of the annotated image set.

In certain embodiments, at step (c) the instructions cause the processor to (e.g., iteratively): identify healthy tissue regions in the images of the bone scan image set determined not to include any hotspots (e.g., localized regions of relatively high intensity); calculate a normalization factor such that a product of the normalization factor and an average intensity of the identified healthy tissue regions is a predefined intensity level; and normalize the images of the bone scan image set by the normalization factor.

In certain embodiments, the instructions further cause the processor to: (g) calculate one or more risk index values for the human subject based at least in part on a computed fraction (e.g., an area fraction) of the skeleton of the human subject occupied by the initial set of hotspots [e.g., wherein the computed fraction is a ratio of a total area of the initial set of hotspots, divided by a total area of all identified skeletal regions].

In certain embodiments, the instructions cause the processor to: (h) select a first subset (e.g., up to all) of the initial set of hotspots based at least in part on the metastasis likelihood values [e.g., determining whether or not to include a particular hotspot of the initial set of hotspots in the subset based on the metastasis likelihood value calculated for that particular hotspot exceeding a threshold value]; and (i) cause rendering of a graphical representation of the first subset [e.g., a visual indication (e.g., points, boundaries) of hotspots overlaid on one or more members of the bone scan image set and/or annotated set of images; e.g., a table listing identified hotspots along with additional information (e.g., location; e.g., likelihood value) for each hotspot] for display within a graphical user interface (GUI) (e.g., a cloud-based GUI).

In certain embodiments, the instructions cause the processor to: (j) calculate one or more risk index values for the human subject based at least in part on a computed fraction (e.g., an area fraction) of the skeleton of the human subject occupied by the first subset of hotspots [e.g., wherein the computed fraction is a total area of the initial set of hotspots divided by a total area of all identified skeletal regions].

In certain embodiments, the instructions cause the processor to: (k) receive, via the GUI, a user selection of a second subset of the initial set of hotspots; and (l) calculate one or more risk index values for the human subject based at least in part on a computed fraction (e.g., an area fraction) of the skeleton of the human subject occupied by the second subset of hotspots [e.g., wherein the computed fraction is a total area of the second subset of hotspots, divided by a total area of all identified skeletal regions].

In certain embodiments, at least one of the risk index values is indicative of a risk of the human subject having and/or developing metastatic cancer (e.g., metastatic prostate cancer, metastatic breast cancer, metastatic lung cancer, and other metastatic bone cancers).

In certain embodiments, the metastatic cancer is metastatic prostate cancer.

In certain embodiments, at least one of the risk index values is indicative of the human subject having a particular state of metastatic cancer (e.g., metastatic prostate cancer, metastatic breast cancer, metastatic lung cancer, and other metastatic bone cancers).

In certain embodiments, the system is a cloud based system. In certain embodiments, the processor is a processor of a cloud-based system.

In certain embodiments, the GUI is part of a general Picture Archiving and Communications System (PACS) (e.g., as well as a clinical application for oncology including lesion marking and quantitative analysis).

In certain embodiments, the agent (e.g., radiopharmaceutical) comprises technetium 99m methylenediphosphonate ($^{99m}$Tc-MDP).

In another aspect, the invention is directed to a computer aided image analysis device [e.g., a computer-aided detection (CADe) device; e.g., a computer-aided diagnostic (CADx) device] comprising the system of any one of the aspects and embodiments described herein (for example in the paragraphs above).

In certain embodiments, the device is programmed to be used by trained healthcare professionals and/or researchers [e.g., for acceptance, transfer, storage, image display, manipulation, quantification, and reporting of digital medicine images acquired using nuclear medicine imaging; e.g., wherein the device provides general Picture Archiving and Communications System (PACS) tools and/or a clinical application for oncology, including lesion marking and quantitative analysis].

In certain embodiments, the device is programmed to be used for analysis of bone scan images for evaluation and/or detection of metastatic cancer (e.g., metastatic prostate cancer, metastatic breast cancer, metastatic lung cancer, and other metastatic bone cancers).

In certain embodiments, the device is programmed to be used for analysis of bone scan images for evaluation and/or detection of prostate cancer.

In certain embodiments, the device comprises a label specifying that the device is intended to be used by trained healthcare professionals and/or researchers [e.g., for acceptance, transfer, storage, image display, manipulation, quantification, and reporting of digital medicine images acquired using nuclear medicine imaging; e.g., wherein the device provides general Picture Archiving and Communications System (PACS) tools and/or a clinical application for oncology, including lesion marking and quantitative analysis].

In certain embodiments, the label further specifies that the device is intended to be used for analysis of bone scan images for evaluation and/or detection of metastatic cancer (e.g., metastatic prostate cancer, metastatic breast cancer, metastatic lung cancer, and other metastatic bone cancers).

In certain embodiments, the label further specifies that the device is intended to be used for analysis of bone scan images for evaluation and/or detection of prostate cancer.

Embodiments described with respect to one aspect of the invention may be, applied to another aspect of the invention (e.g., features of embodiments described with respect to one independent claim, e.g., a method claim, are contemplated to be applicable to other embodiments of other independent claims, e.g., a system claim, and vice versa).

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 2 is a screenshot of a graphical user interface (GUI) for selecting patient data for review, used with a software based implementation of the quality control and reporting workflow shown in FIG. 1, according to an illustrative embodiment.

FIG. 3 is a screenshot of a graphical user interface (GUI) for reviewing patient information, used with a software based implementation of the quality control and reporting workflow shown in FIG. 1, according to an illustrative embodiment.

FIG. 9A is a screenshot of a GUI window displaying a listing of patients as presented in a predicate device, according to an illustrative embodiment.

FIG. 9B is a screenshot of a GUI window displaying a listing of patients as presented in a proposed new device, according to an illustrative embodiment.

FIG. 14A is a screenshot of a GUI showing bone scan images from different studies displayed and selectable via different GUI tabs, according to an illustrative embodiment.

FIG. 14B is a screenshot of a GUI showing bone scan images from different studies displayed simultaneously, alongside each other, according to an illustrative embodiment.

FIG. 14C is a screenshot of a GUI showing anterior and posterior images displayed and selectable via different GUI tabs, according to an illustrative embodiment.

FIG. 14D is a screenshot of a GUI showing anterior and posterior images displayed simultaneously, alongside each other, with visibility of various images selectable via checkboxes in the GUI, according to an illustrative embodiment.

FIG. 17A is a screenshot of a GUI showing a hotspot table listing hotspots identified within a bone scan image set, according to an illustrative embodiment.

FIG. 17B is a screenshot of a GUI showing identified hotspots and illustrating an updated BSI value following exclusion of an automatically detected hotspot based on user input via the GUI, according to an illustrative embodiment.

FIG. 17C is a screenshot of a GUI showing identified hotspots and illustrating an updated BSI value following inclusion of a previously excluded automatically detected hotspot based on user input via the GUI, according to an illustrative embodiment.

FIG. 19A is a screenshot of a GUI showing display of calculated BSI values for different studies and included hotspots in a tabular fashion, according to an illustrative embodiment.

FIG. 19B is a screenshot of a GUI showing display of calculated BSI values as headers above windows showing bone scan images for different studies, according to an illustrative embodiment.

FIG. 20A is a screenshot of a GUI displaying a graph showing changes in computed BSI value over time, according to an illustrative embodiment.

FIG. 20B is a screenshot of a GUI displaying a graph showing changes in computed BSI value over time, according to an illustrative embodiment.

FIG. 21 is a screenshot of a GUI providing a table listing number of hotspots in particular anatomical regions used for computation of BSI values in different studies, according to an illustrative embodiment.

FIG. 22A is a screenshot of an automatically generated report based on an approach for automated analysis of bone scan images and calculation of BSI values, according to an illustrative embodiment.

FIG. 22B is a screenshot of an automatically generated report based on an approach for automated analysis of bone scan images and calculation of BSI values, according to an illustrative embodiment.

DETAILED DESCRIPTION

Figure 1:
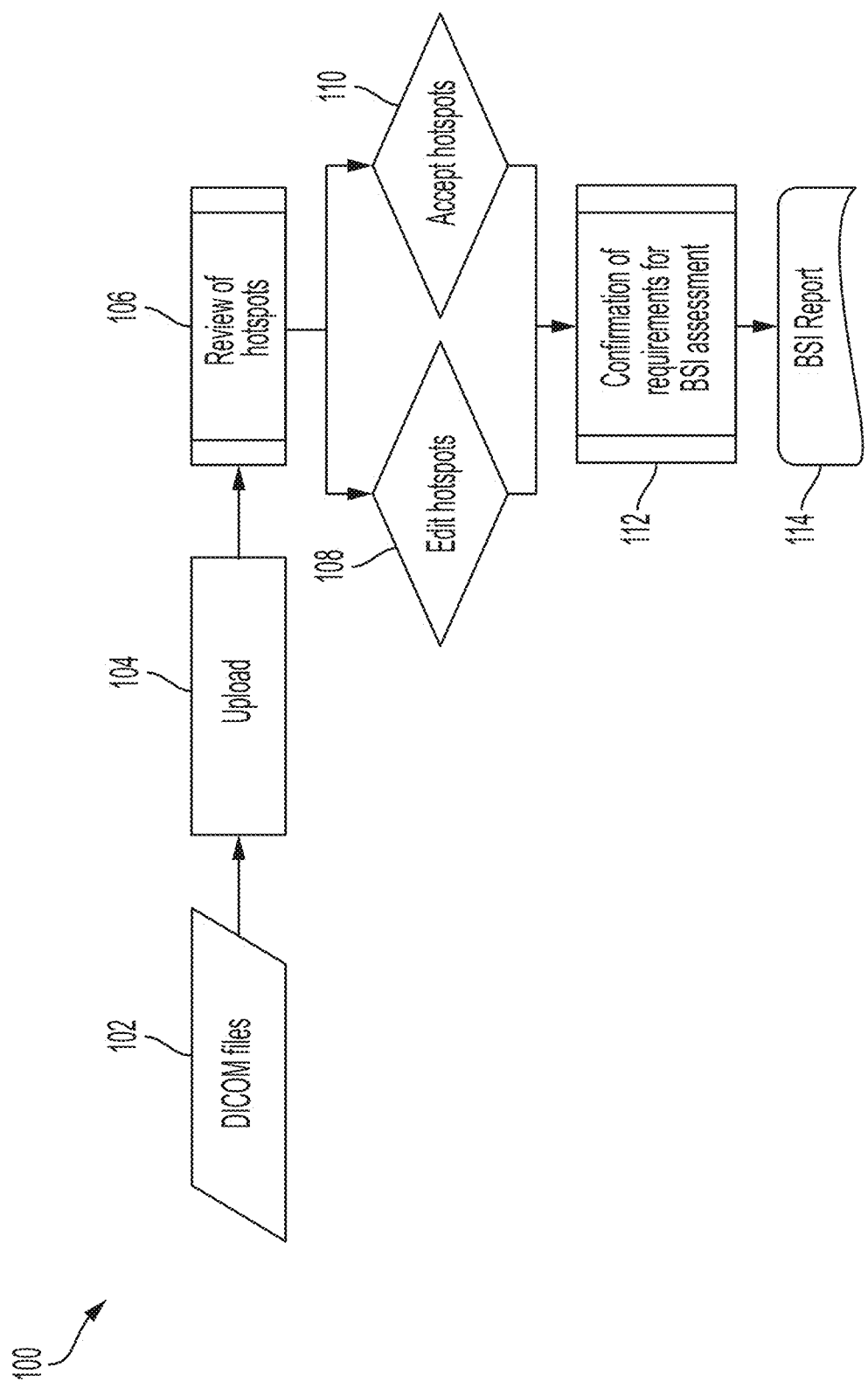
FIG. 1 is a block flow diagram showing a quality control and reporting workflow for generating a BSI report, according to an illustrative embodiment.

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

The systems and methods described herein are directed to improved computer aided display and analysis of nuclear medicine images. In particular, in certain embodiments, the systems and methods described herein provide improvements to several image processing steps used for automated analysis of bone scan images for assessing cancer status of a patient. For example, improved approaches for image segmentation, hotspot detection, automated classification of hotspots as representing metastases, and computation of risk indices such as bone scan index (BSI) values are provided. Automated BSI calculation technology is described in detail in U.S. patent application Ser. No. 15/282,422, filed Sep. 30, 2016, in U.S. Pat. No. 8,855,387, issued Oct. 7, 2014 (of which U.S. patent application Ser. No. 15/282,422 is a reissue), and PCT Application No. PCT/US17/58418, filed Oct. 26, 2017, the content of each of which is hereby incorporated by reference in its entirety. PCT Application PCT/US2017/058418, filed Oct. 26, 2017, also incorporated herein in its entirety, describes a cloud-based platform that can serve as a platform for providing image analysis and BSI calculation tools in accordance with the approaches described herein.

In particular, in certain embodiments, bone scan images are acquired following administration of an agent, such as a radiopharmaceutical, to a human subject. The administered agent accumulates in cancerous bone lesions as a result of physical properties of the underlying tissue (e.g., increased vasculature, abnormal osteogenesis) or due to recognition (by the agent) of particular biomolecules that are selectively expressed or over-expressed in tumors, such as prostate-specific membrane antigen (PSMA). The agent comprises radionuclide(s) that emit nuclear radiation, which can be detected and thereby used to image the spatial distribution of agent within the subject.

For example, in certain embodiments, bone scan images are acquired as two-dimensional scans using a gamma camera. For example, two images—an anterior and a posterior image—are acquired to form a bone scan image set. Physical regions where the agent has accumulated at high concentrations appear as regions of elevated intensity, i.e., bright spots, in bone scan images. The agent may accumulate in cancerous bone lesions, e.g., as described above, as well as other regions, such as the bladder of the subject.

In order to accurately identify regions of bone scan images representing lesions, and generate a quantitative estimate of tumor burden, a series of image processing steps are performed. In particular, bone scan images are segmented to identify regions corresponding to bones of the subject's skeleton, forming an annotated set of images. Regions of elevated intensity with respect to their surroundings are identified within the skeletal regions and compared with thresholds to detect an initial set of hotspots. Features of the initial hotspots, such as a hotspot size (e.g., area), hotspot shape (e.g., as described by various metrics, such as radius, eccentricity), and/or measure of hotspot intensity (e.g., peak intensity, average intensity, integrated intensity, etc.), are extracted and used to determine, for each hotspot, a metastasis likelihood value that represents a likelihood of the hotspot representing a metastases. For example, in certain embodiments, the metastasis likelihood values are computed using artificial neural networks (ANNs) that receive as input, for each hotspot, a set of hotspot features and output a metastasis likelihood value.

The metastasis likelihood values can be used to automatically filter the initial set of hotspots, to determine a subset to be used for calculation of risk indices that indicate a risk of the subject having and/or developing metastatic cancer. By filtering hotspots in this manner, only those determined to have a high likelihood of representing a metastasis are included in the risk index calculations. In certain embodiments, graphical representations of hotpots and/or their likelihood values are rendered for display to a user, for example as overlaid markings on annotated images and/or tables of information, allowing the user to select a subset of the hotspots for use in calculating risk indices. This allows the user to augment the automated selection of hotspots for calculation of risk indices with their input.

The approaches described herein include several improvements to the aforementioned image processing steps, providing for improved accuracy of lesion detection and risk index calculations. For example, the present disclosure includes and improved segmentation approach whereby an entire (e.g., more than three-quarters length) humerus and/or an entire (e.g., more than three-quarters length) femur region is/are identified. Previously, only a limited faction of the femur and humerus bones were identified. Segmenting a larger (e.g., entire) portion of these bones allows lesions located further out in the extremities of a subject's arms and legs to be identified. In order to account for reduced uptake of the agent in these extremities, the approach described herein also utilizes region dependent thresholds in the hotspot detection step. The region-dependent threshold values vary for different skeletal regions, and have lower values in the femur and humerus regions, so as to increase detection sensitivity therein.

In another improved approach, the systems and methods described herein may use a global threshold scaling technique to detect hotspots. With this approach, the initial set of hotspots is detected by first identifying a set of potential hotspots, using a plurality of preliminary region-dependent thresholds. The potential set of hotspots is used to compute a global threshold scaling factor, based on an area fraction of the subject's skeleton occupied by the set of potential hotspots. The preliminary thresholds are then adjusted using the global threshold scaling factor, and the adjusted thresholds used to detect the initial set of hotspots. This approach was found to ultimately increase linearity of risk indices computed using the initial set of hotspots, particularly for high levels of disease burden—for example, where the subject suffered from numerous lesions, and a large fraction of the skeleton was occupied by hotspots.

The present disclosure also includes improvements for selection of hotspots and calculation of risk indices. For example, the approaches described herein may use a hotspot pre-selection technique that filters hotspots based not only on their computed metastasis likelihood values, but also global hotspot features that measure properties of the overall set of initial hotspots, such as a total number of hotspots in the set. Other examples of global hotspot features include other measures of total hotspot number, such as an average number of hotspots per region, measures of overall hotspot intensity, such as peak or average hotspot intensity, and measures of overall hotspot size, such as a total area of hotspots, an average hotspot size, etc. This allows the processing approach to leverage clinical experience showing that hotspot selection depends on the rest of the image. In particular, the probability of a hotspot being selected is higher if there are many other hotspots and lower if it is the only hotspot. Selecting or filtering hotspots based only on their individual metastasis likelihood values can, accordingly, result in underestimation of calculated risk index values in subjects with many hotspots. Incorporating global features as described herein can improve performance in patients with many hotspots.

Finally, the systems and methods described herein also offer improvements to approaches for calculating risk index values based on skeletal involvement, such as bone scan index (BSI). For example, BSI is a risk index value that provides an estimate of the fraction of a subject's total skeletal mass occupied by cancerous lesions. Calculating BSI involves calculating, for each particular hotspot, a skeletal involvement factor based on a ratio of the area of the particular hotspot to that of the skeletal region in which it is located. Scaled versions (e.g., to convert area ratios to relative mass) are summed to compute the BSI value for the subject. However, difficulties in correctly locating the specific skeletal region in which a particular hotspot is located can lead to errors in BSI values. Bone scan images are two dimensional images, but the underlying skeleton of the subject is a three dimensional structure. Accordingly, a hotspot may be incorrectly identified as located in one region, when in fact its represent a lesion located in a different bone. This is a particular challenge for the sacrum and neighboring pelvic and lumbar regions. In order to account for this challenge, the present disclosure includes a modified risk index calculation approach that uses region-dependent correction factors to scale skeletal involvement factors in a manner that accounts for potential errors in localizing hotspots. This approach improves accuracy of BSI calculations, and limits sensitivity to hotspot localization.

Accordingly, the systems and methods described herein include several improved image analysis techniques for lesion identification and quantification. These approaches improve accuracy and robustness with which bone scan images can be analyzed. As described herein, they can be used as part of a cloud-based system that facilitates review and reporting of patient data, and allows for improved disease detection, treatment, and monitoring.

A. Nuclear Medicine Images

Nuclear medicine images are obtained using a nuclear imaging modality such as bone scan imaging, Positron Emission Tomography (PET) imaging, and Single-Photon Emission Tomography (SPECT) imaging.

As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method. As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation.

In certain embodiments, nuclear medicine images use imaging agents comprising radiopharmaceuticals. Nuclear medicine images are obtained following administration of a radiopharmaceutical to a patient (e.g., a human subject), and provide information regarding the distribution of the radiopharmaceutical within the patient. Radiopharmaceuticals are compounds that comprise a radionuclide.

As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments.

As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

Nuclear medicine images (e.g., PET scans; e.g., SPECT scans; e.g., whole-body bone scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity in nuclear medicine images. Accordingly, presence of malignant bone lesions associated with metastatic prostate cancer can be inferred by identifying such hotspots within a whole-body scan of the patient. As described in the following, risk indices that correlate with patient overall survival and other prognostic metrics indicative of disease state, progression, treatment efficacy, and the like, can be computed based on automated analysis of intensity variations in whole-body scans obtained following administration of $^{99m}$Tc MDP to a patient. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example 18F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest— particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals corresponding to PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. Risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

A variety of PSMA binding agents and radionuclide labelled versions thereof are described in U.S. Pat. Nos. 8,778,305, 8,211,401, and 8,962,799, each of which are incorporated herein by reference in their entireties. Several PSMA binding agents and radionuclide labelled versions thereof are also described in PCT Application PCT/US2017/058418, filed Oct. 26, 2017, incorporated herein by reference in its entirety.

B. Bone Scan Imaging Devices for Image Analysis

In certain embodiments, computer aided image analysis devices as described herein are intended to be used by trained healthcare professionals and researchers for acceptance, transfer, storage, image display, manipulation, quantification, and reporting of digital medical images acquired using nuclear medicine (NM) imaging. In certain embodiments, such devices provide general Picture Archiving and Communications System (PACS) tools as well as clinical applications for oncology, including lesion marking and quantitative analysis C. Analysis of Bone Scan Images and Computation of Bone Scan Index Values Bone scintigraphy (also referred to as bone scan imaging) is an imaging modality widely used to assess skeletal disease burden. A current standard of assessing disease progression based on bone scan images is based on the semi-quantitative modified Prostate Cancer Working Group 2 and the Prostate Cancer Working Group 3 (PCWG) criteria. The definition of this criteria relies on the appearance of new lesions as interpreted by a trained reader: (i) either two new lesions followed by two additional lesions on a first and second follow-up scans compared to a pretreatment scan (known at the 2+2 rule), or (ii) two new confirmed lesions relative to the first follow-up scan thereafter. However, this semi-quantitative assessment approach of counting lesion number has a number of limitations. In particular, the assessment is subject to manual variability, it is confined to assessing disease progression, and is unable to assess accurate burden of confluent/diffused diseases as is relevant, e.g., to metastatic prostate cancer.

Accordingly, there is a high unmet need for an automated and quantitative assessment of bone scans. The automated Bone Scan Index (BSI), developed by EXINI Diagnostics AB, Lund Sweden, is a fully quantitative assessment of a patient's skeletal disease on a bone scan, as the fraction of the total skeleton weight. The BSI has undergone rigorous pre-analytical and analytical validation as an objective measure of the quantitative change in disease burden bone scans. In a recent phase 3 prospective study, BSI assessment was demonstrated to risk stratify metastatic prostate cancer patients.

The systems and methods described herein are directed to improved computer aided approaches for analyzing bone scan images and computing BSI in automated and semi-automated, user guided, fashions. Also described herein are GUI tools that facilitate review of bone scan images and automated analyses used to determine BSI values by a user.

D. Device Description of an Example aBSI Platform

In certain embodiments, systems and methods described herein can be implemented as a cloud based platform for automated and semi-automated image analysis for detection and evaluation of cancer status in a patient. An example device described herein is the automated BSI device (aBSI), which is as a cloud-based software platform with a web interface where users can upload bone scan image data in the form of particular image files, such as DICOM files. The software complies with the Digital Imaging and Communications in Medicine (DICOM 3) standard.

In certain embodiments, devices (e.g., computer aided image analysis tools) in accordance with the systems and methods described herein are programmed for an intended user, typically a health-care professional who uses the software to view patient images and analyze results. The user operates the service in a web browser, (such as Google's Chrome browser) on a computer running an operating system such as Microsoft Windows or OSX. The software can be configured to occupy a single application window. The service is web-based and accessed via a specific URL. Keyboard and mouse controls may be used for operating the software.

Multiple scans can be uploaded for each patient and the system provides a separate image-based automated analysis for each. The automated analysis is reviewed by the physician, who may be guided through a quality control and reporting workflow. If the quality control of the automated assessment is approved, a report can be created and signed. The service can be configured for HIPAA and 21 CFR part 11 compliance.

i. Service Access

In certain embodiments, access to software tools in accordance with the systems and methods described herein is restricted and protected by security measures. For example, access to a cloud-based implementation of the systems and methods described herein, aBSI, is protected by multi-factor authentication in the form of a username, password and verification code sent as a text message to the phone number associated with the account ii. System Requirements In certain embodiments, software enforced requirements include one or more of the following:

Computer with Windows or OS X with internet access,

Chrome browser,

An available personal mobile phone (for multi factor authentication only)

In certain embodiments, user enforced requirements include one or more of the following:

Chrome browser a. At least version 54 b. JavaScript must be allowed c. HTML5 is required d. Writing to local storage and session storage is needed Display resolution at least 1280×960 iii. Image Requirements

In certain embodiments, software enforced requirements include one or more of the following:

Images must be uncompressed and in DICOM 3 format.

Modality (0008,0060) must be "NM"

Image type (0008,0008) must be "ORIGINAL\PRIMARY\WHOLE BODY\EMISSION"

Study date (0008,0020) must contain a valid date

Number of frames (0028,0008) must be 1 or 2

Number of slices (0054,0081) must be 1 or 2

Pixel spacing (0028,0030) must be $\geq 1.8$ mm/pixel and $\leq 2.8$ mm/pixel

The image must be of a shape such that the number of rows ≥columns

Patient sex (0010,0040) must be M

The anterior and posterior images may be stored as either two different series (two files with different Series Instance UID) or as one multiframe series (one file) containing two frames.

Image pixel data should be in the 16-bit range. Images with pixels ranging from 0 to 255 (8-bit) are not sufficient.

In certain embodiments, user enforced requirements include one or more of the following:

The anterior and posterior images should cover at least an area from the scalp to the upper part of tibia, and the upper part of antebrachium of each arm.

No filtering or other post-processing techniques must be applied to images

In certain embodiments, whole-body bone scintigraphy images are acquired in compliance with relevant guidelines, such as "EANM Bone scintigraphy: procedure guidelines for tumor imaging" and "ACR-SPR Practice Parameter for the Performance of Skeletal Scintigraphy (Bone Scan)".

iv. Workflow

FIG. 1 is a block flow diagram showing a quality control and reporting workflow 100 for generating a BSI report, according to an illustrative embodiment. In certain embodiments, the systems and methods described herein include a GUI for guiding a user (e.g., healthcare professional) through review and analysis of patient image data to compute an automated BSI value and generate a report. The workflow 100 allows the user to select 102 and upload 104 image files of patient data, which are then analyzed by the software and reviewed by the user.

The user may be presented with a first GUI window, such as the window 200 shown in FIG. 2, that allows the user to select a particular patient for review/analysis from a list. Upon selection of a row corresponding to the particular patient in the list in FIG. 2, a new and/or updated window 300, shown in FIG. 3, showing patient information is displayed.

Figure 4:
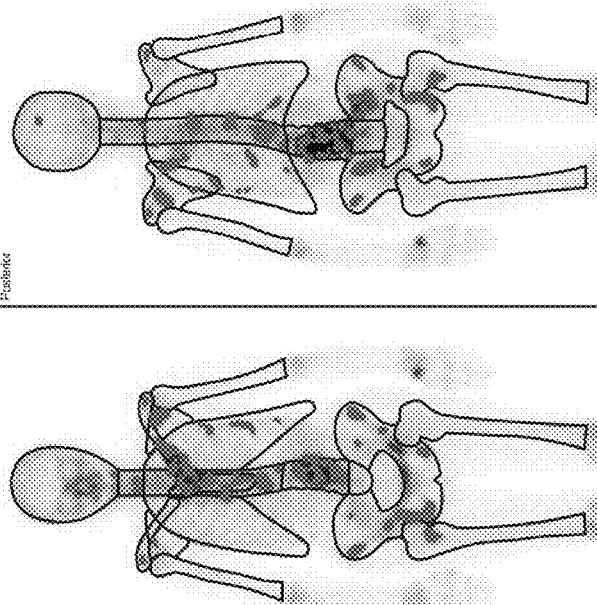
FIG. 4 is a screenshot of a graphical user interface (GUI) for reviewing image data for a patient and editing hotspot selection, used with a software based implementation of the quality control and reporting workflow shown in FIG. 1, according to an illustrative embodiment.

Turning to FIG. 4, the user may then access a review page 400 of the guided analysis software. The review page 400 provides the user (e.g., healthcare professional, such as a physician) with a GUI that allows them examine image data and automated identification of hotspots performed by software backend, in order to calculate the automated BSI index for the patient. Automated BSI calculation technology is described further detail herein, and previous versions (without the improvements of the present disclosure) are described in detail in U.S. patent application Ser. No. 15/282,422, filed Sep. 30, 2016, and in U.S. Pat. No. 8,855,387, issued Oct. 7, 2014 (of which U.S. patent application Ser. No. 15/282,422 is a reissue), and PCT Application No. PCT/US17/58418, filed Oct. 26, 2017, the content of each of which is hereby incorporated by reference in its entirety.

Figure 5:
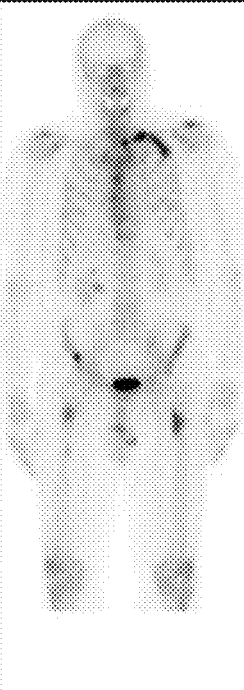
FIG. 5 is a screenshot of an automatically generated report, generated by a user following the software based implementation of the quality control and reporting workflow shown in FIG. 1, according to an illustrative embodiment.

The review page allows the user review 106 of hotspots, representing cancerous lesions, that have been automatically identified in images by the software. The user may use the review page GUI to edit 108 the set of regions identified as hotspots, and must confirm that image quality, skeletal segmentation (as depicted by the outlining in the screenshot), and that the set of identified hotspots have been reviewed and accepted 110 in order to proceed with report generation. Once the user's review and quality control have been confirmed 112, a report such as the report 500 shown in FIG. 5, including a final BSI computed value, may be generated 114.

v. Image Processing

Figure 6:
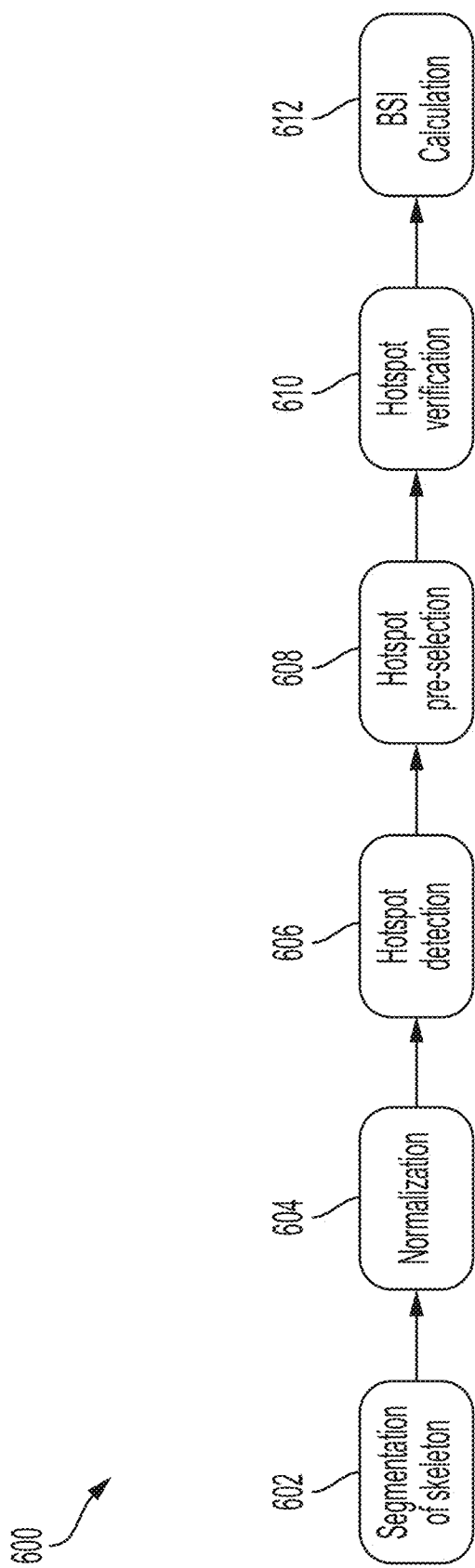
FIG. 6 is a block flow diagram of a process for processing whole body bone scan images and determining a bone scan index (BSI) value, according to an illustrative embodiment.

As shown in the block flow diagram of FIG. 6, the systems and methods described herein may be used in a process 600 for automated detection and pre-selection of hotspots, receipt of a user verification of the set of preselected hotspots, and for calculation of a risk index value, such as, in particular, a bone scan index (BSI) value.

In particular, in certain embodiments, as shown in FIG. 6, in a segmentation step 602, the software tools described herein use an algorithm for image registration to bring patient images into a reference coordinate frame. This is done by non-rigidly adjusting an atlas image to each patient image. By fitting the atlas image to the patient, the patient image can be segmented into a skeleton region and background region. The skeleton region can be further divided into smaller skeletal regions of interest, also referred to herein as localizations. In a normalization step 604, the whole-body bone scan images are normalized to provide a user with a standardized intensity range when viewing images at different contrast and brightness levels. Hotspots are detected in a hotspot detection step 606. In certain embodiments, hotspots are detected using a thresholding rule. In another step, hotspot pre-selection 608 is performed. In certain embodiments, pre-selection of hotspots is based on image analysis and machine learning techniques that aim to pre-select significant hotspots for inclusion in a set of pre-selected hotspots, which may be reviewed by the user in a hotspot verification step 610. This pre-selection selection is based on a range of features, such as size, location, orientation, shape and texture of the hotspots. In certain embodiments, pre-selection is a user-convenience tool, aiming to reduce the number of manual clicks that a user must perform (e.g., to select hotspots to use for computing risk indices, such as a BSI value). In certain embodiments, the pre-selection step may be followed by a mandatory hotspot verification step where the user must review and approve the preselection of hotspots or if needed manually include and/or exclude hotspots to be able to create a report.

In another step 612, a particular risk index referred to as Bone Scan Index (BSI) is computed using the set of verified hotspots. In certain embodiments, Bone scan index (BSI) is defined as the sum of the skeletal involvement for all included hotspots. Involvement is an estimate of the proportion of total skeletal mass contributed by the volume corresponding to a hotspot and is expressed as a percentage. Involvement may be calculated using the following formula, where C is an anatomical area coefficient related to a density of the bone:

$$\text{Involvement} = \frac{\text{Area of hotspot} \times C}{\text{Area of anatomical region}}.$$

Segmentation of Skeletal Regions

Figure 7:
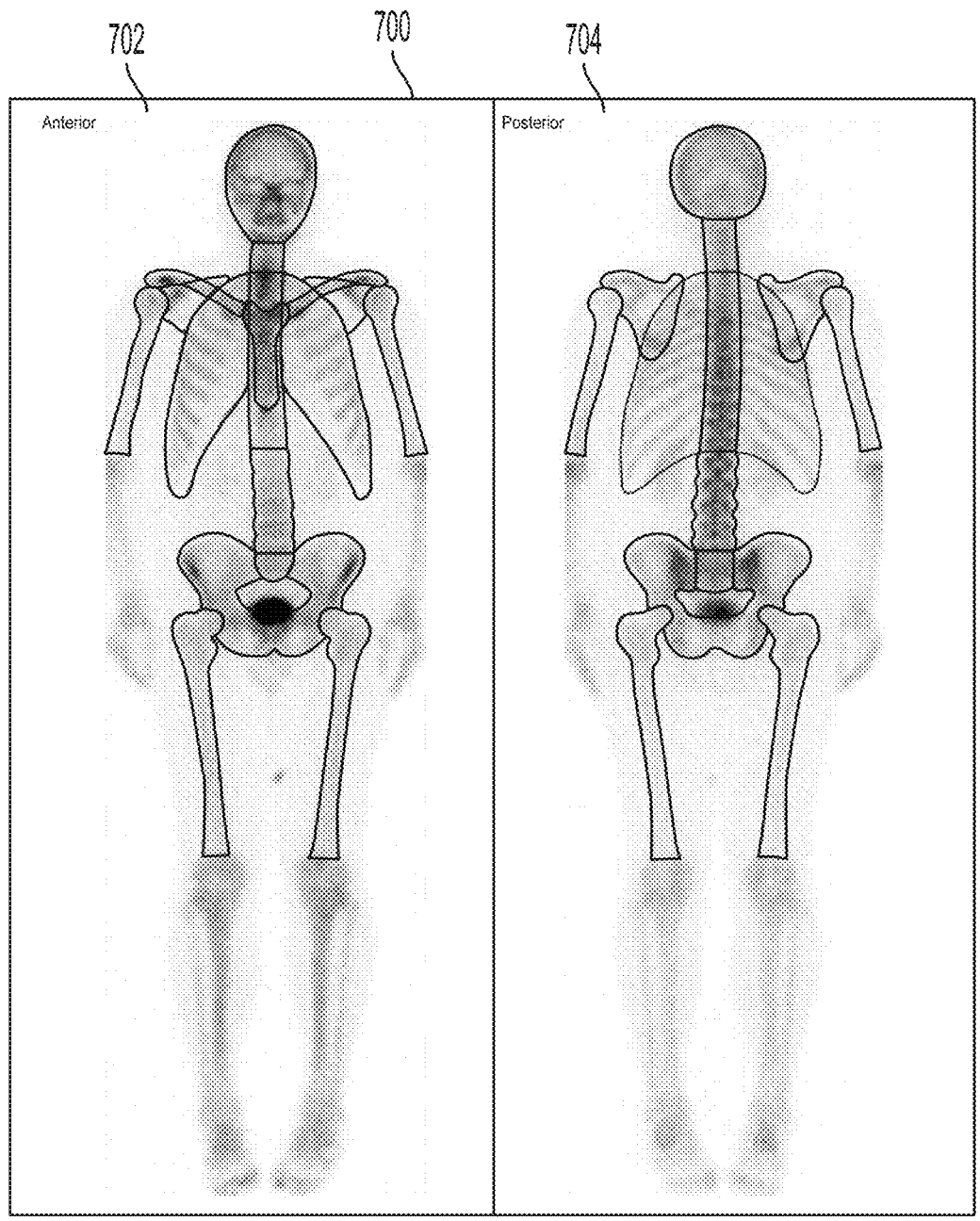
FIG. 7 is a whole body bone scan image set showing a skeletal atlas overlaid on anterior and posterior bone scan images for skeletal segmentation, according to an illustrative embodiment.

In certain embodiments, skeletal segmentation is performed using a segmentation by registration approach in which an atlas image is registered with a bone scan image to be segmented. In this approach, the device automatically contours the skeleton into distinct skeletal regions by elastically fitting a manually contoured annotated template image set to each analyzed image set. This annotated template image set is known as the skeletal atlas image set. This atlas image set is structured just like any patient image—it looks like a regular bone scan and comprises one anterior and one posterior image. The atlas images provide a fixed reference when analyzing a scan. The atlas is manually annotated with the regions of interest (skeletal regions) that can be transferred to a new scan to accurately calculate BSI. An example atlas image set 700 with 31 manually drawn skeletal regions is shown in FIG. 7. As shown in FIG. 7, just like a bone scan image set, the atlas image set 700 may comprise an anterior image 702 and a posterior image 704.

When a bone scan image is analyzed, the atlas images are elastically deformed to resemble the bone scan image. The same transformation is then applied to the atlas contours, thereby producing a delineation/segmentation of each skeletal region of interest of the patient bone scan image. Additional detail regarding construction of a suitable atlas is described at the end of this section.

Deforming the skeletal atlas to fit a patient scan. In certain embodiments, deformation of the skeletal atlas to fit a patient's bone scan image follows an iterative approach. The segmentation algorithm proceeds in iterations, where in each iteration, a vector is estimated for every pixel describing how the pixel should be displaced to its corresponding position in the target image. With individual displacements for every pixel, chances are that the displacement vectors will cross or share target position, which will result in holes and/or tears in the deformed image. To avoid this, the vector field is smoothed using a filtering approach. Displacements are estimated by applying complex-valued filters to the atlas and target images. The complex filter responses can be expressed in terms of an amplitude and phase for each pixel. It can be shown that local phase differences, i.e. phase differences between pixels that are within a short distance of each other, are proportional to the size of the displacement necessary to bring them into alignment. To obtain an estimate of the direction of the displacement, this process is repeated several times for varying filter angles. Knowing the angles of each filter and the resulting magnitude of the displacement makes it possible to infer the direction in which the largest displacement can be observed. While this approach works for small displacements, it must also be possible to apply it in cases where the atlas and target images are further apart. To achieve this, a subsampling approach is taken where the algorithm is first applied to a subsampled (down-sized) version of the image. This approach treats large displacements as local differences. Then, the algorithm proceeds to increasingly more detailed (less subsampled) images to add more detail and variability to the resulting displacement field. The algorithm is run on a fixed pyramid of subsampled images, for a fixed number of iterations at each pyramid level, and with a predetermined level of smoothing.

Construction of a skeletal atlas. The example aBSI device described herein relies on a single atlas image. The contouring algorithm is driven by structural information in the atlas and target images and seeks to deform the atlas image such that distances between similar structures in the two images are minimized. Structure is defined by edges and ridges (lines) in the images. Accordingly, global intensity differences and texture patterns are disregarded by the algorithm. As a result, a suitable atlas image exhibits two important properties:

It displays the same pattern of edges and ridges; and
The (elastic) transformation needed to bring the images into alignment is minimized on average over the set of anticipated anatomical variation among analyzed images.

Figure 8:
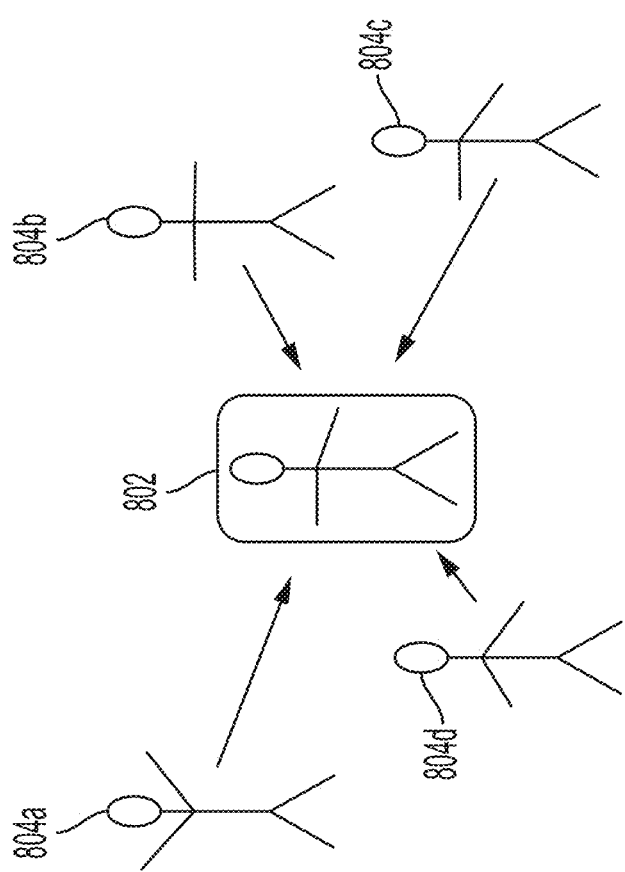
FIG. 8 is a schematic illustrating construction of a skeletal atlas from multiple images patient images, according to an illustrative embodiment.

In certain embodiments, to meet these requirements, atlas images based on a database of real, normal (e.g., no metastases or other visible medical conditions) bone scan images are used. A contouring algorithm can be used to bring all images of the database in alignment with each other. Then, an average transformation is computed from all resulting transformations. Subsequently, all images are transformed to this anatomical average, representing the average anatomy in the database. In this process, intensities are also normalized, creating a typical bone scan image suitable as an anatomical reference. The schematic shown in FIG. 8 illustrates this idea conceptually—how average anatomy and intensities (center image, 802) can be inferred from multiple bone scan images 804a, 804b, 804c, 804d of a database.

In certain embodiments, the average anatomy used for the atlas image set converges to a stable estimate quickly as the number of scans included is increased. A relatively small number (e.g., 30) scans can be sufficient to create a representative reference image. Moreover, since the algorithm is driven by major structures in the images and is not sensitive to differences in shape and/or size, a single atlas can be applied to any bone scan image for skeletal segmentation.

Intensity Normalization and Hotspot Detection

A challenge when reading scintigraphy images such as bone scans is that intensity levels between scans may differ due to a variety of parameters such as injected dose, time from injection to scanning, scan time, body type, camera hardware and configuration etc. In certain embodiments, in order to facilitate reading for users and as part of the quantification pipeline (e.g., as shown in FIG. 6), input bone scans are normalized such that the average intensity of healthy bone tissue is scaled to a predetermined reference level. At this stage of the quantification pipeline, skeletal segmentation has been carried out and the pixels belonging to the skeleton are known. However, to measure the average intensity of healthy tissue, and thus be able to normalize the scan, regions of high intensity must be identified and excluded. This detection of hotspots in the skeleton is straight-forward if the images have already been normalized. This is a chicken-and-the-egg type of problem where hotspot detection is needed to normalize the images, and the hotspot detection is dependent on normalized images. Accordingly, an iterative approach, such as the steps listed below, can be used to address this challenge:

(1) Estimate the normalization with the assumption that all bone tissue is healthy (no hotspots);
(2) Detect hotspots given the current normalization;
(3) Estimate the normalization given the current set of hotspots; and
(4) Iterate steps (2) and (3) until convergence.

This iterative process converges within 3 or 4 iterations to a stable value for both the normalization and the hotspot detection. Hotspots are detected using a simple thresholding approach wherein the image is filtered using a difference-of-Gaussians band-pass filter which emphasizes small regions of high intensity relative to their respective surroundings. This filtered image is then thresholded at a region based constant level.

In certain embodiments, different threshold values are used for different skeletal regions of interest. For example, threshold levels used in the cloud-based aBSI example embodiment are 650 for cervical spine, clavicle, costae, lumbar spine, pelvis, sacrum, scapula, skull, thoracic spine, sternum and 500 for femur and humerus.

The output of the hotspot detection is a set of ROIs (regions of interest) representing the hotspots in the image and a normalization factor which is used to set the initial maximum and minimum thresholds for image windowing.

Hotspot Pre-Selection

Hotspots may be classified as either included or excluded for pre-selection using a learning (data driven) approach based on artificial neural networks (ANNs). The ANNs may be tuned/trained on a training database with patients ranging from normal bone scans to bone scans with numerous and extensive hotspots.

Each hotspot in the training database is characterized using a set of features (measurements) relating to their size, location, orientation, shape and texture. These features are fed into the ANN, first during a training phase where the parameters of the ANN are set to maximize classification performance in a cross-validation study, and then in the actual software to classify a hotspot as included or excluded.

The pre-selection training analyzes hotspots and their immediate neighborhood in the images, making the classifier robust to large-scale differences in training materials. Therefore, the classifier is applicable to a wide range of input data. However, small difference in performance between cohorts can be expected. To avoid the influence of localization on the ANN parameters, separate networks can be constructed for different bone localizations. The set of input features for each of these ANNs then differ somewhat. For instance, the symmetry features only apply to localizations which have a natural symmetric counterpart.

In addition, hotspots in training sets are typically manually labeled as included or excluded by a medical expert trained in reading bone scans. The target labels can be verified by a second medical expert. In one example approach, the US and European procedural guidelines for bone scintigraphy are harmonized and the equipment used to obtain bone scans are the same in US and Europe. Furthermore, the criteria used to interpret bone scans for clinical trials, for example the Prostate Working Group 2 Criteria, are global. This is based on the common knowledge in the nuclear medicine community that variation in bone scan appearance due to cancer disease is much more pronounced than minor variation that can be measured in for example normal bone density between different races. The parameters of the ANNs are optimized such that the resulting classifier mimics the selection of a medical expert. To avoid bias towards the training set, a cross validation approach can be used.

In certain embodiments, while pre-selection saves time for the reader, all hotspots are reviewed and approved by the reader before a report is created.

ANN's as described herein can be implemented via one or more machine learning modules. As used herein, the term "machine learning module" refers to a computer implemented process (e.g., function) that implements one or more specific machine learning algorithms in order to determine, for a given input (such as an image (e.g., a 2D image; e.g., a 3D image), dataset, and the like) one or more output values. For example, a machine learning module may receive as input a 3D image of a subject (e.g., a CT image; e.g., an MRI), and for each voxel of the image, determine a value that represents a likelihood that the voxel lies within a region of the 3D image that corresponds to a representation of a particular organ or tissue of the subject. In certain embodiments, two or more machine learning modules may be combined and implemented as a single module and/or a single software application. In certain embodiments, two or more machine learning modules may also be implemented separately, e.g., as separate software applications. A machine learning module may be software and/or hardware. For example, a machine learning module may be implemented entirely as software, or certain functions of a CNN module may be carried out via specialized hardware (e.g., via an application specific integrated circuit (ASIC)).

E. Graphical User Interface and Image Display

Figures 9A, 9B:
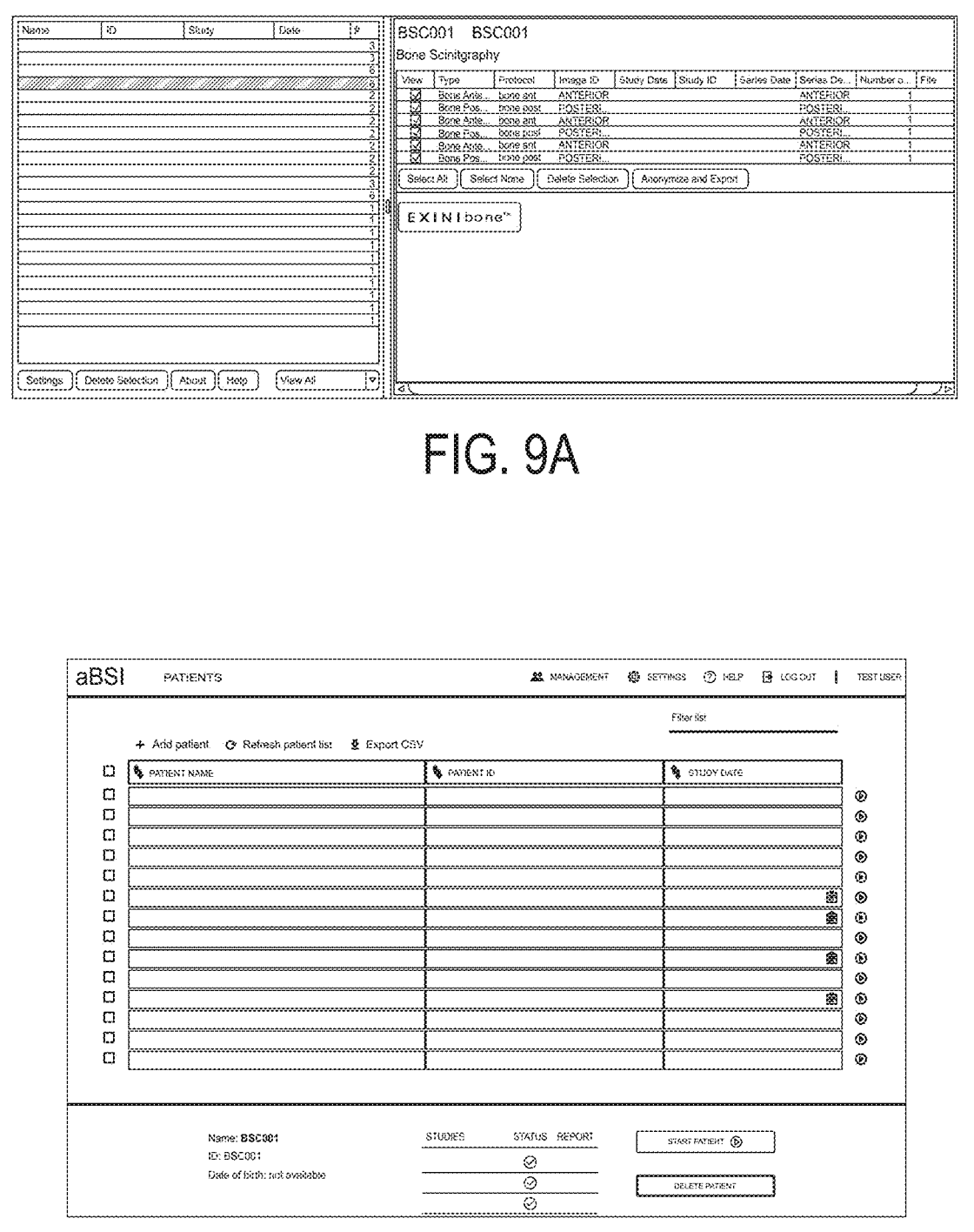
Figure 10A:
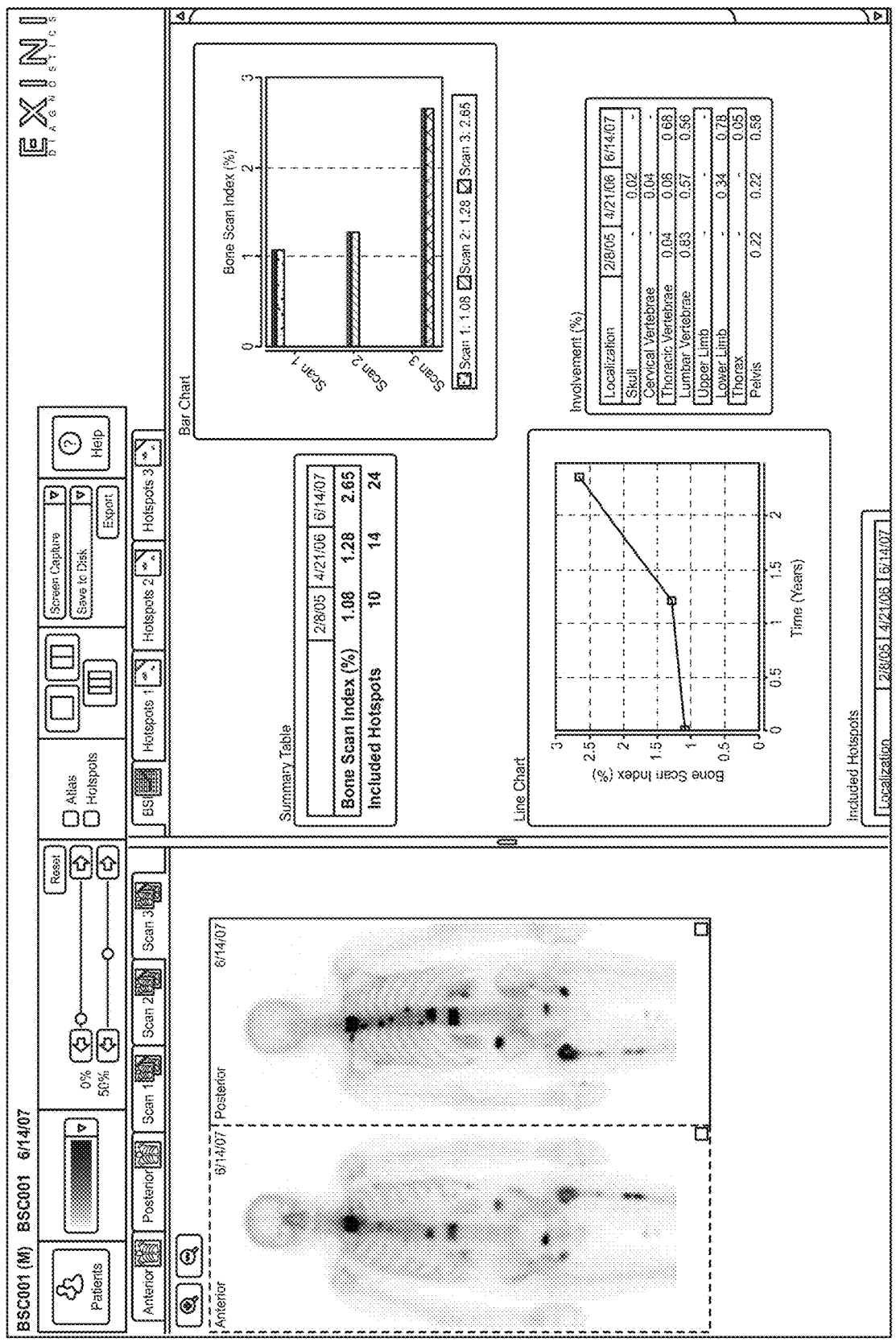
FIG. 10A is a screenshot of a GUI window for display and review of bone scan images and computed BSI values, according to an illustrative embodiment.
Figure 10B:
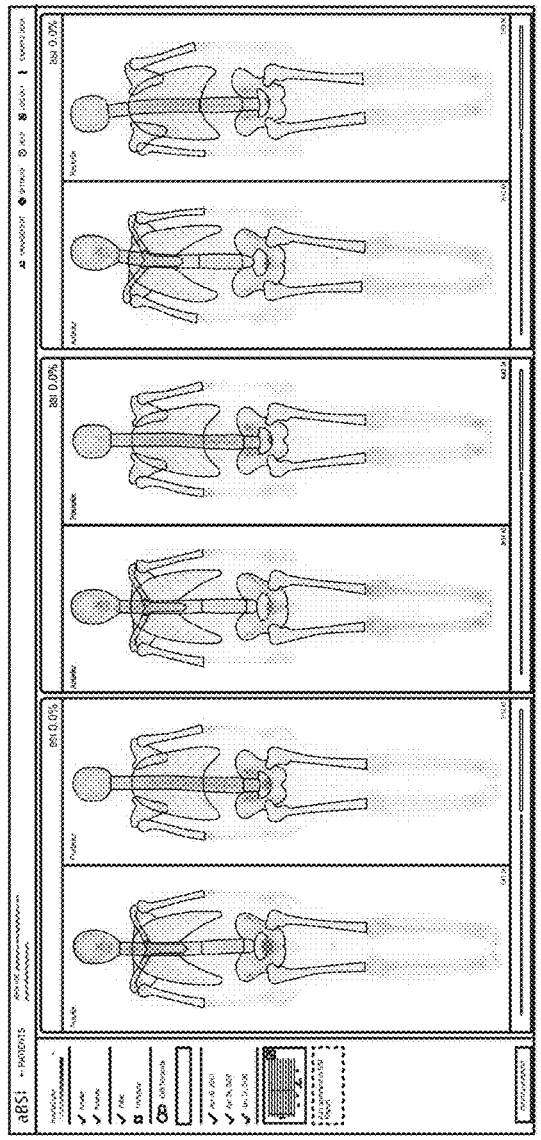
FIG. 10B is a screenshot of a GUI window for display and review of bone scan images and computed BSI values, according to an illustrative embodiment.
Figure 10D:
FIG. 10D is a screenshot of a portion of a GUI window showing colormap options for display of bone scan images, according to an illustrative embodiment.
Figure 10C:
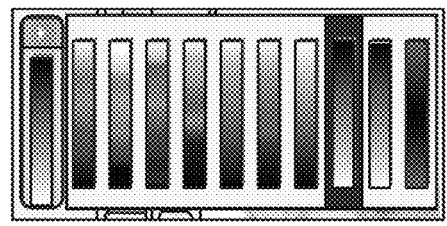
FIG. 10C is a screenshot of a portion of a GUI window showing colormap options for display of bone scan images, according to an illustrative embodiment.

In certain embodiments, the systems and methods described herein include a graphical user interface for review of patient data and images. The GUI may allow a user to review a list of patients and select patients for whom to review and analyze images. FIG. 9A and FIG. 9B show example GUI windows providing a listing of patients from which specific patients can be selected. Once a particular patient has been selected, a user may view bone scan images for that patient, and review automated analysis (e.g., detection and pre-selection of hotspots) using a GUI such as the GUIs shown in FIG. 10A and FIG. 10B. Bone scan images may be colorized using various colormaps. FIG. 10C and FIG. 10D show example colormaps that may be used.

Figure 11A:
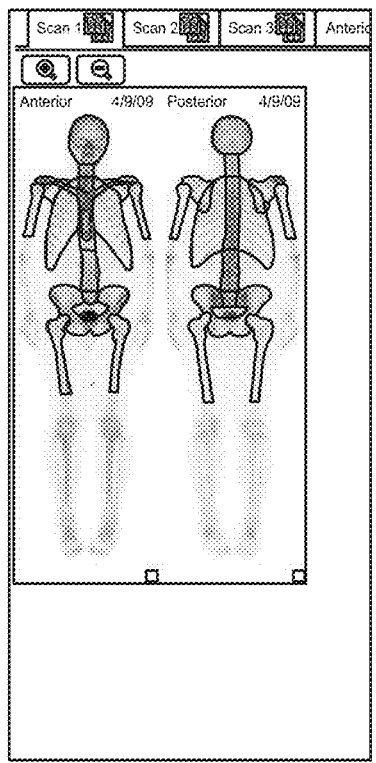
FIG. 11A is a screenshot of a portion of a GUI window for viewing bone scan images, according to an illustrative embodiment.
Figure 11B:
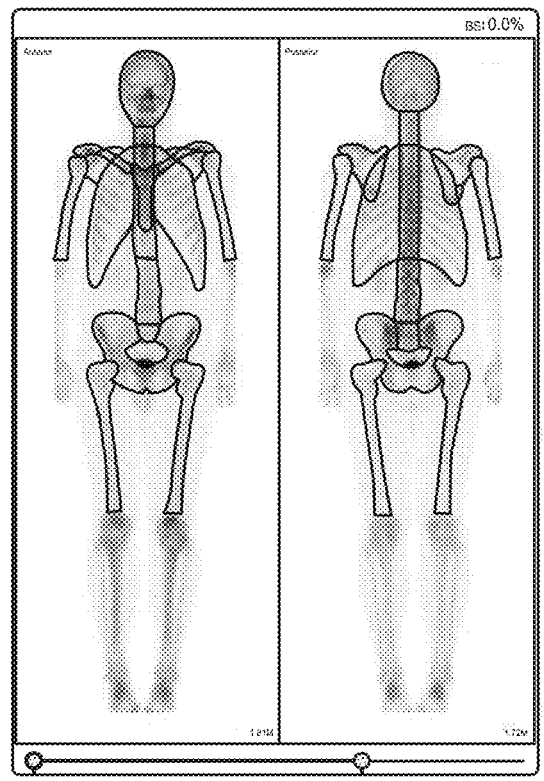
FIG. 11B is a screenshot of a portion of a GUI window for viewing bone scan images, according to an illustrative embodiment.
Figure 11C:
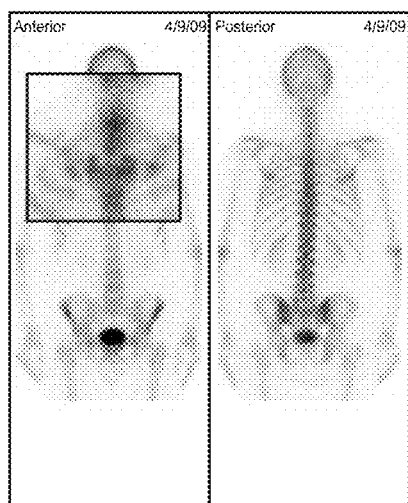
FIG. 11C is a screenshot of a portion of GUI window for viewing bone scan images illustrating a zoom feature, according to an illustrative embodiment.
Figure 11D:
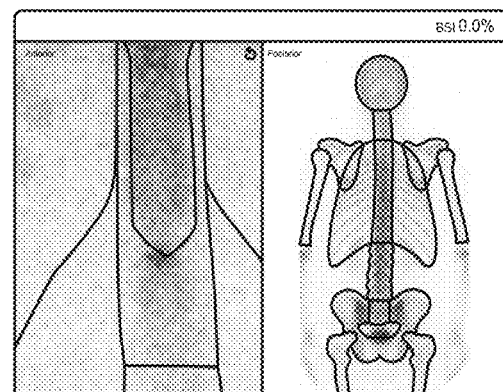
FIG. 11D is a screenshot of a portion of a GUI window for viewing bone scan images illustrating a zoom feature, according to an illustrative embodiment.

In certain embodiments, GUI systems in accordance with the approaches described herein facilitate viewing of images. For example, automatic adjustment of images to a screen size may be provided. FIG. 11A shows a GUI embodiment without this functionality, wherein a user clicks on zoom icons to vary the size of the images. FIG. 11B shows a screenshot of a GUI in which images are automatically sized to fill the screen vertically. FIG. 11C and FIG. 11D show two approaches for providing zoom functionality for viewing images in detail. In the embodiment shown in FIG. 11C magnification around a mouse pointer occurs when a scroll wheel button is clicked and held. In the embodiment shown in FIG. 11D, zoom an pan functionality using a mouse scroll wheel and click and drag operations are provided.

Figure 12B:
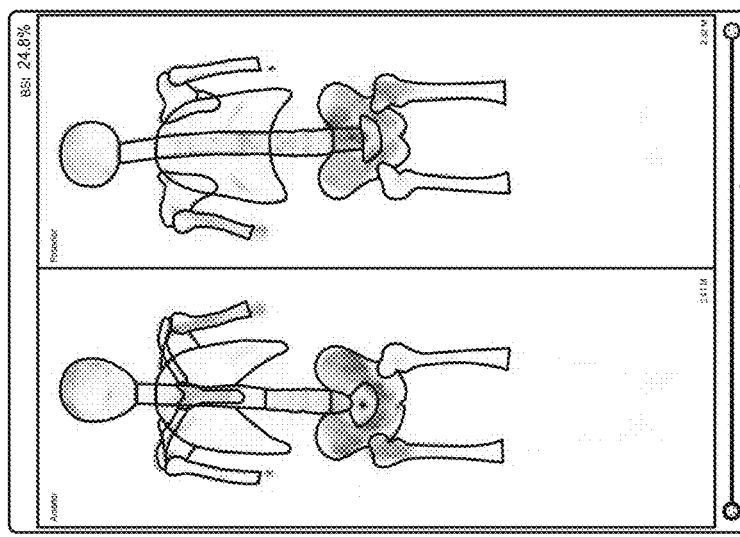
FIG. 12B is a screenshot of a GUI window displaying bone scan images using an intensity window that ranges up to a maximum intensity value, according to an illustrative embodiment.
Figure 12D:
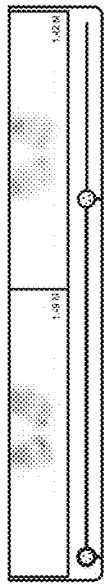
FIG. 12D is a screenshot of a portion of the GUI in FIG. 12B, showing another graphical control for adjustment of intensity window thresholds.
Figure 12A:
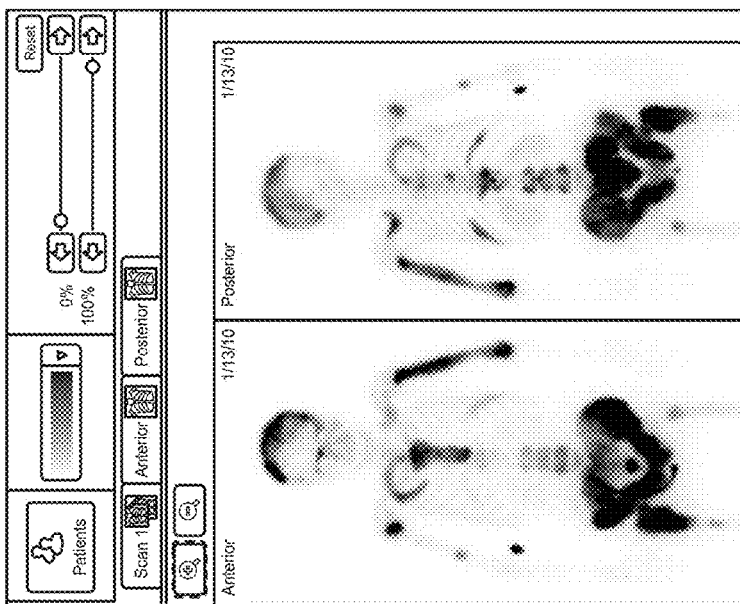
FIG. 12A is a screenshot of a GUI window displaying bone scan images, using an intensity window that only covers a limited range of intensity values.
Figure 12C:
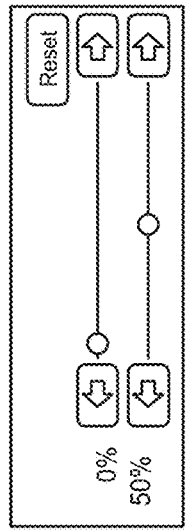
FIG. 12C is a screenshot of a portion of the GUI in FIG. 12A, showing a graphical control for adjustment of intensity window thresholds.
Figure 12F:
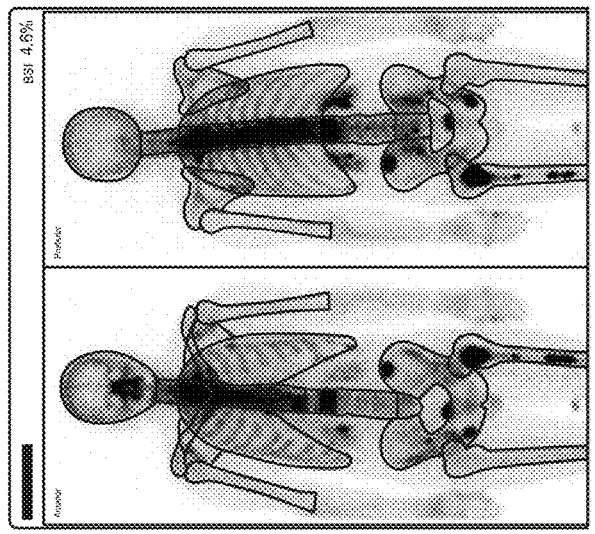
FIG. 12F is a screenshot of a GUI displaying anterior and posterior images of a bone scan image set, wherein a same intensity window is used for both images.

FIGS. 12A-12F illustrate intensity windowing approaches for display of images. In particular, FIGS. 12B and 12D show a GUI embodiment that implements a custom intensity windowing slider that facilitates a user adjustment of intensity window thresholds.

Figure 13B:
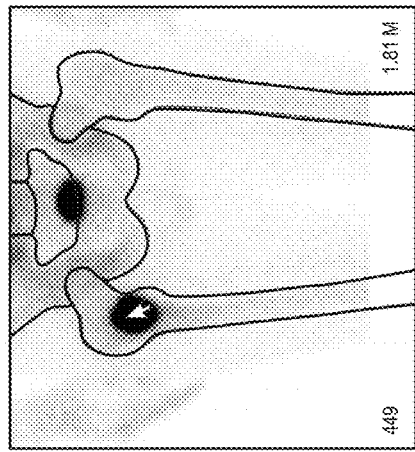
FIG. 13B is a screenshot of a GUI showing local intensity values at a location of a mouse pointer displayed in a corner (bottom left) of the GUI, according to an illustrative embodiment.
Figure 12E:
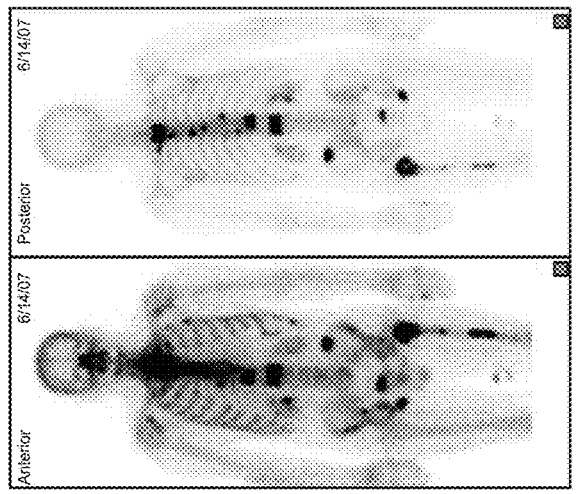
FIG. 12E is a screenshot of a GUI displaying anterior and posterior images of a bone scan image set, with each image displayed using a separate intensity window.
Figure 13A:
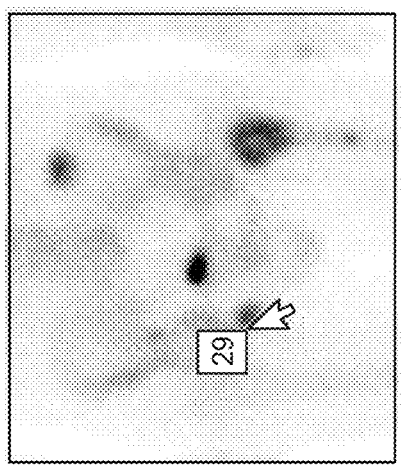
FIG. 13A is a screenshot of a portion of a GUI showing local intensity values displayed at a location of a mouse pointer, according to an illustrative embodiment.

FIG. 13A and FIG. 13B show screenshots of example GUI windows in which local intensity is displayed. In particular, in certain embodiments, local intensity is displayed when a user hovers a mouse pointer over an image. In the embodiment shown in FIG. 13A, a local intensity value is displayed at a location of the mouse pointer. In the embodiment shown in FIG. 13B, the intensity is displayed at the bottom left corner of the image, instead of next to the mouse pointer, where it then hides part of the image (e.g., accordingly providing for improved safety).

FIGS. 14A-14D show example GUI embodiments for displaying multiple bone scan images. In the embodiments shown in FIG. 14A and FIG. 14C, a tabular approach us used to allow a user to toggle through different bone scan image sets for different studies, or to toggle through anterior and posterior images. In the embodiments shown in FIG. 14B and FIG. 14C, checkboxes are used to toggle visibility of various images, allowing multiple images from different studies to be displayed alongside each other.

Figure 15A:
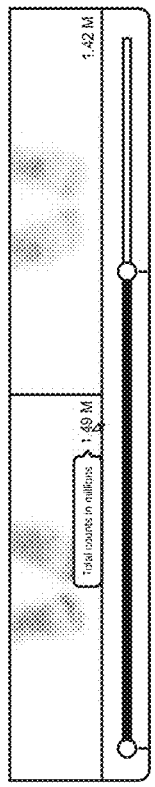
FIG. 15A is a screenshot of a GUI showing display of total image intensities and total skeletal intensities, according to an illustrative embodiment.
Figure 15B:
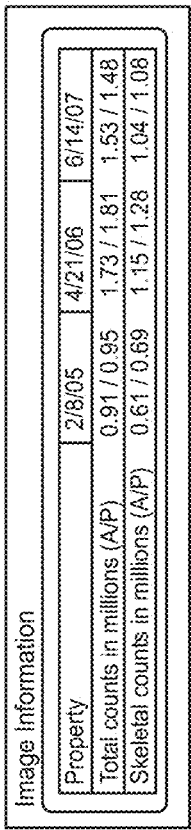
FIG. 15B is a screenshot of a GUI showing display of total image intensities, according to an illustrative embodiment.

In certain embodiments, embodiments of GUI tools for image analysis described herein may provide information useful for quality control. For example, total image intensities may be displayed. FIG. 15A is a screenshot of a GUI showing display of total image intensities and total skeletal intensities, according to an illustrative embodiment. In certain embodiments, such as the GUI shown in FIG. 15B, only total image intensities (and not total skeletal intensities) are displayed to provide a simpler user interface (e.g., to avoid confusion).

Figure 16A:
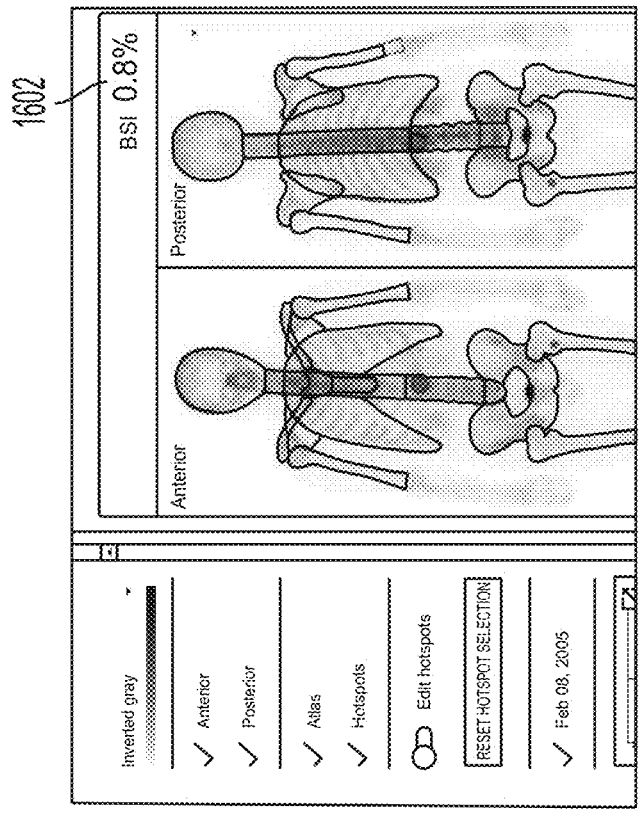
FIG. 16A is a screenshot of a GUI showing identified hotspots displayed as highlighted regions overlaid on bone scan images, according to an illustrative embodiment.
Figure 16B:
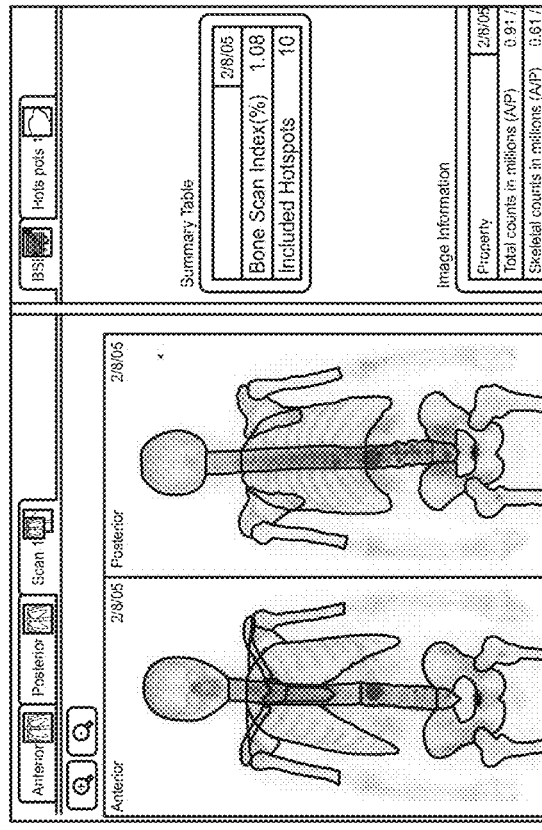
FIG. 16B is a screenshot of a GUI showing identified hotspots displayed as highlighted regions overlaid on bone scan images, according to an illustrative embodiment.
Figure 18B:
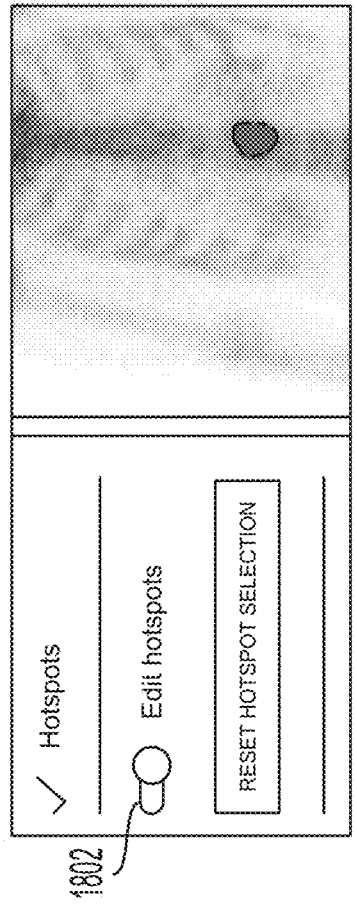
FIG. 18B is a screenshot of a GUI showing a toggle graphical control for allowing user selection of hotspots to include and/or exclude, according to an illustrative embodiment.
Figure 18A:
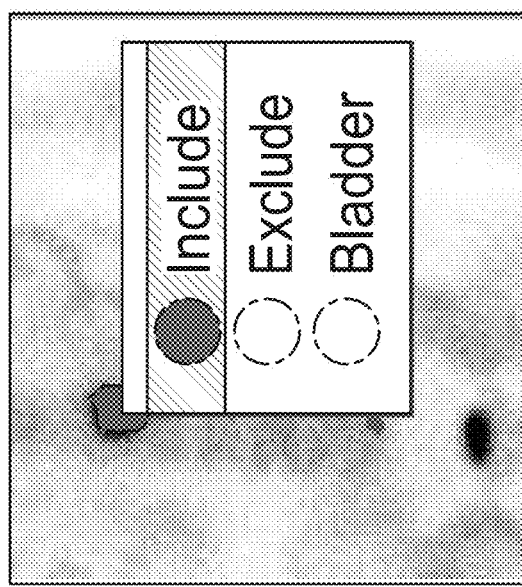
FIG. 18A is a screenshot of a GUI showing popup graphical controls for inclusion and/or exclusion of automatically identified hotspots, according to an illustrative embodiment.
Figure 18C:
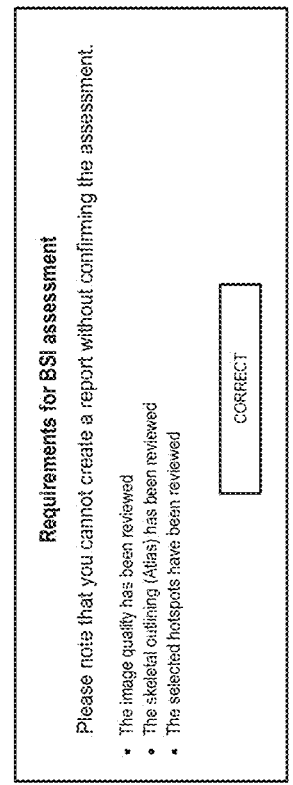
FIG. 18C is a screenshot of a GUI showing a window prompting a user to follow a quality control workflow before generating a report, according to an illustrative embodiment.

The GUI tools for reviewing bone scan images may show graphical indications of detected (e.g., and pre-selected) hotspots overlaid on bone scan images, for example as shown in FIG. 16A and FIG. 16B. In certain embodiments, a table of hotspots, as shown in FIG. 17A, is also displayed. In certain embodiments, the GUI tools described herein allow a user to select or deselect a pre-selected hotspot for inclusion in a final set of selected hotspots used to compute a BSI value. The GUI may display the resultant BSI value 1602 above an image, allowing a user to observe its changes (compare 1704a with 1704b) with selection and/or deselection of various hotspots (1702a and 1702b), as shown in FIGS. 17B and 17C. Various graphical control approaches may be used to allow a user to select pre-selected hotspots to include or exclude. For example, FIG. 18A shows a pop-up control that appears following a user right-click operation. FIG. 18B shows a toggle switch 1802 ("Edit hotspots") that can be turned on and off. Once the toggle switch is turned on, the user clicks on various hotspots to select or deselect them. In certain embodiments, the GUI tools may include safety/quality control features, such as the pop-up window shown in FIG. 18C that prompts a user to verify quality control requirements before a report is generated.

In certain embodiments, once BSI values are computed for various studies, they are displayed for user review. For example, computed BSI values may be displayed in a table, as shown in FIG. 19A. In certain embodiments, computed BSI values for different studies are displayed above the displayed bone scan images for their corresponding studies, as shown in FIG. 19B. Charts showing time evolution of computed BSI values may also be displayed, as shown in FIGS. 20A and 20B. Additional information pertinent to computed BSI values may also be displayed. FIG. 21 shows a screenshot of a GUI providing a table listing number of hotspots in particular anatomical regions used for computation of BSI values in different studies, according to an illustrative embodiment. In certain embodiments, the systems and methods described herein provide for automated report generation. FIG. 22A and FIG. 22B show example auto-generated reports.

F. Improved Image Processing Approaches

In certain embodiments, the systems and methods described herein include improvements to one or more of the image processing steps shown in FIG. 6.

i. Skeletal Segmentation

Figure 23:
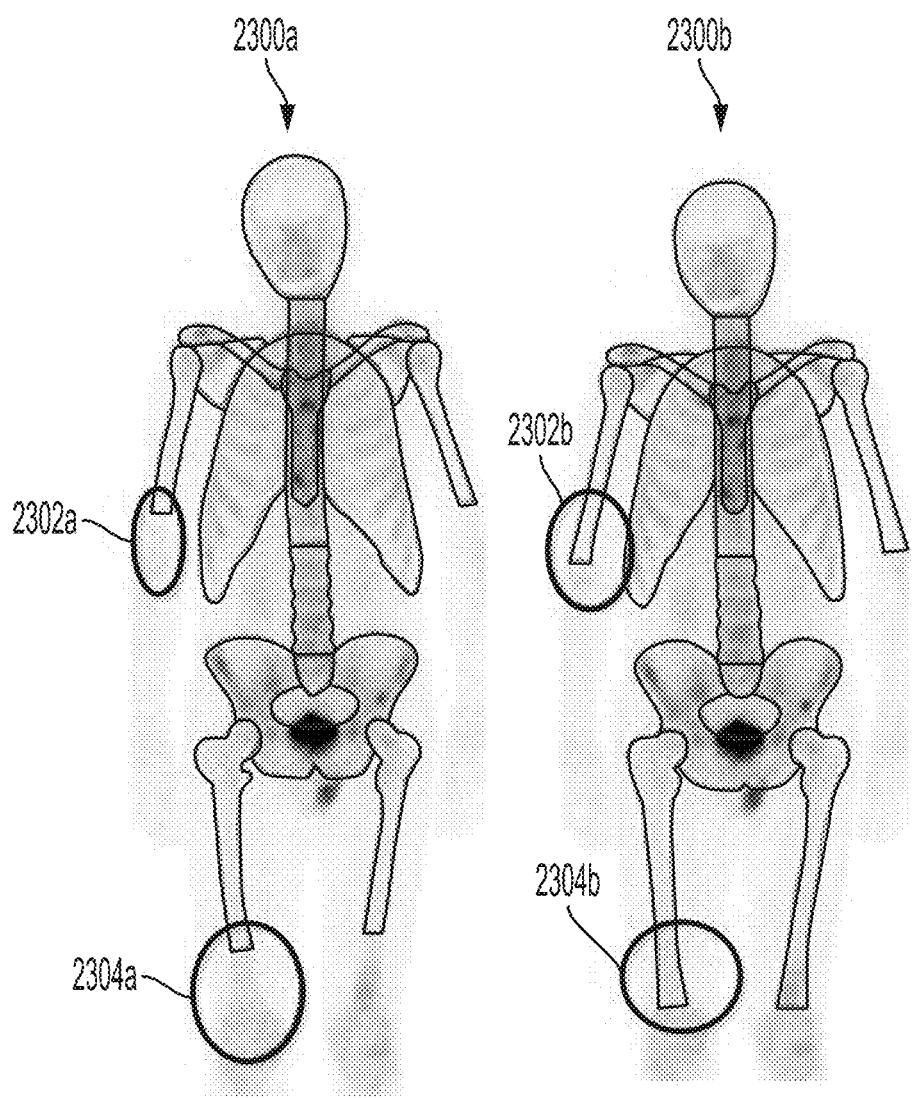
FIG. 23 a set of bone scan images with atlas-based skeletal segmentation overlaid, comparing use of a limited atlas (left) with a full-length atlas (right), according to an illustrative embodiment.

As described herein, a skeletal atlas image set may be used for image segmentation. The skeletal atlas image set includes a pair of template bone scan images (anterior and posterior) representing a typical normal bone scan, and a manual outlining of 31 skeletal regions. These regions are warped to fit a current patient image to be analyzed. In certain embodiments, a limited atlas with skeletal identifications that only cover three-quarters of a femur and a humerus is used. In certain embodiments, an improved, full-length atlas that includes skeletal region identifications covering the entire femur and humerus is used. FIG. 23 shows a set of bone scan images with atlas-based skeletal segmentation overlaid, comparing use of a limited atlas 2300a (left) with a full-length atlas 2300b (right). As shown in FIG. 23, the limited atlas 2300a only includes a three-quarters or less of the humerus 2302a and femur 2304a, whereas the full length atlas includes well over three quarts of the length of the humerus 2302b and femur 2304b. Use of the full-length atlas can increase stability of skeleton segmentation. In particular, the increased atlas allows knees and elbows to be utilized as references during registration. Such reference points, with clear contrasts, are beneficial for image analysis and provide improved stability. The increased atlas also allows for detection of hotspots further out in the limbs.

ii. Hotspot Detection Thresholds

As described herein, an initial set of candidate hotspots is found using thresholding of image intensities. In certain embodiments, a global and fixed threshold is used, such that a same value is used across all skeletal regions of interest and all images. Another, improved, approach sets regional thresholds that vary across different skeletal regions of interest. For example, this approach allowed a reduced threshold to be used for femur and humerus regions (e.g., decreased from 650 to 500) to increase detection sensitivity. Femur and humerus regions show less uptake in bone scan images than other skeletal regions. Accordingly, lower thresholds can be used for these regions to achieve a similar level of sensitivity as for the rest of the body. Setting individual thresholding values for different skeletal region allows this functionality and leads to increased detection of lower intensity hotspots in these skeletal regions.

Figure 24:
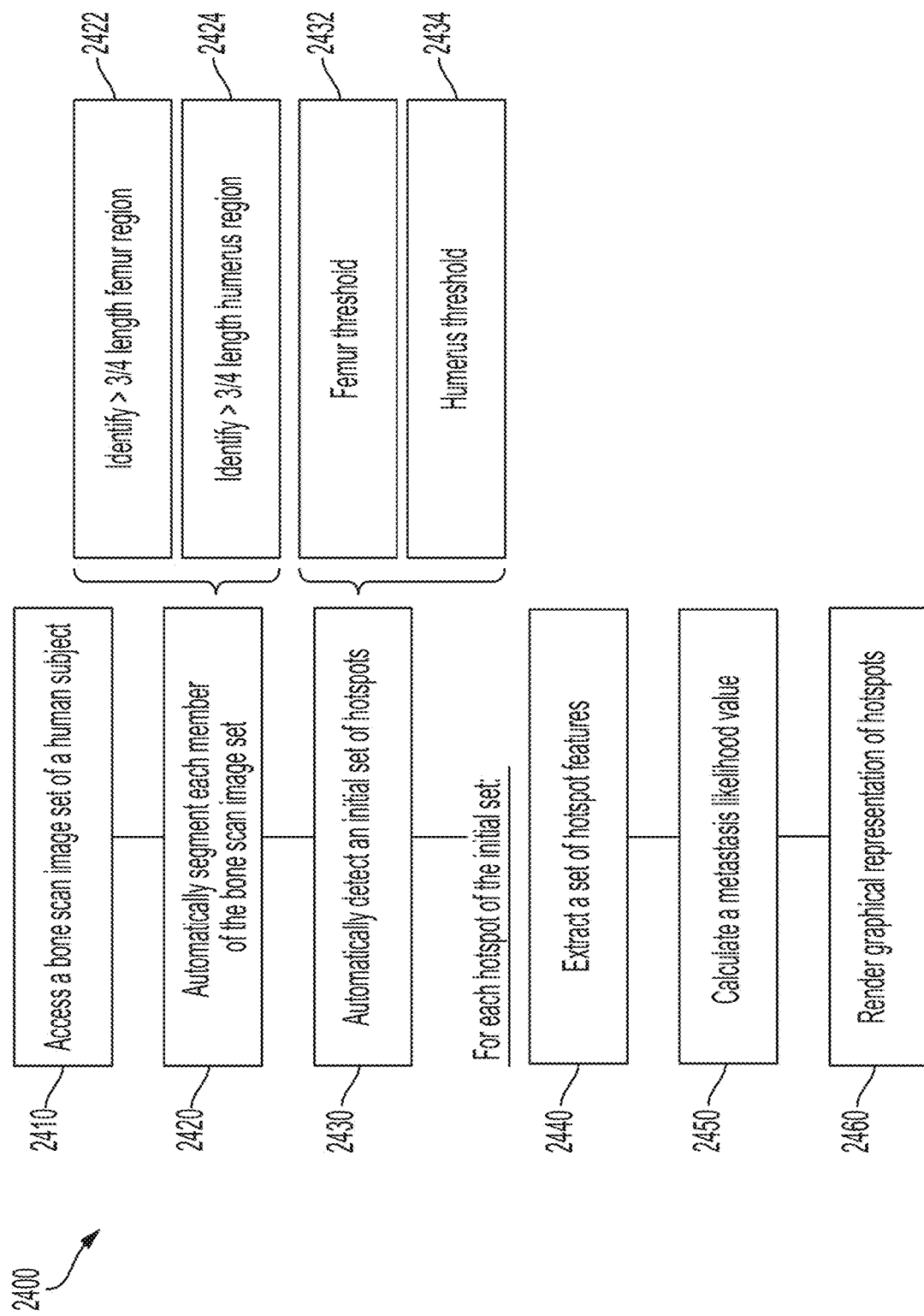
FIG. 24 is a block flow diagram of an example process for improved image analysis via segmentation of full length humerus and/or femur regions and enhanced hotspot detection therein, according to an illustrative embodiment.

FIG. 24 shows an example process 2400 for lesion marking and analysis using the above-described improved segmentation and region-dependent threshold approaches. In the example process 2400, a bone scan image set for a human subject is accessed 2410. Each member image of the bone scan image set is automatically segmented 2420 to identify skeletal regions of interest, including a femur region corresponding to greater than three quarters of the length of the femur of the subject 2422 and/or a humerus region corresponding to greater than three-quarters of the length of the humerus of the subject 2424. The identified skeletal regions of interest are then analyzed to automatically detect an initial set of hotspots 2430. As described herein, this step of automatically detecting hotspots may comprise applying thresholding operations that use region dependent thresholds—i.e., whose values are not uniform, and differ between one skeletal region and another, to each skeletal region of interest. In particular, lower valued thresholds for the femur and/or humerus regions (2432 and 2434, respectively) may be used to enhance detection sensitivity in the femur and/or humerus regions, thereby accounting for reduced agent (e.g., radiopharmaceutical) uptake therein.

Once the initial set of hotspots is detected a set of hotspot features is extracted for each hotspot 2440 and used to calculate, for each hotspot, a metastasis likelihood value 2450. The detected hotspots can be rendered for graphical display to a user 2460, in certain embodiments along with additional information such as the calculated likelihood values. Hotspots may be filtered (pre-selected) based on the calculated likelihood values, for inclusion in a first subset, to either be presented to the user and/or used for calculation of risk indices such as BSI values. A user may review the detected hotspots—e.g., the initial hotspot set, or the first subset comprising the filtered hotspots, via the graphical display, and confirm or reject hotspots for inclusion in a second, final subset. This final subset may then be used for calculating risk index values, thereby incorporating user expertise into the decision making process.

In certain embodiments, a global dynamic threshold adjustment is used. This method checks the resulting BSI value and fine tunes a global threshold scaling factor to accommodate for high burden disease. The scaling is computed according to the formula, $$t = t_i * \max\left(0.4, 1 - \frac{3b}{1 + e^{-70(b-0.12)}}\right); \quad \text{(Eq. 1)}$$

$$\text{where } b = \frac{\text{total area of all hotspots}}{\text{total area of skeleton}},$$

where $t_i$ is an original, preliminary regional threshold. Fine tuning of the global threshold scaling increases the linearity in high burden disease cases while leaving low burden disease untouched. This global scaling factor approach thus increases the useful range for BSI calculations.

In particular, in certain embodiments the global scaling factor approach is a data-driven approach accounts for accounts for errors wherein BSI values can be underestimated at higher levels of disease—i.e., high levels of metastasis. These errors were discovered using a simulation system that allows bone-scan images to be simulated for a patient with any (e.g., selected) degree of disease. The simulation system produces realistic bone-scan images, accounting for specific camera and examination parameters as well. Realistic bone-scan images can therefore be produced for known specific input parameters, such that ground truth in terms of lesion volume, skeletal volumes, and, therefore, BSI value are known. Accordingly, this approach allows for BSI values computed via the image analysis approaches described herein to be compared with and checked against known ground truth BSI values determined from the image simulation input parameters. Running a large number of simulations with varying degree of disease burden demonstrated that a previous system, which did not use the global threshold scaling approach described herein, was underestimating BSI values for higher disease burden in a non-linear fashion. The form of the non-linear function used for the global threshold scaling factor in Equation 1 is based on the pattern of errors observed in the simulation study, so as to correct for the observed non-linear under estimation of computed BSI values.

Figure 25A:
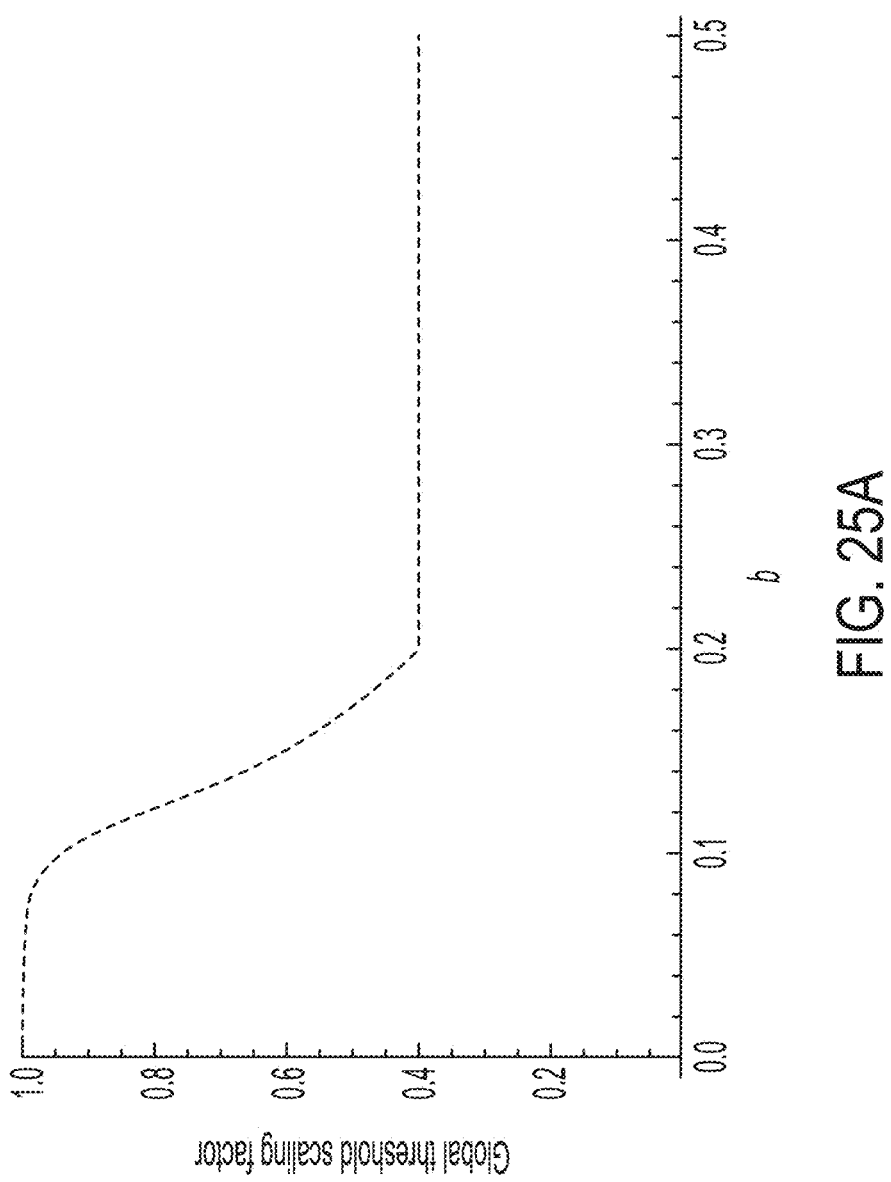
FIG. 25A is a graph showing variation in a global threshold scaling factor as a function of a measure of disease burden, according to an illustrative embodiment.

FIG. 25A is a graph of the scaling factor as a function of b. As shown in the graph, multiplying the preliminary thresholds by the global threshold scaling factor decreases the thresholds as disease burden—measured by the hotspot area fraction, b—increases. The decreased (adjusted) thresholds result in larger regions identified as hotspots, thereby increasing computed BSI values, which measure the overall fraction of a patient's skeleton occupied by hotspots. In this manner, using the global threshold scaling factor to adjust thresholds used for hotspot detection corrects for the observed underestimation in computed BSI values at high levels of disease.

Figure 25B:
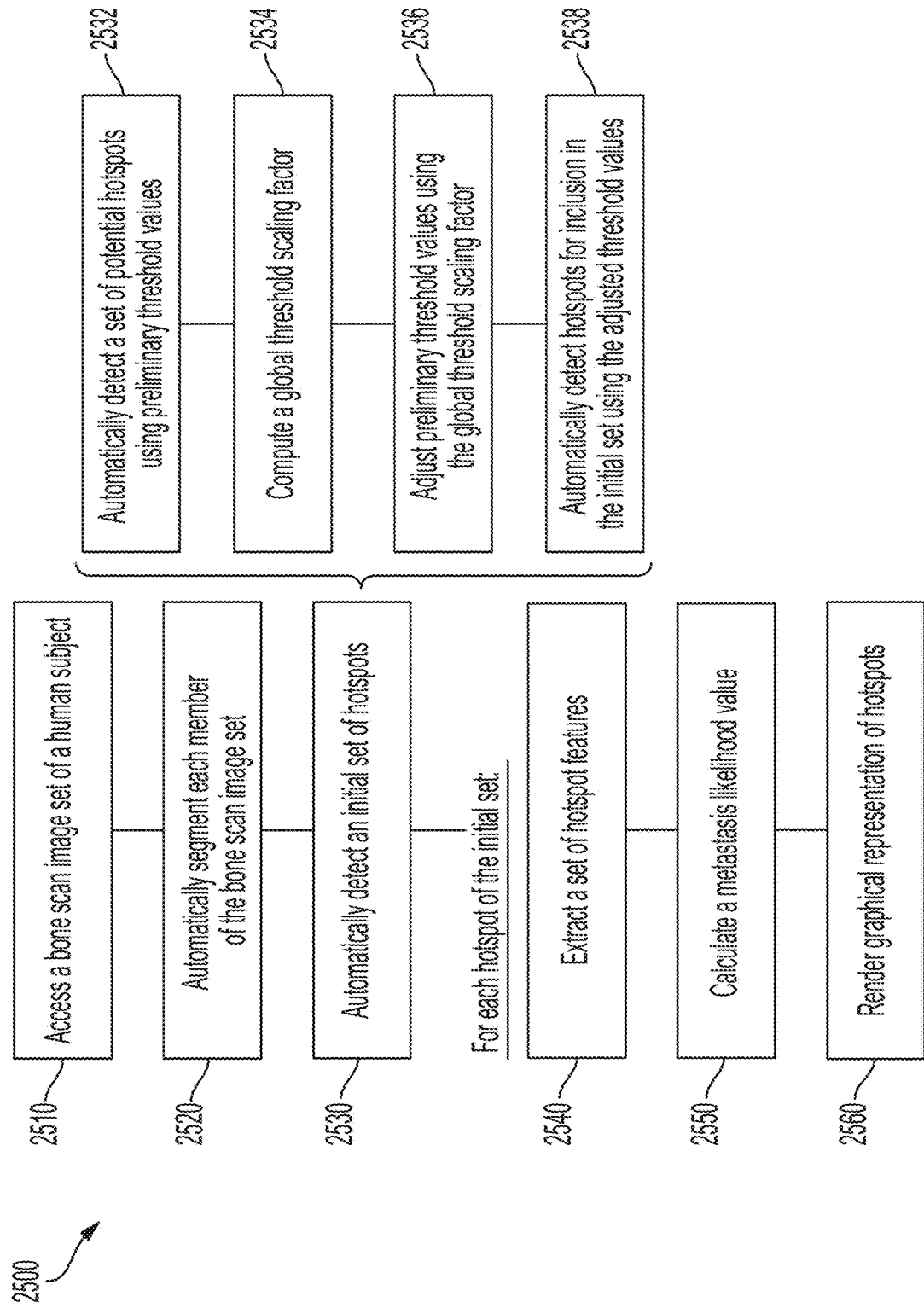
FIG. 25B is a block flow diagram of an example process for improved image analysis using a global threshold scaling approach, according to an illustrative embodiment.

FIG. 25B shows an example process 2500 for using a global threshold scaling approach for detecting hotspots. In a first step 2510, a bone scan image set for a human subject is accessed. The bone scan image set is automatically segmented 2520 to produce a set of annotated images comprising identifications of skeletal regions of interest. In certain embodiments, segmenting may comprise identification of a full length femur and/or humerus, as described with respect to FIG. 24 above. In another step 2530, an initial set of hotspots is automatically detected. In this hotspot detection step 2530, a set of potential hotspots is first detected, using preliminary threshold values 2532. The set of potential hotspots is then used to compute a global threshold scaling factor 2534, for example as described herein, which is then used to adjust the preliminary threshold values 2536. These adjusted threshold values are then used to automatically detect hotspots for inclusion in the initial hotspot set 2538. Similar to process 2400, once the initial set of hotspots is detected a set of hotspot features is extracted for each hotspot 2540 and used to calculate, for each hotspot, a metastasis likelihood value 2550. The detected hotspots can be rendered for graphical display to a user 2560.

iii. Hotspot Pre-Selection

As described herein, hotspots are classified to determine if they should be pre-selected or not. In certain embodiments, hotspot classification is carried out via a two-step process. In certain embodiments, a first step classifies a particular hotspot using local features of the particular hotspot, but not the rest of the image, for example if the patient had no other or many other hotspots. In certain embodiments, a second step is included to incorporate global information about hotspots in the rest of the image.

Clinical experience shows that hotspot selection depends on the rest of the image. The probability of a hotspot being selected is higher if there are many other hotspots and lower if it is the only hotspot. Therefore, using only a single step process can result in underestimation of the BSI value in patients with many hotspots. Using the two-step process can improve performance in patients with many hotspots and high BSI. Selection of hotspots using global hotspot features may be performed using a machine learning module. For example, in certain embodiments, while a first machine learning module is used to compute the metastasis likelihood values for each hotspot, a second machine learning module (e.g., implementing a different ANN) may receive the calculated likelihood values along with the global hotspot features to determine whether a hotspot should be included in the subset of pre-selected hotspots.

Figure 26:
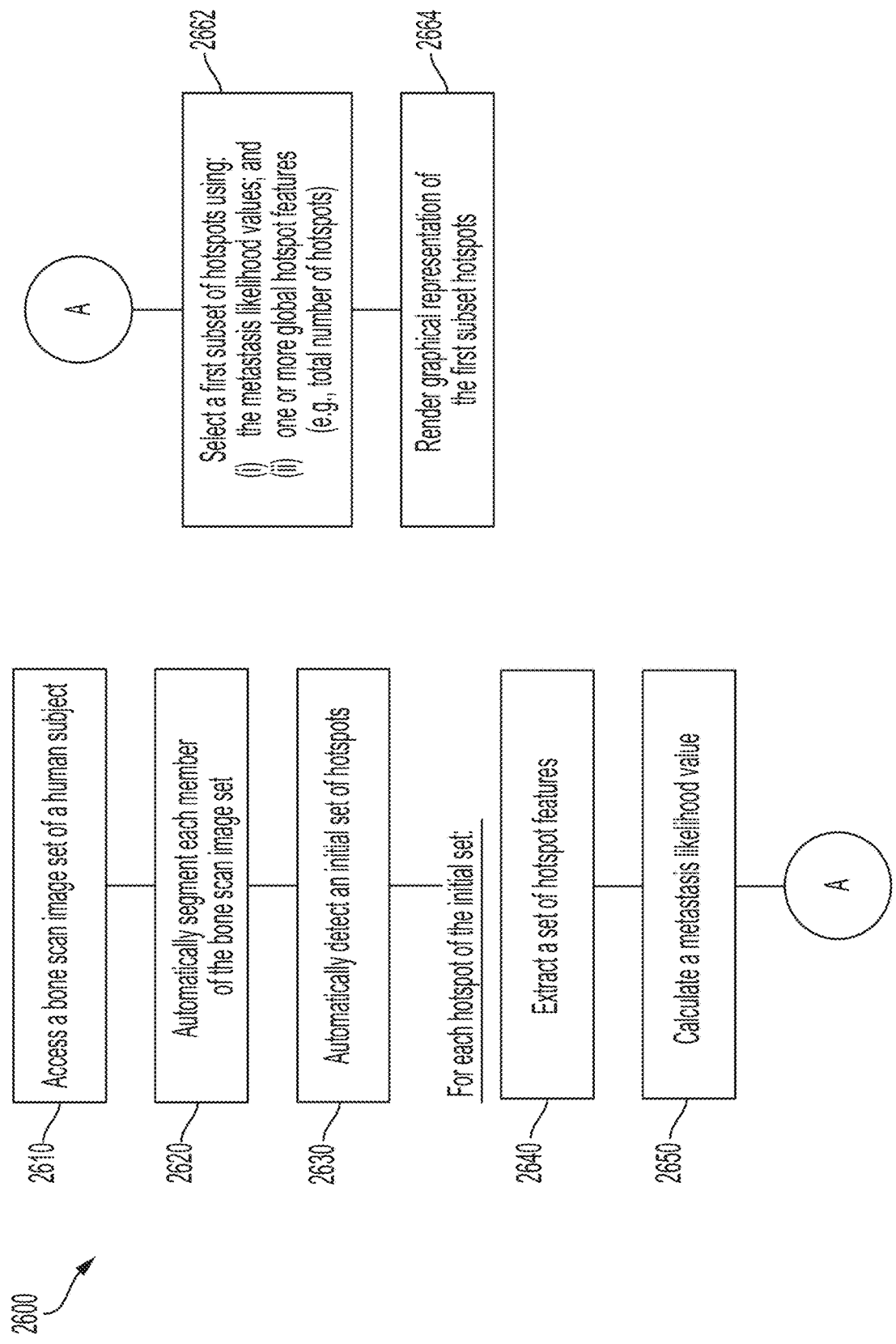
FIG. 26 is a block flow diagram of an example process for pre-selecting a first subset of hotspots using global hotspot features, according to an illustrative embodiment.

FIG. 26 shows an example process 2600 for hotspot pre-selection using global hotspot features. Process 2600 begins with accessing a bone scan image set 2610, automatically segmenting images (members) of the bone scan image set to identify skeletal regions 2620 and automatically detect an initial hotspot set 2630. Segmentation step 2620 and hotspot detection step 2630 may utilize the improved segmentation approach of process 2400 and/or the global threshold scaling approach of process 2500. Hotspot features are extracted for each hotspot 2640 and used to calculate, for each hotspot, a metastasis likelihood value 2650. In process 2600, the metastasis likelihood values are used, along with global hotspot features, to pre-select a first subset of the initial hotspots 2662. This first subset thereby filters hotspots, allowing a smaller, targeted set of hotspots that have been automatically determined to be likely cancerous lesions to be displayed to the user 2664.

iv. Atlas Weights

Figure 27:
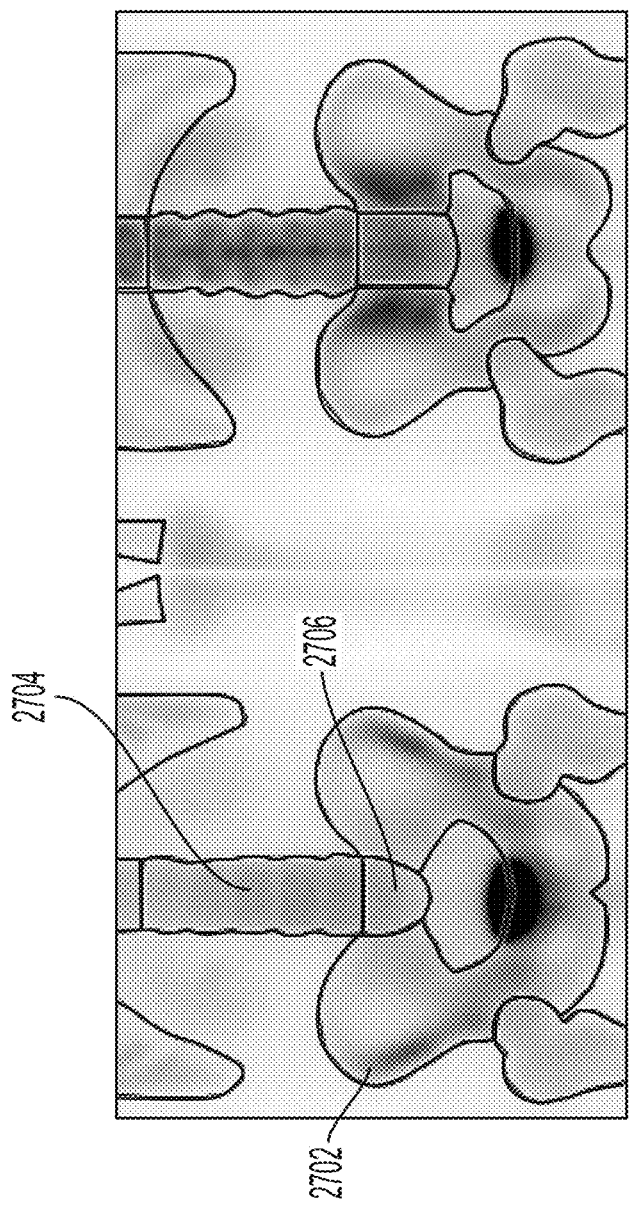
FIG. 27 is a set of two bone scan images, showing portions about the sacrum, pelvic, and lumbar spine regions, according to an illustrative embodiment.

In certain embodiments, correction factors for the sacrum, pelvis and lumbar spine regions are adjusted so that hotspots of equal area correspond to a more uniform measurement of BSI involvement. In certain embodiments, without such adjustment, the sacral region differs significantly from the neighboring pelvic and lumbar regions. FIG. 27 shows these regions—the sacral region 2706, pelvic region 2702, and lumbar region 2704—as outlined in the skeletal atlas.

To calculate a BSI value, the fraction of the total skeleton for each selected hotspot is calculated, and the BSI value is calculated as the sum of all such fractions. For each hotspot, the fraction is calculated as follows. The hotspot size divided by the size of the corresponding skeletal region (e.g., skull, ribs, lumbar vertebra, pelvis) obtained from the segmentation of the skeleton and multiplied by a weight fraction constant of the present skeletal region with respect to the weight of the total skeleton. These constants, one for each skeletal region, can be determined based on International Commission on Radiological Protection (ICRP) publication 23.

Involvement is calculated using the formula $$inv = \frac{\text{area (hotspot)}}{\text{area (region)}} icrp \cdot c,$$

where c is a correction factor that collects a number of properties, such as if hotspots are typically visible in both the anterior and posterior image. Before the adjustment to the correction factor described here, this constant was 1.0 for all three regions.

Figure 28:
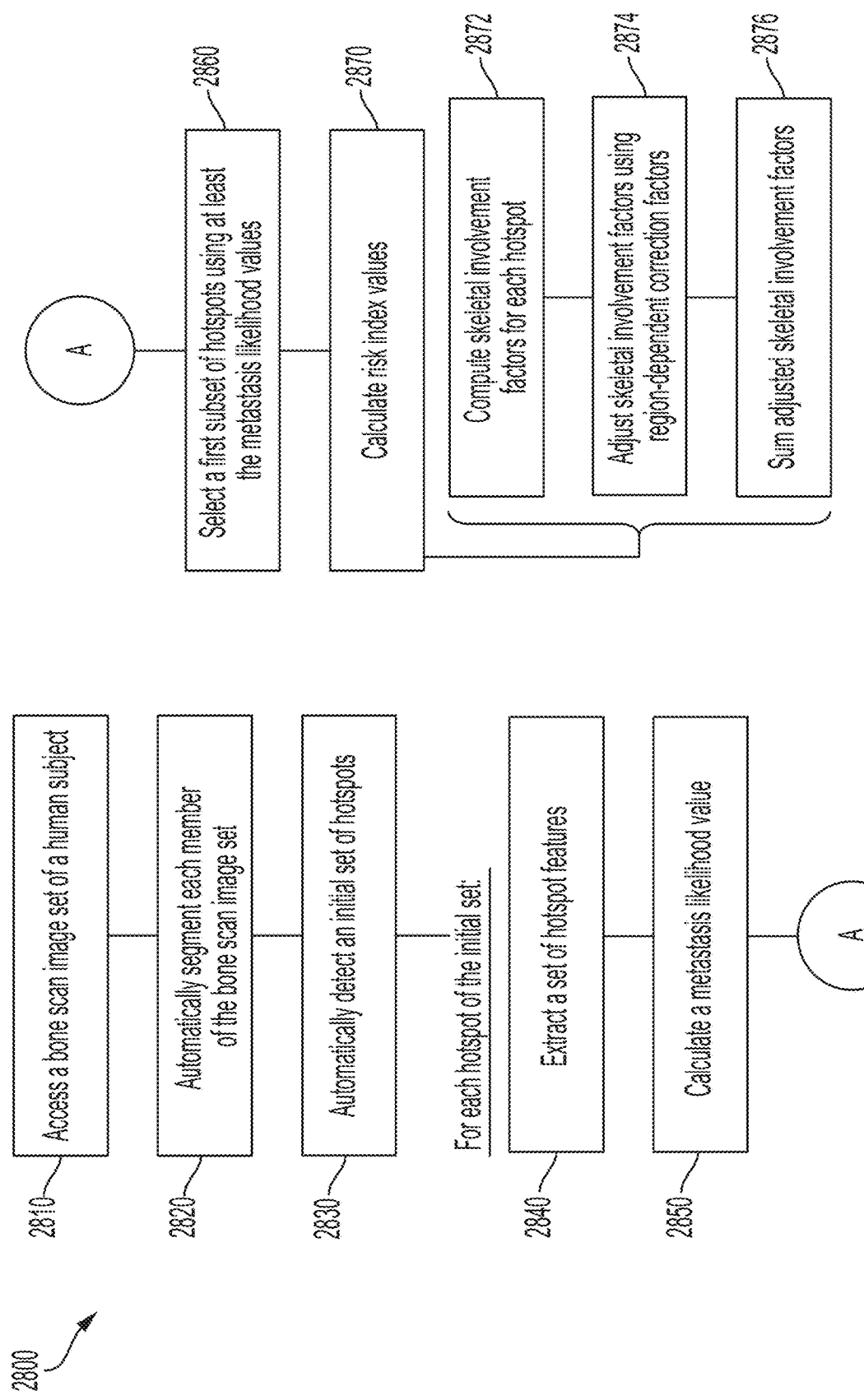
FIG. 28 is a block flow diagram of an example process for calculating risk index values based on skeletal involvement factors and region dependent correction factors that account for potential errors in hotspot localization, according to an illustrative embodiment.
Figure 29:
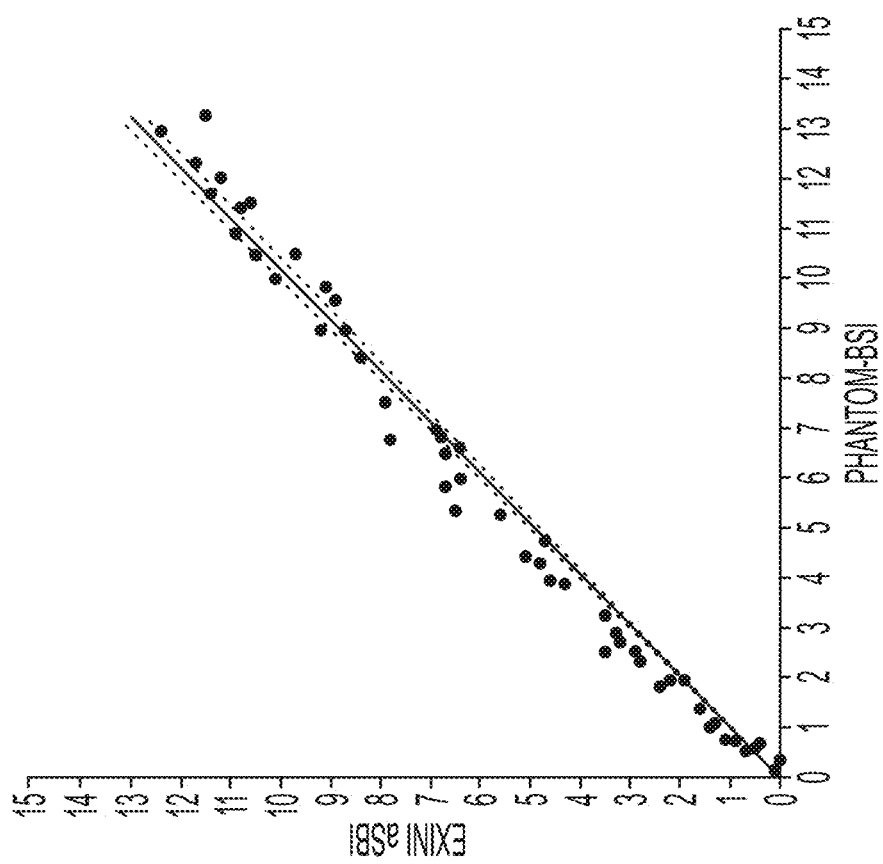
FIG. 29 is a graph comparing BSI values calculated via an automated software-based approach in accordance with the aspects and embodiments described herein with a known analytical standard.
Figure 30:
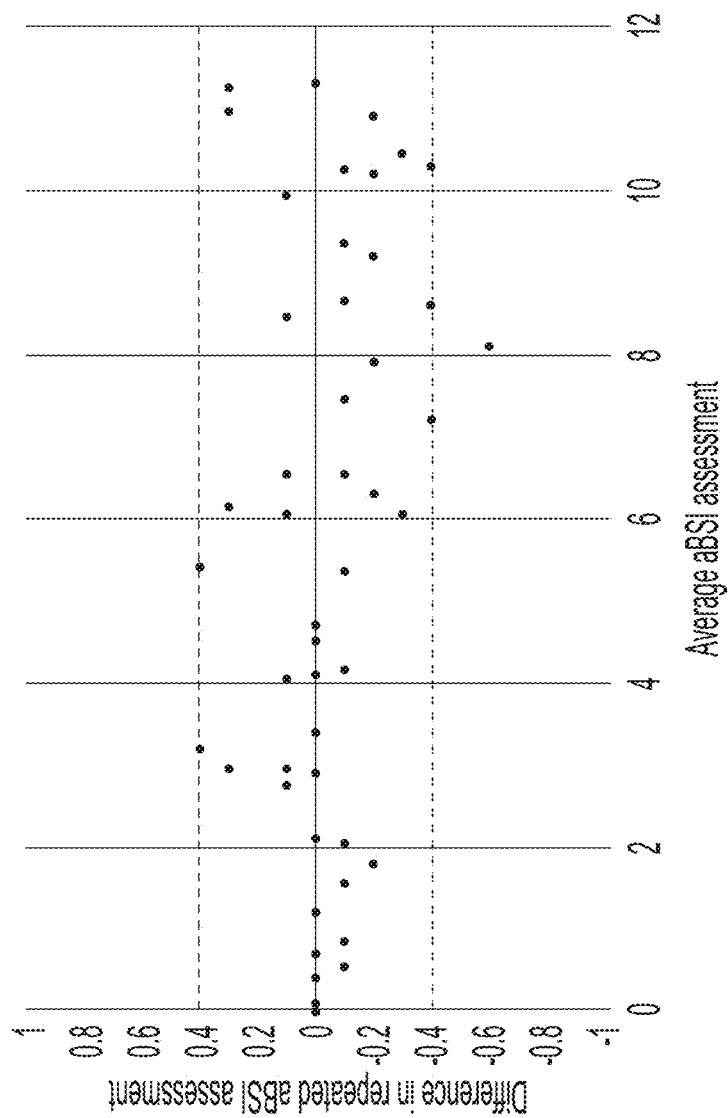
FIG. 30 is a graph showing reproducibility in automated BSI values from scan-to-scan for 50 simulated phantoms.
Figure 31:
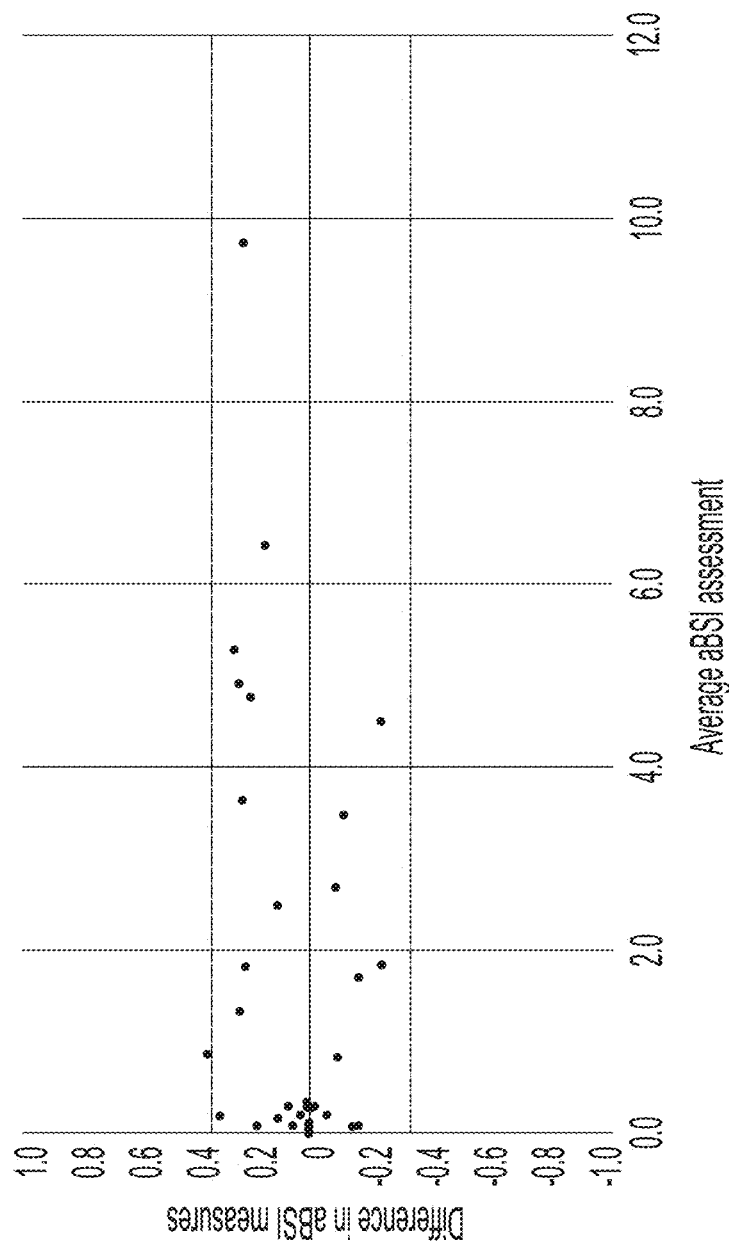
FIG. 31 is a graph showing reproducibility in automated BSI values from scan-to-scan for 35 metastatic patients.
Figure 32A:
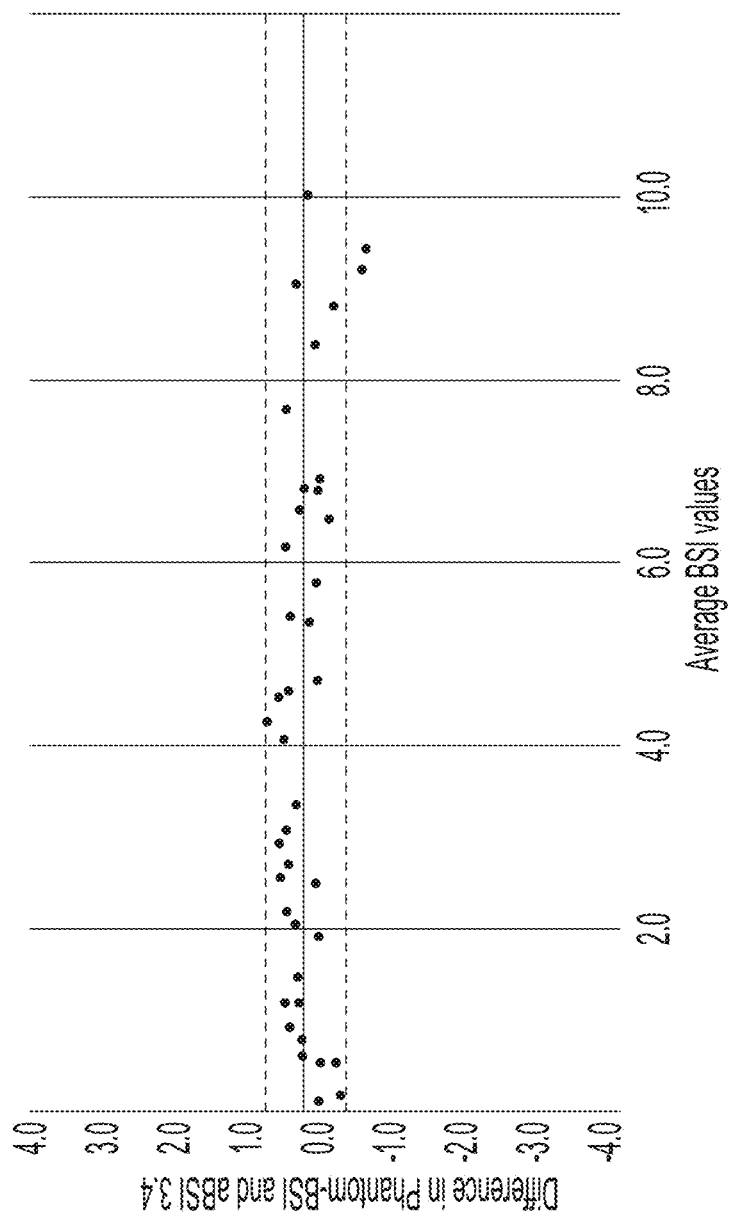
FIG. 32A is a graph showing performance of a current image analysis software version that employs embodiments in accordance the improvements described herein.
Figure 32B:
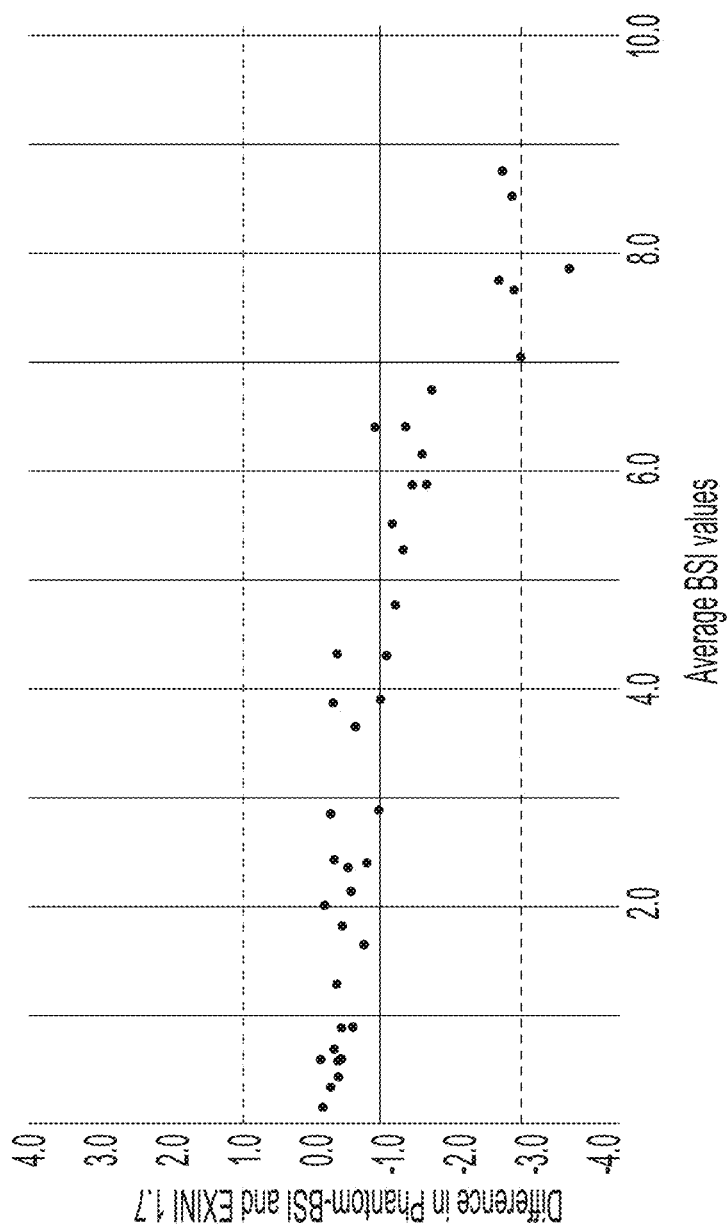
FIG. 32B is a graph showing performance of a previous image analysis software version, according to an illustrative embodiment.

In certain embodiments, this basic method works well in most skeletal regions, but not well in the sacrum region with surrounding pelvic and lumbar areas. The sacrum is a complex 3-dimensional structure and with a 2-dimensional bone scan it is difficult to separate hotspots in different regions and to localize a hotspot to the correct region. Depending on the assigned localization of a hotspot (e.g., to pelvis, lumbar column or sacrum), hotspots of similar size can have large differences in terms of their contribution to the computed BSI fraction. To reduce these differences, the coefficient c in the formula above is adjusted for sacrum such that the difference from the pelvic towards the lumbar region is more gradual. In particular, the correction factor is adjusted such that the ratio $$\frac{icrp \cdot c}{\text{area (region)}}$$

describes this gradual change. The value of c is adjusted accordingly as $c_{sacrum,anterior}=0.16$ and $c_{sacrum,posterior}=0.28$ such that fractional BSI values in the sacrum lie between those in the pelvic and lumbar regions FIG. 28 shows an example process 2800 for utilizing the correction factors described herein to adjust skeletal involvement factors and compute risk index values therefrom. Process 2800 includes steps of accessing a bone scan image 2810, automatically segmenting the bone scan image 2820 to identify skeletal regions, automatically detecting an initial set of hotspots 2830, and extracting hotspot features 2840 and calculating metastasis likelihood values for each hotspot 2850. Segmentation step 2820 and hotspot detection step 2830 may utilize the improved segmentation approach of process 2400 and/or the global threshold scaling approach of process 2500. A first subset of hotspots of the initial set is automatically selected 2860, based at least on the metastasis likelihood values computed at step 2850. Global hotspot features, such as those described with reference to process 2600 may also be used, and user input, for example received via interaction with a GUI, may also be used to select the first subset. Hotspots of the first subset are then used to calculate risk index values for the subject 2870. As described herein, the risk index calculation may include computing skeletal involvement factors 2872, adjusting the skeletal involvement factors using region dependent correction factors 2874, and summing the adjusted skeletal involvement factors 2876.

G. Example: BSI Calculation Performance

This example demonstrates linearity, precision, and reproducibility of computed BSI values.

i. Linearity and Accuracy

The automated BSI, the dependent variable, was determined from two sets of simulated bone scans and measured against known phantom-BSI, which was considered the independent variable. In the first set of 50 simulated bone scans, the Shapiro-Wilk test confirmed that the residuals of the dependent variable were normally distributed (p=0.850). Additionally, the mean residual value of 0.00 with a standard deviation of 0.25 confirmed homoscedasticity showing constant variation across all values of the independent variable. Given that the residuals exhibited normality and homoscedasticity, the model was considered linear. FIG. 25 shows a scatter plot with a linear fit line and the associated parameters for the linear regression in the range from 0.10 to 13.0 BSI are presented Table 1 below.

TABLE 1

The parameters for the linear regression model in the first set of 50 phantoms with the pre-defined BSI range of 0.10 to 13.0.

| Linearity measures | Value | 95% CI | Sig. |
|---|---|---|---|
| R | 0.99 | (0.99-0.99) | <0.0001 |
| Slope | 0.98 | (0.96-1.00) | <0.0001 | ii. Precision of BSI Calculation

Coefficient of variation and standard deviation of the automated BSI values at each of five predefined tumor burdens with varying localization were determined for a second set of 50 simulated bone scans. The coefficient of variation at each of the five pre-defined phantom-BSIs was less or equal to 30%. Results are shown in Table 2 below.

TABLE 2

Coefficient of variation and standard deviation of automated BSI values at each of five predefined tumor burdens

| Phantom-BSI; N = 50 | 0.5 N = 10 | 1.0 N = 10 | 3.0 N = 10 | 5.0 N = 10 | 10.0 N = 10 |
|---|---|---|---|---|---|
| SD | 0.18 | 0.14 | 0.25 | 0.27 | 0.30 |
| CV | 0.29 | 0.10 | 0.03 | 0.08 | 0.05 | iii. Reproducibility Using Different Cameras

Table 3 below shows simulation results for BSI values computed for 5 disease burdens and different cameras. The different collimator setting of the camera had minimal effect on the reproducibility of the BSI values. The standard deviation for each disease burden was <10%.

TABLE 3

BSI values calculated for simulations using different cameras.

| Simulation with Different Camera | Siemens Symbia Vs. Philips BrightView Vs. GE Infinia; | | | | |
|---|---|---|---|---|---|
| | Simulation of 0.5 BSI | Simulation of 1.0 BSI | Simulation of 3.0 BSI | Simulation of 5.0 BSI | Simulation of 10.0 BSI |
| Standard Deviation | 0.08 | 0.05 | 0.08 | 0.09 | 0.08 | iv. Reproducibility with Different Image Counts

FIG. 26 shows a Bland-Altman plot to evaluate the reproducibility of the automated BSI reads from 50 simulated phantoms. The mean and median BSI difference was 0.0 (solid horizontal line), and the standard deviation was 0.20, with coefficient of repeatability (2×SD) at 0.40 and at −0.40 (horizontal dotted lines). Descriptive statistics are presented in Table 4 below. Paired t-test demonstrated a p value of 0.15, suggesting that there is no statistically significant difference between the two aBSI values obtained on the repeat scans.

TABLE 4

Descriptive statistics showing reproducibility of automated BSI calculations from 50 simulated phantoms.

|  | aBSI 1st Scan | aBSI 2nd Scan | Diff |
|---|---|---|---|
| Minimum | 0 | 0 | −0.4 |
| 25% Percentile | 2.075 | 2.1 | −0.1 |
| Median | 5.45 | 5.3 | 0 |
| 75% Percentile | 8.525 | 8.725 | 0.12 |
| Maximum | 11.4 | 11.3 | 0.6 |
| Mean | 1.67 | 0.042 | 0.04 |
| Std. Deviation |  |  | 0.20 |
| Std. Error of Mean |  |  | 0.03 |
| Lower 95% CI |  |  | −0.01 |
| Upper 95% CI |  |  | 0.1 | v. Reproducibility with Repeat Scans on Patients

FIG. 27 shows a Bland-Altman plot to evaluate the reproducibility of the automated BSI reads from repeat bone scans of 35 metastatic patients. The mean and median BSI difference was 0.0 (solid horizontal line), and the standard deviation was 0.18, with coefficient of repeatability (2×SD) at 0.36 and at −0.36 (horizontal dotted lines). Descriptive statistics are presented in Table 5 below. A paired t-test demonstrated a p value of 0.09, suggesting that there is no statistically significant difference between the two aBSI values obtained on the repeat scans.

TABLE 5

Descriptive statistics showing reproducibility of automated BSI calculations from repeat bone scans of 35 metastatic patients.

|  | aBSI 1st Scan | aBSI 2nd Scan | Diff |
|---|---|---|---|
| Minimum | 0 | 0 | −0.3 |
| 25% Percentile | 0.1 | 0.1 | 0 |
| Median | 0.3 | 0.3 | 0 |
| 75% Percentile | 2.7 | 2.7 | 0.2 |
| Maximum | 9.6 | 9.9 | 0.4 |
| Mean | 1.67 | 1.72 | 0.05 |
| Std. Deviation |  |  | 0.18 |
| Std. Error of Mean |  |  | 0.02 |
| Lower 95% CI |  |  | −0.006 |
| Upper 95% CI |  |  | 0.10 | vi. Comparison with Predicate Device

FIG. 28A and FIG. 28B compare Bland-Altman plots of the BSI calculations for the an automated BSI device (software aBSI version 3.4), which utilizes the improvements of the present disclosure, and a predicate device (software EXINI version 1.7) implementing an earlier version of software that does not utilize the improvements of the present disclosure. Each plot shows difference between a known BSI value of a simulated phantom with the computed value for the phantom, using one of the two BSI software versions. FIG. 28A shows the differences between the known phantom values and the aBSI 3.4 computed values, while FIG. 28B shows the differences between the known phantom values and values computed using EXINI 1.7. The mean BSI difference (between the phantom and computed BSI values) was 0.14 for aBSI 3.4 and −0.89 for EXINI 1.7, indicated via the horizontal solid lines in FIG. 28A and FIG. 28B. The standard deviation of aBSI 3.4 (SD=0.30), which was observed to be significantly lower than that of EXINI 1.7 (SD=0.88). Descriptive statistics are presented in Tables 6A and 6B below.

TABLE 6A

Descriptive statistics for BSI values calculated with automated BSI (software version 3.4) employing the approaches described herein

|  | Phantom-BSI | aBSI 3.4 | Difference |
|---|---|---|---|
| Minimum | 0.14 | 0 | −0.71 |
| 25% Percentile | 1.49 | 1.67 | −0.04 |
| Median | 3.89 | 4.45 | 0.21 |
| 75% Percentile | 6.7 | 6.77 | 0.39 |
| Maximum | 9.98 | 10.1 | 0.67 |
| Mean | 4.236 | 4.37 | 0.14 |
| Std. Deviation |  |  | 0.30 |
| Std. Error of Mean |  |  | 0.05 |
| Lower 95% CI |  |  |  |
| Upper 95% CI |  |  | 0.04 |

TABLE 6B

Descriptive statistics for BSI values calculated with a predicate software (EXINI 1.7)

|  | Phantom-BSI | EXINI 1.7 | Difference |
|---|---|---|---|
| Minimum | 0.14 | 0.13 | −3.33 |
| 25% Percentile | 1.49 | 1.21 | −1.31 |
| Median | 3.89 | 3.46 | −0.58 |
| 75% Percentile | 6.7 | 5.43 | −0.19 |
| Maximum | 9.98 | 7.55 | 0.021 |
| Mean | 4.236 | 3.35 | −0.88 |
| Std. Deviation |  |  | 0.89 |
| Std. Error of Mean |  |  | 0.14 |
| Lower 95% CI |  |  |  |
| Upper 95% CI |  |  | −1.17 |

H. Computer System and Network Environment

Figure 33A:
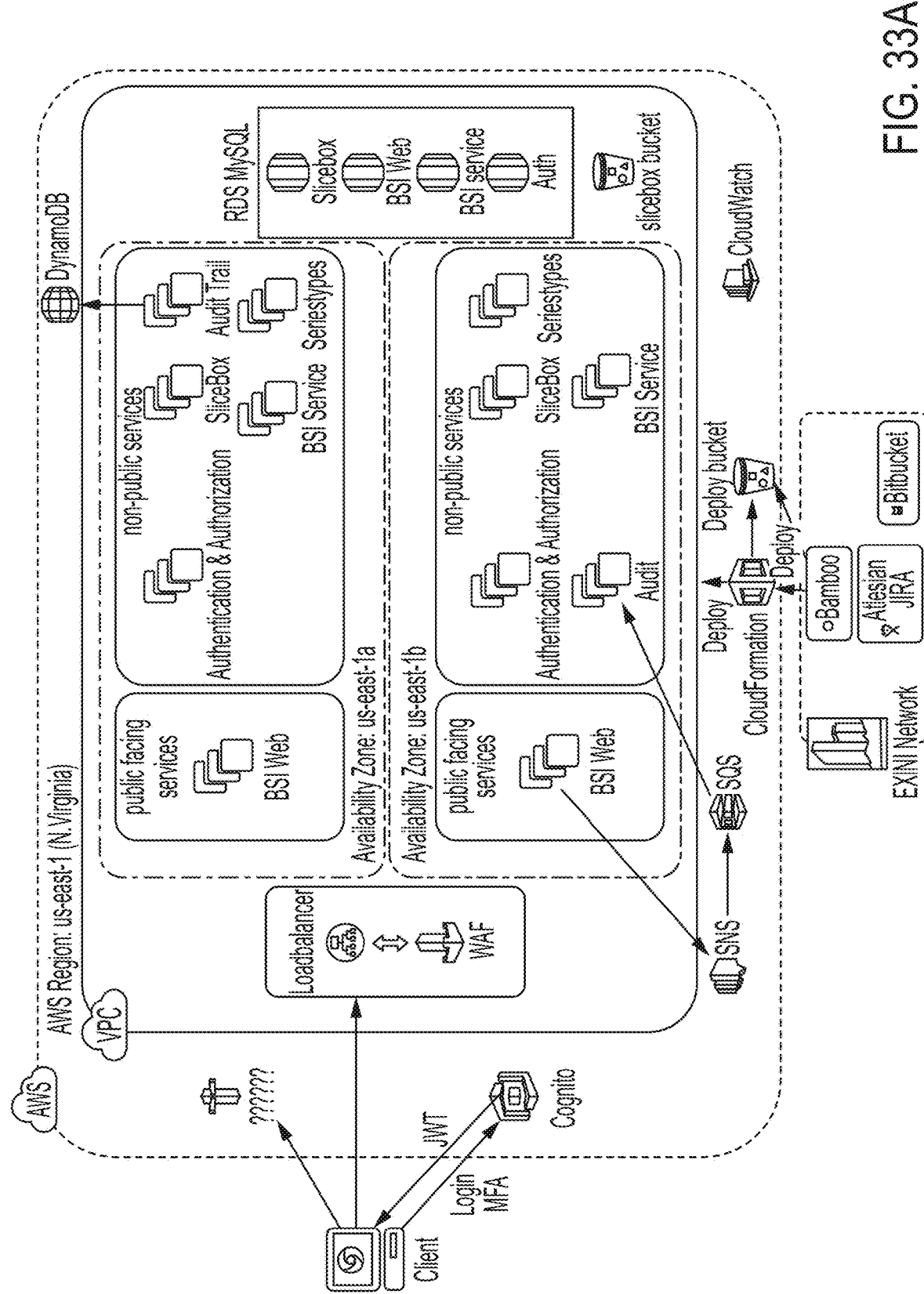
FIG. 33A is a diagram showing an exemplary cloud platform architecture.
Figure 33B:
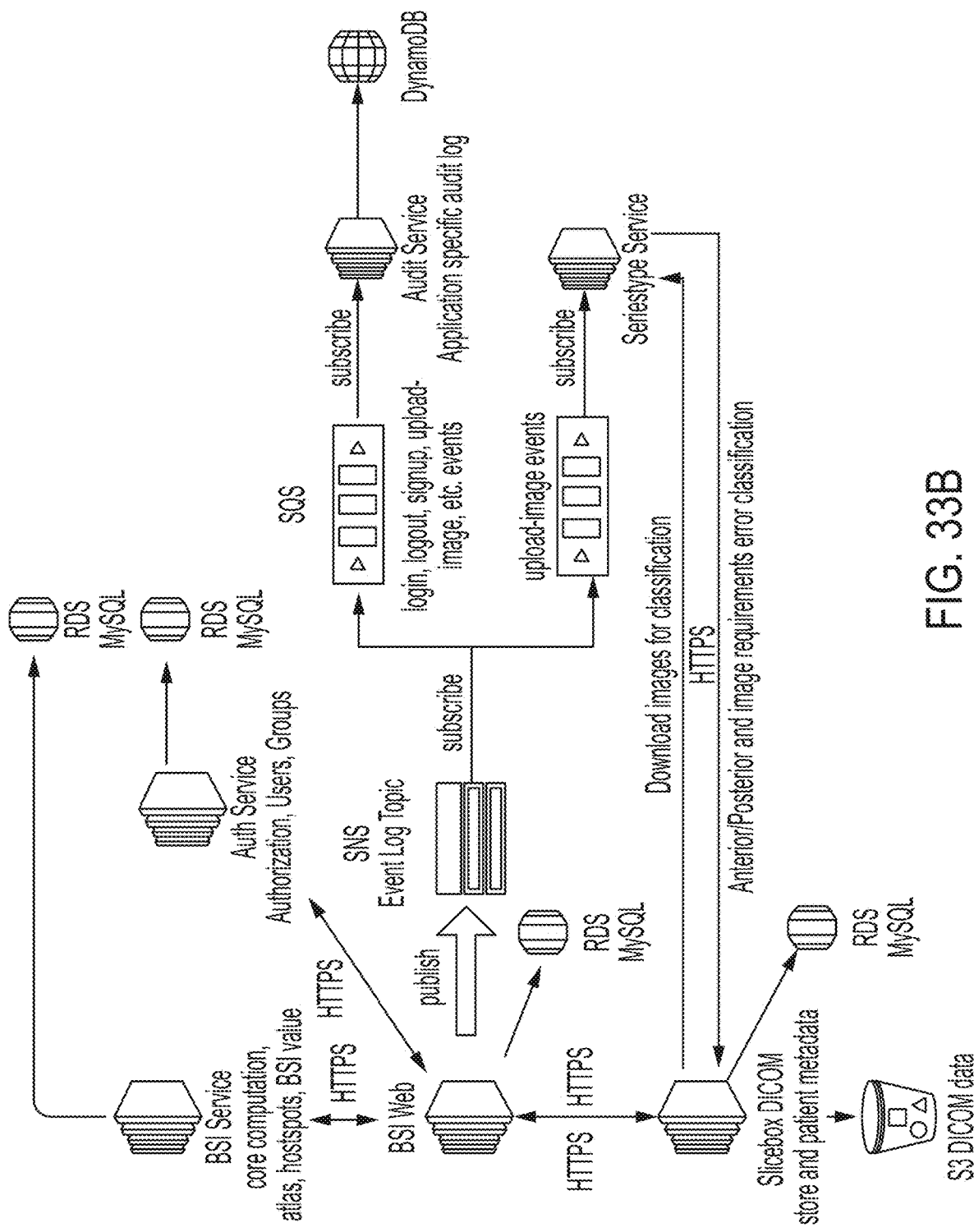
FIG. 33B is a diagram showing an example microservices architecture.

In certain embodiments, the systems and methods described herein are implemented using a cloud-based microservices architecture. FIG. 33A shows an example cloud platform architecture, and FIG. 33B shows an example microservice communication design chart.

Figure 34:
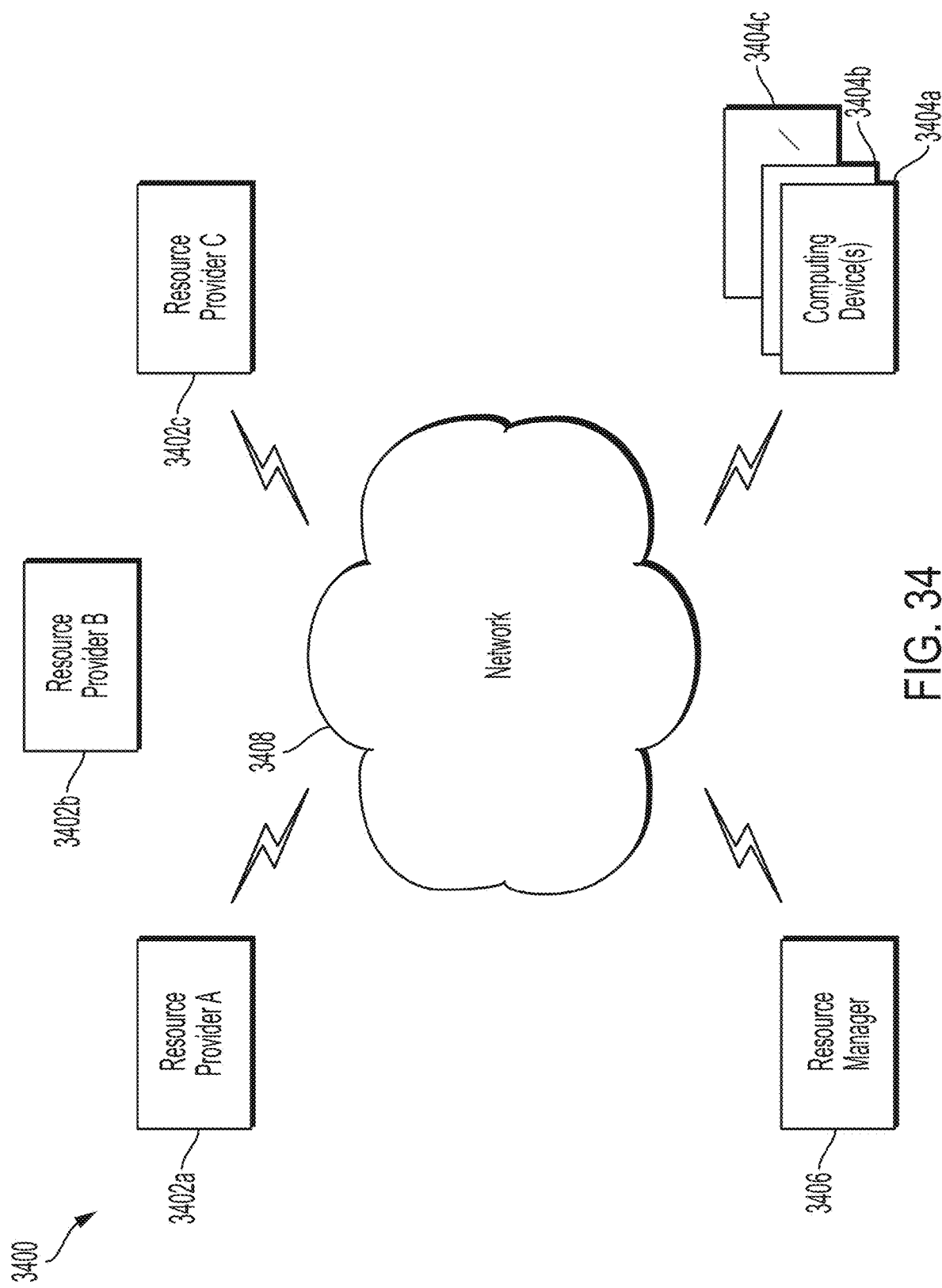
FIG. 34 is a block diagram of an exemplary cloud computing environment, used in certain embodiments.

FIG. 34 shows an illustrative network environment 3400 for use in the methods and systems described herein. In brief overview, referring now to FIG. 34, a block diagram of an exemplary cloud computing environment 3400 is shown and described. The cloud computing environment 3400 may include one or more resource providers 3402a, 3402b, 3402c (collectively, 3402). Each resource provider 3402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 3402 may be connected to any other resource provider 3402 in the cloud computing environment 3400. In some implementations, the resource providers 3402 may be connected over a computer network 3408. Each resource provider 3402 may be connected to one or more computing device 3404a, 3404b, 3404c (collectively, 3404), over the computer network 3408.

The cloud computing environment 3400 may include a resource manager 3406. The resource manager 3406 may be connected to the resource providers 3402 and the computing devices 3404 over the computer network 3408. In some implementations, the resource manager 3406 may facilitate the provision of computing resources by one or more resource providers 3402 to one or more computing devices 3404. The resource manager 3406 may receive a request for a computing resource from a particular computing device 3404. The resource manager 3406 may identify one or more resource providers 3402 capable of providing the computing resource requested by the computing device 3404. The resource manager 3406 may select a resource provider 3402 to provide the computing resource. The resource manager 3406 may facilitate a connection between the resource provider 3402 and a particular computing device 3404. In some implementations, the resource manager 3406 may establish a connection between a particular resource provider 3402 and a particular computing device 3404. In some implementations, the resource manager 3406 may redirect a particular computing device 3404 to a particular resource provider 3402 with the requested computing resource.

Figure 35:
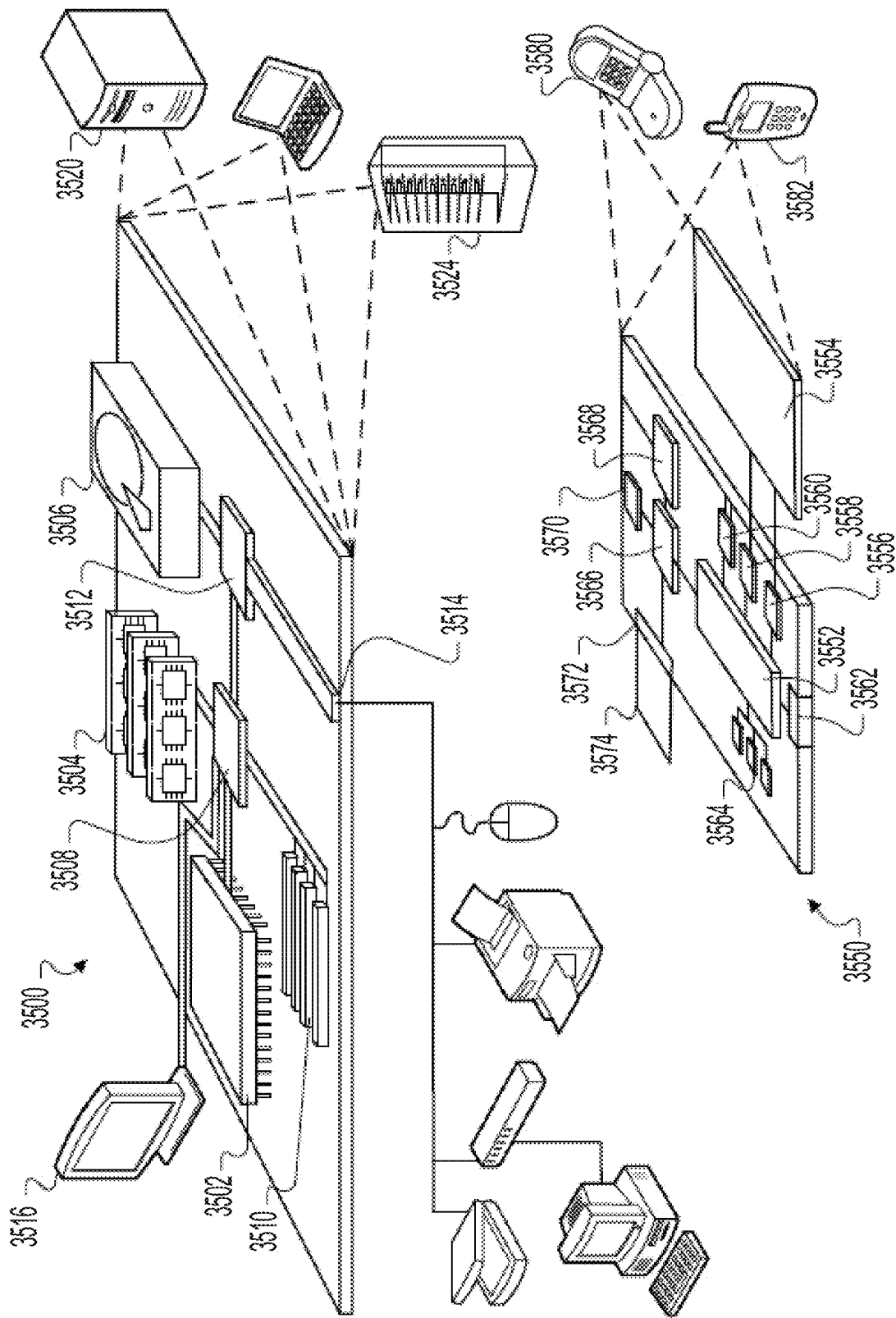
FIG. 35 is a block diagram of an example computing device and an example mobile computing device used in certain embodiments The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

FIG. 35 shows an example of a computing device 3500 and a mobile computing device 3550 that can be used in the methods and systems described in this disclosure. The computing device 3500 is intended to represent various forms of digital computers, such as laptops, desktops, workstations, personal digital assistants, servers, blade servers, mainframes, and other appropriate computers. The mobile computing device 3550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 3500 includes a processor 3502, a memory 3504, a storage device 3506, a high-speed interface 3508 connecting to the memory 3504 and multiple high-speed expansion ports 3510, and a low-speed interface 3512 connecting to a low-speed expansion port 3514 and the storage device 3506. Each of the processor 3502, the memory 3504, the storage device 3506, the high-speed interface 3508, the high-speed expansion ports 3510, and the low-speed interface 3512, are interconnected using various busses, and may be mounted on a common motherboard or in other manners as appropriate. The processor 3502 can process instructions for execution within the computing device 3500, including instructions stored in the memory 3504 or on the storage device 3506 to display graphical information for a GUI on an external input/output device, such as a display 3516 coupled to the high-speed interface 3508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 3504 stores information within the computing device 3500. In some implementations, the memory 3504 is a volatile memory unit or units. In some implementations, the memory 3504 is a non-volatile memory unit or units. The memory 3504 may also be another form of computer-readable medium, such as a magnetic or optical disk.

The storage device 3506 is capable of providing mass storage for the computing device 3500. In some implementations, the storage device 3506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 3502), perform one or more methods, such as those described above. The instructions can also be stored by one or more storage devices such as computer- or machine-readable mediums (for example, the memory 3504, the storage device 3506, or memory on the processor 3502).

The high-speed interface 3508 manages bandwidth-intensive operations for the computing device 3500, while the low-speed interface 3512 manages lower bandwidth-intensive operations. Such allocation of functions is an example only. In some implementations, the high-speed interface 3508 is coupled to the memory 3504, the display 3516 (e.g., through a graphics processor or accelerator), and to the high-speed expansion ports 3510, which may accept various expansion cards (not shown). In the implementation, the low-speed interface 3512 is coupled to the storage device 3506 and the low-speed expansion port 3514. The low-speed expansion port 3514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 3500 may be implemented in a number of different forms, as shown in the figure. For example, it may be implemented as a standard server 3520, or multiple times in a group of such servers. In addition, it may be implemented in a personal computer such as a laptop computer 3522. It may also be implemented as part of a rack server system 3524. Alternatively, components from the computing device 3500 may be combined with other components in a mobile device (not shown), such as a mobile computing device 3550. Each of such devices may contain one or more of the computing device 3500 and the mobile computing device 3550, and an entire system may be made up of multiple computing devices communicating with each other.

The mobile computing device 3550 includes a processor 3552, a memory 3564, an input/output device such as a display 3554, a communication interface 3566, and a transceiver 3568, among other components. The mobile computing device 3550 may also be provided with a storage device, such as a micro-drive or other device, to provide additional storage. Each of the processor 3552, the memory 3564, the display 3554, the communication interface 3566, and the transceiver 3568, are interconnected using various buses, and several of the components may be mounted on a common motherboard or in other manners as appropriate.

The processor 3552 can execute instructions within the mobile computing device 3550, including instructions stored in the memory 3564. The processor 3552 may be implemented as a chipset of chips that include separate and multiple analog and digital processors. The processor 3552 may provide, for example, for coordination of the other components of the mobile computing device 3550, such as control of user interfaces, applications run by the mobile computing device 3550, and wireless communication by the mobile computing device 3550.

The processor 3552 may communicate with a user through a control interface 3558 and a display interface 3556 coupled to the display 3554. The display 3554 may be, for example, a TFT (Thin-Film-Transistor Liquid Crystal Display) display or an OLED (Organic Light Emitting Diode) display, or other appropriate display technology. The display interface 3556 may comprise appropriate circuitry for driving the display 3554 to present graphical and other information to a user. The control interface 3558 may receive commands from a user and convert them for submission to the processor 3552. In addition, an external interface 3562 may provide communication with the processor 3552, so as to enable near area communication of the mobile computing device 3550 with other devices. The external interface 3562 may provide, for example, for wired communication in some implementations, or for wireless communication in other implementations, and multiple interfaces may also be used.

The memory 3564 stores information within the mobile computing device 3550. The memory 3564 can be implemented as one or more of a computer-readable medium or media, a volatile memory unit or units, or a non-volatile memory unit or units. An expansion memory 3574 may also be provided and connected to the mobile computing device 3550 through an expansion interface 3572, which may include, for example, a SIMM (Single In Line Memory Module) card interface. The expansion memory 3574 may provide extra storage space for the mobile computing device 3550, or may also store applications or other information for the mobile computing device 3550. Specifically, the expansion memory 3574 may include instructions to carry out or supplement the processes described above, and may include secure information also. Thus, for example, the expansion memory 3574 may be provided as a security module for the mobile computing device 3550, and may be programmed with instructions that permit secure use of the mobile computing device 3550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 3552), perform one or more methods, such as those described above. The instructions can also be stored by one or more storage devices, such as one or more computer- or machine-readable mediums (for example, the memory 3564, the expansion memory 3574, or memory on the processor 3552). In some implementations, the instructions can be received in a propagated signal, for example, over the transceiver 3568 or the external interface 3562.

The mobile computing device 3550 may communicate wirelessly through the communication interface 3566, which may include digital signal processing circuitry where necessary. The communication interface 3566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 3568 using a radio-frequency. In addition, short-range communication may occur, such as using a Bluetooth®, Wi-Fi™, or other such transceiver (not shown). In addition, a GPS (Global Positioning System) receiver module 3570 may provide additional navigation- and location-related wireless data to the mobile computing device 3550, which may be used as appropriate by applications running on the mobile computing device 3550.

The mobile computing device 3550 may also communicate audibly using an audio codec 3560, which may receive spoken information from a user and convert it to usable digital information. The audio codec 3560 may likewise generate audible sound for a user, such as through a speaker, e.g., in a handset of the mobile computing device 3550. Such sound may include sound from voice telephone calls, may include recorded sound (e.g., voice messages, music files, etc.) and may also include sound generated by applications operating on the mobile computing device 3550.

The mobile computing device 3550 may be implemented in a number of different forms, as shown in the figure. For example, it may be implemented as a cellular telephone 3580. It may also be implemented as part of a smart-phone 3582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. In some implementations, the modules and/or services described herein can be separated, combined or incorporated into single or combined modules and/or services. The modules and/or services depicted in the figures are not intended to limit the systems described herein to the software architectures shown therein While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for lesion marking and quantitative analysis of nuclear medicine images of a human subject, the method comprising:
   (a) accessing, by a processor of a computing device, a bone scan image set for the human subject, said bone scan image set obtained following administration of an agent to the human subject;
   (b) automatically segmenting, by the processor, each image in the bone scan image set to identify one or more skeletal regions of interest, each corresponding to a particular anatomical region of a skeleton of the human subject, thereby obtaining an annotated set of images, wherein the one or more skeletal regions of interest comprise at least one of (i) and (ii):
      (i) a femur region corresponding to a portion of a femur of the human subject; and
      (ii) a humerus region corresponding to a portion of a humerus of the human subject;
   (c) automatically detecting, by the processor, an initial set of one or more hotspots, each hotspot corresponding to an area of elevated intensity in the annotated set of images, said automatically detecting comprising identifying the one or more hotspots using intensities of pixels in the annotated set of images and using one or more region-dependent threshold values, and wherein the one or more region dependent threshold values include one or more values associated with the femur region and/or the humerus region that provide enhanced hotspot detection sensitivity in the femur region and/or the humerus region to compensate for reduced uptake of the agent therein;
   (d) for each hotspot in the initial set of hotspots, extracting, by the processor, a set of hotspot features associated with the hotspot;
   (e) for each hotspot in the initial set of hotspots, calculating, by the processor, a metastasis likelihood value corresponding to a likelihood of the hotspot representing a metastasis, based on the set of hotspot features associated with the hotspot; and
   (f) causing, by the processor, rendering of a graphical representation of at least a portion of the initial set of hotspots for display within a graphical user interface (GUI),
   wherein the one or more region dependent threshold values comprise (i) a first, reduced intensity, threshold value associated with the femur region and/or the humerus region and (ii) a second threshold value associated with one or more other skeletal regions of interest, wherein the first threshold value is lower than the second threshold value, thereby increasing detection sensitivity in the femur region and/or the humerus region.

2. The method of claim 1, wherein step (b) comprises:
comparing each member of the bone scan image set with a corresponding atlas image of an atlas image set, each atlas image comprising one or more identifications of the one or more skeletal regions of interest, said skeletal regions of interest including the femur region and/or the humerus region; and
for each image of the bone scan image set, registering the corresponding atlas image with the image of the bone scan image set, such that the identifications of the one or more skeletal regions of interest of the atlas image are applied to the image of the bone scan image set.

3. The method of claim 2, wherein each atlas image comprises an identification of (i) the femur region comprising at least a portion of a knee region of the human subject and/or (ii) the humerus region comprising at least a portion of an elbow region of the human subject, and wherein, for each image of the bone scan image set, the registering of the corresponding atlas image to the bone scan image comprises using the identified knee region and/or the identified elbow region in the image as (a) landmark(s).

4. The method of claim 1, wherein a location of at least one detected hotspot of the initial hotspot set corresponds to a physical location in or on a femur more than three quarters of a distance along the femur from an end of the femur oriented toward a hip of the human subject to an end of the femur oriented toward a knee of the human subject.

5. The method of claim 1, wherein a location of at least one detected hotspot of the initial hotspot set corresponds to a physical location in or on a humerus more than three quarters of a distance along the humerus from an end of the humerus oriented toward a shoulder of the human subject to an end of the humerus oriented toward an elbow of the human subject.

6. The method of claim 1, where step (c) comprises:
identifying, by the processor, healthy tissue regions in the images of the bone scan image set determined not to include any hotspots;
calculating, by the processor, a normalization factor such that a product of the normalization factor and an average intensity of the identified healthy tissue regions is a pre-defined intensity level; and
normalizing, by the processor, the images of the bone scan image set by the normalization factor.

7. The method of claim 1, further comprising:
(g) calculating, by the processor, one or more risk index values for the human subject based at least in part on a computed fraction of the skeleton of the human subject occupied by the initial set of hotspots.

8. The method of claim 7, wherein at least one of the risk index values is indicative of a risk of the human subject having and/or developing metastatic cancer.

9. The method of claim 8, wherein the metastatic cancer is metastatic prostate cancer.

10. The method of claim 7, wherein at least one of the risk index values is indicative of the human subject having a particular state of metastatic cancer.

11. The method of claim 1, comprising:
(h) selecting, by the processor, a first subset of the initial set of hotspots based at least in part on the metastasis likelihood values; and
(i) causing, by the processor, rendering of a graphical representation of the first subset for display within a graphical user interface (GUI).

12. The method of claim 11, further comprising:
(j) calculating, by the processor, one or more risk index values for the human subject based at least in part on a computed fraction of the skeleton of the human subject occupied by the first subset of hotspots.

13. The method of claim 1, comprising:
(k) receiving, by the processor, via the GUI, a user selection of a second subset of the initial set of hotspots; and
(l) calculating, by the processor, one or more risk index values for the human subject based at least in part on a computed fraction of the skeleton of the human subject occupied by the second subset of hotspots.

14. The method of claim 1, wherein the processor is a processor of a cloud-based system.

15. The method of claim 1, wherein the GUI is part of a general Picture Archiving and Communications System (PACS).

16. The method of claim 1, wherein the agent comprises technetium 99m methylenediphosphonate ($^{99m}$Tc-MDP).

17. A system for lesion marking and quantitative analysis of nuclear medicine images of a human subject, the system comprising:
a processor; and
a memory having instructions thereon, wherein the instructions, when executed by the processor, cause the processor to:
(a) access a bone scan image set for the human subject, said bone scan image set obtained following administration of an agent to the human subject;
(b) automatically segment each image in the bone scan image set to identify one or more skeletal regions of interest, each corresponding to a particular anatomical region of a skeleton of the human subject, thereby obtaining an annotated set of images, wherein the one or more skeletal regions of interest comprise at least one of (i) and (ii):
(i) a femur region corresponding to a portion of a femur of the human subject; and
(ii) a humerus region corresponding to a portion of a humerus of the human subject;
(c) automatically detect an initial set of one or more hotspots, each hotspot corresponding to an area of elevated intensity in the annotated set of images, said automatically detecting comprising identifying the one or more hotspots using intensities of pixels in the annotated set of images and using one or more region-dependent threshold values, and wherein the one or more region dependent threshold values include one or more values associated with the femur region and/or the humerus region that provide enhanced hotspot detection sensitivity in the femur region and/or the humerus region to compensate for reduced uptake of the agent therein;
(d) for each hotspot in the initial set of hotspots, extract a set of hotspot features associated with the hotspot;
(e) for each hotspot in the initial set of hotspots, calculate a metastasis likelihood value corresponding to a likelihood of the hotspot representing a metastasis, based on the set of hotspot features associated with the hotspot; and
(f) cause rendering of a graphical representation of at least a portion of the initial set of hotspots for display within a graphical user interface (GUI),
wherein the one or more region dependent threshold values comprise (i) a first, reduced intensity, threshold value associated with the femur region and/or the humerus region and (ii) a second threshold value associated with one or more other skeletal regions of interest, wherein the first threshold value is lower than the second threshold value, thereby increasing detection sensitivity in the femur region and/or the humerus region.

18. A computer aided image analysis device comprising the system of claim 17.

19. The device of claim 18, wherein the device is programmed to be used by trained healthcare professionals and/or researchers.

20. The device of claim 19, wherein the device is programmed to be used for analysis of bone scan images for evaluation and/or detection of metastatic cancer.

21. The device of claim 19, wherein the device is programmed to be used for analysis of bone scan images for evaluation and/or detection of prostate cancer.

22. The device of claim 18, comprising a label specifying that the device is intended to be used by trained healthcare professionals and/or researchers.

23. The device of claim 22, wherein the label further specifies that the device is intended to be used for analysis of bone scan images for evaluation and/or detection of metastatic cancer.

24. The device of claim 22, wherein the label further specifies that the device is intended to be used for analysis of bone scan images for evaluation and/or detection of prostate cancer.

25. A computer aided image analysis device comprising a system for lesion marking and quantitative analysis of nuclear medicine images of a human subject and a label specifying that the device is intended to be used by trained healthcare professionals and/or researchers, wherein the system comprises:
a processor; and
a memory having instructions thereon, wherein the instructions, when executed by the processor, cause the processor to:
(a) access a bone scan image set for the human subject, said bone scan image set obtained following administration of an agent to the human subject;
(b) automatically segment each image in the bone scan image set to identify one or more skeletal regions of interest, each corresponding to a particular anatomical region of a skeleton of the human subject, thereby obtaining an annotated set of images, wherein the one or more skeletal regions of interest comprise at least one of (i) and (ii):
  (i) a femur region corresponding to a portion of a femur of the human subject; and
  (ii) a humerus region corresponding to a portion of a humerus of the human subject;
(c) automatically detect an initial set of one or more hotspots, each hotspot corresponding to an area of elevated intensity in the annotated set of images, said automatically detecting comprising identifying the one or more hotspots using intensities of pixels in the annotated set of images and using one or more region-dependent threshold values, and wherein the one or more region dependent threshold values include one or more values associated with the femur region and/or the humerus region that provide enhanced hotspot detection sensitivity in the femur region and/or the humerus region to compensate for reduced uptake of the agent therein;
(d) for each hotspot in the initial set of hotspots, extract a set of hotspot features associated with the hotspot;
(e) for each hotspot in the initial set of hotspots, calculate a metastasis likelihood value corresponding to a likelihood of the hotspot representing a metastasis, based on the set of hotspot features associated with the hotspot; and
(f) cause rendering of a graphical representation of at least a portion of the initial set of hotspots for display within a graphical user interface (GUI).

26. The device of claim 25, wherein the label further specifies that the device is intended to be used for analysis of bone scan images for evaluation and/or detection of metastatic cancer.

27. The device of claim 25, wherein the label further specifies that the device is intended to be used for analysis of bone scan images for evaluation and/or detection of prostate cancer.

28. The device of claim 25, wherein the device is programmed to be used by trained healthcare professionals and/or researchers.

29. The device of claim 28, wherein the device is programmed to be used for analysis of bone scan images for evaluation and/or detection of metastatic cancer.

30. The device of claim 28, wherein the device is programmed to be used for analysis of bone scan images for evaluation and/or detection of prostate cancer.

* * * * *